(12) United States Patent
Meiri et al.

(10) Patent No.: US 12,274,678 B2
(45) Date of Patent: Apr. 15, 2025

(54) CANNABINOIDS AND USES THEREOF

(71) Applicants: TECHNION RESEARCH & DEVELOPMENT FOUNDATION LIMITED, Haifa (IL); RAMOT AT TEL-AVIV UNIVERSITY LTD., Tel-Aviv (IL)

(72) Inventors: David Meiri, Haifa (IL); Elazar Besser, Haifa (IL); Igal Louria-Hayon, Haifa (IL); Paula Berman, Haifa (IL); Gil Moshe Lewitus, Haifa (IL); Limor Broday, Tel-Aviv (IL)

(73) Assignees: TECHNION RESEARCH & DEVELOPMENT FOUNDATION LIMITED, Haifa (IL); RAMOT AT TEL-AVIV UNIVERSITY LTD., Tel-Aviv (IL)

( * ) Notice: Subject to any disclaimer, the term of this patent is extended or adjusted under 35 U.S.C. 154(b) by 760 days.

(21) Appl. No.: 17/611,093

(22) PCT Filed: May 17, 2020

(86) PCT No.: PCT/IL2020/050538
§ 371 (c)(1),
(2) Date: Nov. 12, 2021

(87) PCT Pub. No.: WO2020/230145
PCT Pub. Date: Nov. 19, 2020

(65) Prior Publication Data
US 2022/0265570 A1    Aug. 25, 2022

Related U.S. Application Data

(60) Provisional application No. 62/848,695, filed on May 16, 2019.

(51) Int. Cl.
*A61K 31/05*    (2006.01)
*A61P 35/00*    (2006.01)

(52) U.S. Cl.
CPC .............. *A61K 31/05* (2013.01); *A61P 35/00* (2018.01)

(58) Field of Classification Search
CPC ................................. A61K 31/05; A61P 35/00
USPC ........................................................ 514/729
See application file for complete search history.

(56) References Cited

U.S. PATENT DOCUMENTS

| | | | |
|---|---|---|---|
| 4,235,871 A | 11/1980 | Papahadjopoulos | |
| 4,501,728 A | 2/1985 | Geho | |
| 4,666,828 A | 5/1987 | Gusella | |
| 4,683,202 A | 7/1987 | Mullis | |
| 4,801,531 A | 1/1989 | Frossard | |
| 4,837,028 A | 6/1989 | Allen | |
| 5,019,369 A | 5/1991 | Presant | |
| 5,192,659 A | 3/1993 | Simons | |
| 5,272,057 A | 12/1993 | Smulson | |
| 2006/0074252 A1 | 4/2006 | Souza | |

FOREIGN PATENT DOCUMENTS

| CN | 111084765 A | 5/2020 |
|---|---|---|
| EP | 0494665 A1 | 7/1992 |
| WO | 03049727 A1 | 6/2003 |
| WO | 2008144475 A1 | 11/2008 |
| WO | 2011110866 A1 | 9/2011 |
| WO | 2013038157 A1 | 3/2013 |
| WO | 2018154280 A1 | 8/2018 |
| WO | 2018205038 A1 | 11/2018 |
| WO | 2020024009 A1 | 2/2020 |
| WO | 2020024011 A1 | 2/2020 |
| WO | 2020223510 A1 | 11/2020 |
| WO | 2021151168 A1 | 8/2021 |

OTHER PUBLICATIONS

Gao Bingbing (2016) Cannabidiol Can Provide Neuroprotection in a Mouse Model of Intracerebral Hemorrhage and the Mechanism Research. Published Oct. 15, 2016, Thesis; China Excellent Master's Thesis Database. Anhui Medical University. 43 pages. English abstract and machine translation of pp. 20-21.
Baram et al., (2019) The heterogeneity and complexity of Cannabis extracts as antitumor agents. Oncotarget 10(41): 4091-4106.
Berman et al., (2018) A new ESI-LC/MS approach for comprehensive metabolic profiling of phytocannabinoids in Cannabis. Sci Rep 8(1): 14280.
Borggrefe and Oswald (2009) The Notch signaling pathway: transcriptional regulation at Notch target genes. Cell Mol Life Sci 66(10): 1631-1646.
Buchwald et al., (1980) Long-term, continuous intravenous heparin administration by an implantable infusion pump in ambulatory patients with recurrent venous thrombosis. Surgery 88(4): 507-516.
Horváth et al., (2019) Methodological refinement of Aldara-induced psoriasiform dermatitis model in mice. Sci Rep 9 (1): 3685.
Langer (1990) New methods of drug delivery. Science 249(4976): 1527-1533.
Punzo et al., (2017) Anti-proliferative, pro-apoptotic and anti-invasive effect of EC/EV system in human osteosarcoma. Oncotarget 8(33): 54459-54471.
Reece and Hulse (2019) Impacts of cannabinoid epigenetics on human development: reflections on Murphy et al. cannabinoid exposure and altered DNA methylation in rat and human sperm' epigenetics 2018; 13: 1208-1221. Epigenetics 14(11): 1041-1056.

(Continued)

*Primary Examiner* — Kristin A Vajda
(74) *Attorney, Agent, or Firm* — Rodney J. Fuller; Booth Udall Fuller, PLC

(57) ABSTRACT

The present invention provides a pharmaceutical composition including a combination of at least two cannabinoids, and methods of using same, such as for treating a NOTCH 1-related disease.

23 Claims, 31 Drawing Sheets
Specification includes a Sequence Listing.

(56) References Cited

OTHER PUBLICATIONS

Sanjana et al., (2014) Improved vectors and genome-wide libraries for CRISPR screening. Nat Methods. Author manuscript; available in PMC Jun. 3, 20150. Published in final edited form as: Nat Methods. Aug. 2014; 11(8): 783-784.

Saudek et al., (1989) A preliminary trial of the programmable implantable medication system for insulin delivery. N Engl J Med 321(9): 574-579.

Sefton (1987) Implantable pumps. Crit Rev Biomed Eng 14(3): 201-240.

Somovilla-Crespo et al., (2018) 92R Monoclonal Antibody Inhibits Human CCR9+ Leukemia Cells Growth in NSG Mice Xenografts. Front Immunol 9: 77.

Van der Fits et al., (2009) Imiquimod-induced psoriasis-like skin inflammation in mice is mediated via the IL-23/IL-17 axis. J Immunol 182(9): 5836-5845.

Wang et al., (2020) Notch-Hes1 Signaling Regulates IL-17A+γδ+T Cell Expression and IL-17A Secretion of Mouse Psoriasis-Like Skin Inflammation. Mediators Inflamm 2020: 8297134.

| | Δ9-THCA | Δ9-THC | CBDA | CBD | CBGA | CBG | CBDVA | CBDV | THCV | CBNA | CBN | CBCA | CBC | CBL | Δ8-THC | Cannabicitran |
|---|---|---|---|---|---|---|---|---|---|---|---|---|---|---|---|---|
| Extract 1 | 0.51 | 49.53 | <LOQ | 0.12 | <LOQ | 1.51 | <LOQ | 0.02 | 0.36 | <LOQ | 0.94 | <LOQ | 0.83 | <LOQ | <LOQ | <LOQ |
| Extract 2 | 3.47 | 54.65 | <LOQ | 0.09 | 1.44 | 2.81 | <LOQ | 0.04 | 0.31 | <LOQ | 1.15 | <LOQ | 0.65 | <LOQ | <LOQ | <LOQ |
| Extract 3 | 4.39 | 45.92 | <LOQ | 0.07 | 0.64 | 1.46 | <LOQ | 0.05 | 0.24 | <LOQ | 0.37 | <LOQ | 1.04 | <LOQ | <LOQ | <LOQ |
| Extract 4 | 4.21 | 65.71 | <LOQ | 0.15 | <LOQ | 1.42 | <LOQ | 0.07 | 0.20 | <LOQ | 0.78 | <LOQ | 1.37 | <LOQ | <LOQ | <LOQ |
| Extract 5 | 0.06 | 66.11 | <LOQ | 0.18 | <LOQ | 2.50 | <LOQ | <LOQ | 0.46 | <LOQ | 1.10 | <LOQ | 1.27 | <LOQ | <LOQ | <LOQ |
| Extract 6 | 40.01 | 9.76 | <LOQ | <LOQ | 0.94 | 0.36 | <LOQ | <LOQ | 0.05 | <LOQ | 0.29 | <LOQ | 0.18 | <LOQ | <LOQ | <LOQ |
| Extract 7 | 44.31 | 3.96 | <LOQ | <LOQ | 2.71 | 0.33 | <LOQ | <LOQ | <LOQ | <LOQ | 0.09 | <LOQ | 0.05 | <LOQ | <LOQ | <LOQ |
| Extract 8 | 38.19 | 3.23 | <LOQ | <LOQ | 1.05 | 0.43 | <LOQ | <LOQ | 0.05 | <LOQ | 0.05 | <LOQ | 0.18 | <LOQ | <LOQ | <LOQ |
| Extract 9 | 58.97 | 8.68 | 0.53 | 0.70 | 0.79 | 0.63 | <LOQ | <LOQ | 0.08 | <LOQ | 0.15 | <LOQ | 0.12 | <LOQ | <LOQ | <LOQ |
| Extract 10 | 53.10 | 6.22 | <LOQ | 0.02 | 2.07 | 0.42 | 0.07 | 0.10 | 0.03 | <LOQ | 0.08 | <LOQ | 0.19 | <LOQ | <LOQ | <LOQ |
| Extract 11 | 1.12 | 1.73 | 22.42 | 21.07 | 0.37 | 0.62 | <LOQ | 2.89 | 0.27 | <LOQ | 0.15 | <LOQ | 0.87 | <LOQ | <LOQ | <LOQ |
| Extract 12 | <LOQ | 3.13 | 0.27 | 56.20 | <LOQ | 0.64 | <LOQ | 0.14 | 0.18 | <LOQ | 0.12 | <LOQ | 2.95 | <LOQ | <LOQ | <LOQ |
| Extract 13 | 0.14 | 19.81 | 0.30 | 25.38 | <LOQ | 1.13 | <LOQ | <LOQ | 0.24 | <LOQ | 0.72 | <LOQ | 1.62 | <LOQ | <LOQ | <LOQ |
| Extract 14 | <LOQ | 23.25 | 3.60 | 35.26 | 0.19 | 1.19 | 0.21 | 0.20 | 0.26 | <LOQ | 0.10 | 0.12 | 2.03 | <LOQ | <LOQ | <LOQ |
| Extract 15 | 0.17 | 39.19 | 3.14 | 23.14 | 0.26 | 1.46 | <LOQ | 0.31 | <LOQ | <LOQ | 0.25 | <LOQ | 1.55 | <LOQ | <LOQ | <LOQ |
| Extract 16 | <LOQ | 2.25 | 0.19 | 51.20 | <LOQ | 1.15 | <LOQ | 4.83 | 0.10 | <LOQ | 0.05 | <LOQ | 2.84 | <LOQ | <LOQ | 0.32 |
| Extract 17 | <LOQ | 2.26 | 1.07 | 53.93 | <LOQ | 2.09 | <LOQ | 3.15 | <LOQ | <LOQ | 0.20 | <LOQ | 2.69 | <LOQ | <LOQ | 0.38 |
| Extract 18 | <LOQ | 2.32 | 1.11 | 56.81 | <LOQ | 1.13 | <LOQ | 0.05 | <LOQ | <LOQ | 0.16 | <LOQ | 3.08 | <LOQ | <LOQ | 0.48 |
| Extract 19 | <LOQ | 2.18 | 4.61 | 41.58 | 0.22 | 1.82 | <LOQ | 0.05 | <LOQ | <LOQ | 0.04 | <LOQ | 2.18 | <LOQ | <LOQ | <LOQ |

FIGURE 4

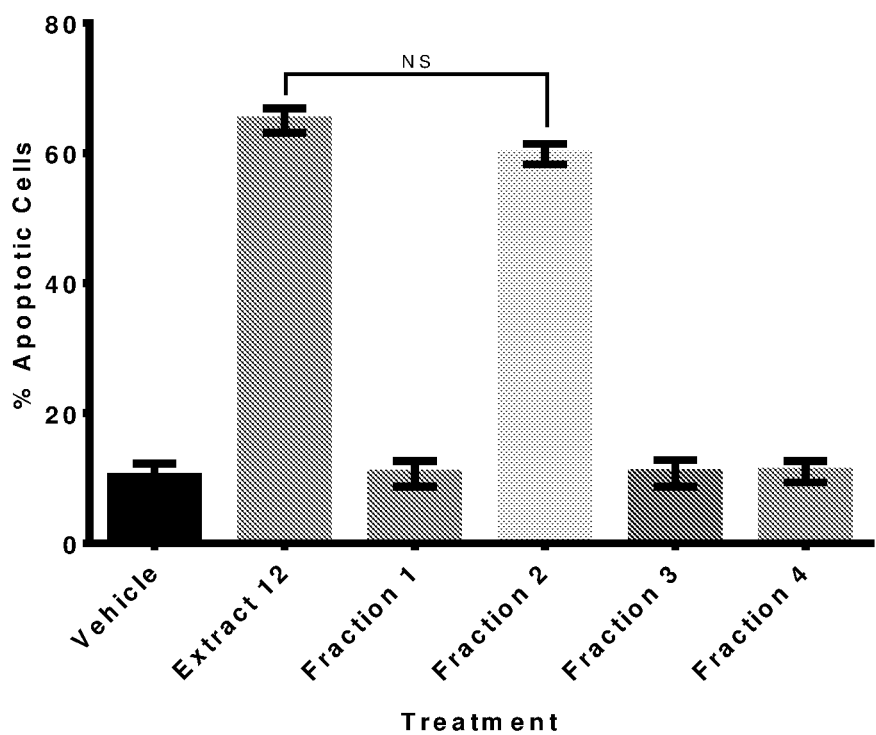
FIGURE 10Cii

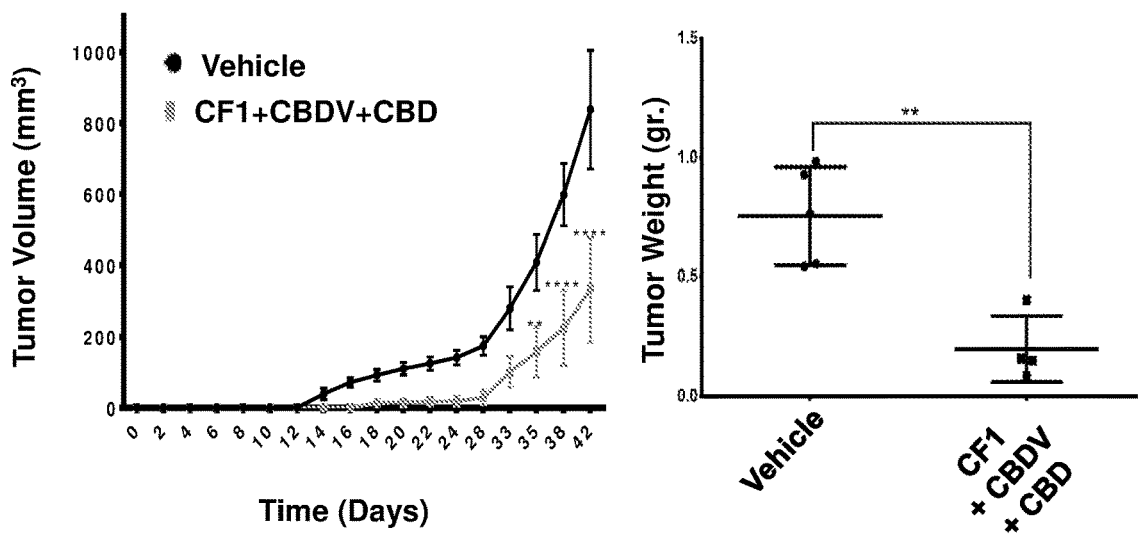
FIGURE 13A
FIGURE 13B
FIGURE 13C
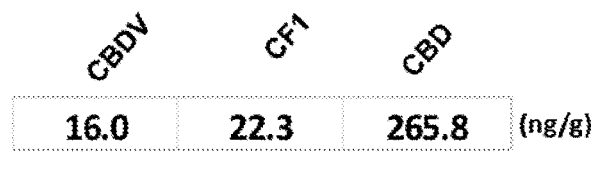
FIGURE 13D
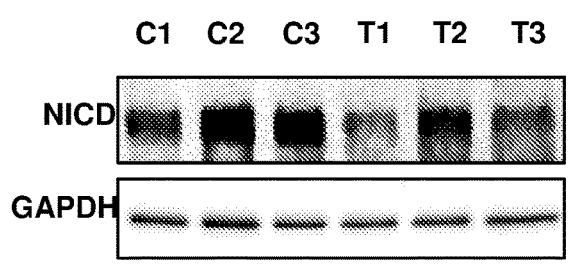
FIGURE 13E
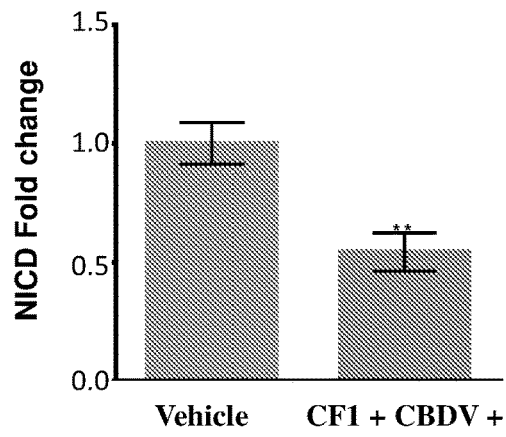
FIGURE 13F

| [% w/w] | Extract 12 | [% w/w] | Extract 12 | [% w/w] | Extract 12 |
|---|---|---|---|---|---|
| CBC | 2.856 | CBGVA | 0.000 | d9-THCVA | 0.000 |
| CBCA | 0.012 | CBL | 0.026 | OH-CBN | 0.003 |
| CBCA-C4 | 0.000 | CBN | 0.118 | OH-CBNA | 0.000 |
| CBC-C4 | 0.023 | CBNA | 0.000 | SesquiCBG | 0.025 |
| CBCMA | 0.004 | CBNA-C4 | 0.000 | SesquiCBGA | 0.000 |
| CBCO | 0.002 | CBN-C4 | 0.000 | CF1 | 2.741 |
| CBCOA | 0.000 | CBND | 0.008 | | |
| CBCV | 0.267 | CBNDA | 0.001 | | |
| CBCVA | 0.002 | CBNDVA | 0.000 | | |
| CBD | 53.384 | CBNM | 0.000 | | |
| CBDA | 1.338 | CBNMA | 0.000 | | |
| CBDA-C4 | 0.006 | CBNO | 0.000 | | |
| CBD-C4 | 0.256 | CBNOA | 0.000 | | |
| CBDM | 0.014 | CBNV | 0.005 | | |
| CBDMA | 0.000 | CBNVA | 0.000 | | |
| CBDO | 0.004 | CBT-1 | 0.065 | | |
| CBDOA | 0.000 | CBT-2 | 0.015 | | |
| CBDV | 2.929 | CBT-3 | 0.047 | | |
| CBDVA | 0.055 | CBTA-1 | 0.000 | | |
| CBE | 0.339 | CBTA-3 | 0.000 | | |
| CBEA | 0.010 | CBTV-1 | 0.004 | | |
| CBEV | 0.014 | CBTV-3 | 0.000 | | |
| CBEVA | 0.001 | d8-THC | 0.014 | | |
| CBG | 0.990 | d9-THC | 1.620 | | |
| CBGA | 0.024 | d9-THCA | 0.000 | | |
| CBGA-C4 | 0.000 | d9-THCA-C4 | 0.000 | | |
| CBG-C4 | 0.002 | d9-THC-C4 | 0.000 | | |
| CBGM | 0.001 | d9-THCM | 0.000 | | |
| CBGMA | 0.000 | d9-THCMA | 0.000 | | |
| CBGO | 0.000 | d9-THCO | 0.000 | | |
| CBGOA | 0.000 | d9-THCOA | 0.000 | | |
| CBGV | 0.008 | d9-THCV | 0.150 | | |

FIGURE 17

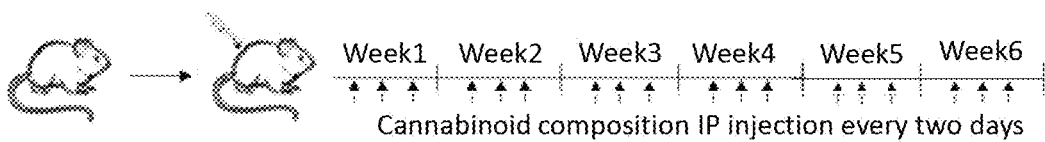

FIGURE 18

SEQUENCE LISTING

<160> NUMBER OF SEQ ID NOS: 8

<210> SEQ ID NO 1
<211> LENGTH: 9568
<212> TYPE: DNA
<213> ORGANISM: Homo sapiens

<400> SEQUENCE: 1

```
actagtgcct cggccgcggg agggagcgca agggcgcggg gcgcggggcg cgggcgcggg      60
cgcgagcgca gcgaaggaac gagccgggcg cggagccggg cccggggggcc tgcgagagca    120 cagcgccgcc agccagccgg ggaagagagg gcgggaccgt ccgccgccgc cccgggaccg    180
tacgccgcgc gtgtgcgtcc cagccccgcc ggccagcgca ggaggccgcc gcccgggcgc    240
agagggcagc cggtggggag gcatgccgcc gctcctggcg cccctgctct gcctggcgct    300
gctgcccgcg ctcgccgcac gaggcccgcg atgctcccag cccggtgaga cctgcctgaa    360
tggcgggaag tgtgaagcgg ccaatggcac ggaggcctgc gtctgtggcg gggccttcgt    420
gggcccgcga tgccaggacc ccaacccgtg cctcagcacc cctgcaaga acgccgggac     480 atgccacgtg gtggaccgca gaggcgtggc agactatgcc tgcagctgtg ccctgggctt    540
ctctgggccc ctctgcctga caccccctgga caatgcctgc ctcaccaacc cctgccgcaa    600 cggggggcacc tgcgacctgc tcacgctgac ggagtacaag tgccgctgcc cgcccggctg    660
gtcagggaaa tcgtgccagc aggctgaccc cgtgcgcctcc aaccccctgcg ccaacggtgg    720 ccagtgcctg cccttcgagg cctcctacat ctgccactgc ccacccagct tccatggccc    780
cacctgccgg caggatgtca acgagtgtgg ccagaagccc gggctttgcc gccacggagg    840
cacctgccac aacgaggtcg gctcctaccg ctgcgtctgc cgcgccaccc acactggccc    900
caactgcgag cggccctacg tgccctgcag ccccctcgccc tgccagaacg ggggcacctg    960
ccgccccacg ggcgacgtca cccacgagtg tgcctgcctg ccaggcttca ccggccagaa   1020
ctgtgaggaa aatatcgacg attgtccagg aaacaactgc aagaacgggg gtgcctgtgt   1080
ggacggcgtg aacacctaca actgccgctg cccgccagag tggacaggtc agtactgtac   1140
cgaggatgtg gacgagtgcc agctgatgcc aaatgcctgc cagaacggcg ggacctgcca   1200
caacacccac ggtggctaca actgcgtgtg tgtcaacggc tggactggtg aggactgcag   1260
cgagaacatt gatgactgtg ccagcgccgc ctgcttccac ggcgccacct gcatgaccg    1320 tgtggcctcc ttctactgcg agtgtcccca tggccgcaca ggtctgctgt gccacctcaa   1380
cgacgcatgc atcagcaacc cctgtaacga gggctccaac tgcgacacca accctgtcaa   1440
tggcaaggcc atctgcacct gccctcgggg gtacacgggc ccggcctgca gccaggacgt   1500
ggatgagtgc tcgctgggtg ccaaccccctg cgagcatgcg ggcaagtgca tcaacacgct   1560
```

-continued

```
gggctccttc gagtgccagt gtctgcaggg ctacacgggc cccgatgcg agatcgacgt    1620 caacgagtgc gtctcgaacc cgtgccagaa cgacgccacc tgcctggacc agattgggga    1680
gttccagtgc atctgcatgc ccggctacga gggtgtgcac tgcgaggtca acacagacga    1740
gtgtgccagc agccctgcc tgcacaatgg ccgctgcctg acaagatca atgagttcca     1800 gtgcgagtgc cccacgggct tcactgggca tctgtgccag tacgatgtgg acgagtgtgc    1860
cagcaccccc tgcaagaatg gtgccaagtg cctggacgga cccaacactt acacctgtgt    1920
gtgcacggaa gggtacacgg ggacgcactg cgaggtggac atcgatgagt gcgaccccga    1980
cccctgccac tacggctcct gcaaggacgg cgtcgccacc ttcacctgcc tctgccgccc    2040
aggctacacg ggccaccact gcgagaccaa catcaacgag tgctccagcc agccctgccg    2100
ccacgggggc acctgccagg accgcgacaa cgcctacctc tgcttctgcc tgaagggac     2160 cacaggaccc aactgcgaga tcaacctgga tgactgtgcc agcagcccct gcgactcggg    2220
cacctgtctg gacaagatcg atggctacga gtgtgcctgt gagccgggct acacagggag    2280
catgtgtaac atcaacatcg atgagtgtgc gggcaacccc tgccacaacg ggggcacctg    2340
cgaggacggc atcaatggct tcacctgccg ctgccccgag ggctaccacg accccacctg    2400
cctgtctgag gtcaatgagt gcaacagcaa cccctgcgtc acggggcct gccgggacag    2460 cctcaacggg tacaagtgcg actgtgaccc tgggtggagt gggaccaact gtgacatcaa    2520
caacaatgag tgtgaatcca acccttgtgt caacggcggc acctgcaaag acatgaccag    2580
tggctacgtg tgcacctgcc gggagggctt cagcggtccc aactgccaga ccaacatcaa    2640
cgagtgtgcg tccaacccat gtctgaacca gggcacgtgt attgacgacg ttgccgggta    2700
caagtgcaac tgcctgctgc cctacacagg tgccacgtgt gaggtggtgc tggccccgtg    2760
tgcccccagc ccctgcagaa acggcgggga gtgcaggcaa tccgaggact atgagagctt    2820
ctcctgtgtc tgccccacgg gctggcaagg gcagacctgt gaggtcgaca tcaacgagtg    2880
cgttctgagc ccgtgccggc acggcgcatc ctgccagaac cccacggcg gctaccgctg     2940 ccactgccag gccggctaca gtgggcgcaa ctgcgagacc gacatcgacg actgccggcc    3000
caacccgtgt cacaacgggg gctcctgcac agacggcatc aacacgggcct tctgcgactg    3060 cctgccggc ttccgggca cttttctgtga ggaggacatc aacgagtgtg ccagtgaccc      3120
ctgccgcaac ggggccaact gcacggactg cgtggacagc tacacgtgca cctgcccgc    3180 aggcttcagc gggatccact gtgagaacaa cacgcctgac tgcacagaga gctcctgctt    3240
caacggtggc acctgcgtgg acggcatcaa ctcgttcacc tgcctgtgtc cacccggctt    3300
cacgggcagc tactgccagc acgatgtcaa tgagtgcgac tcacagccct gcctgcatgg    3360
cggcacctgt caggacggct gcggctccta caggtgcacc tgcccccagg ctacactgg     3420 ccccaactgc cagaaccttg tgcactggtg tgactcctcg ccctgcaaga acggcggcaa    3480
atgctggcag acccacaccc agtaccgctg cgagtgcccc agcggctgga ccggccttta    3540
ctgcgacgtg cccagcgtgt cctgtgaggt ggctgcgcag cgacaaggtg ttgacgttgc    3600
ccgcctgtgc cagcatggag ggctctgtgt ggacgcgggc aacacgcacc actgccgctg    3660
ccaggcgggc tacacaggca gctactgtga ggacctggtg gacgagtgct cacccagccc    3720
ctgccagaac ggggccacct gcacggacta cctgggcggc tactcctgca agtgcgtggc    3780
cggctaccac ggggtgaact gctctgagga gatcgacgag tgcctctccc accctgcca    3840 gaacggggc acctgcctcg acctccccaa cacctacaag tgctcctgcc cacggggcac    3900
```

```
tcagggtgtg cactgtgaga tcaacgtgga cgactgcaat ccccccgttg accccgtgtc    3960
ccggagcccc aagtgcttta acaacggcac ctgcgtggac caggtgggcg gctacagctg    4020
cacctgcccg ccgggcttcg tgggtgagcg ctgtgagggg gatgtcaacg agtgcctgtc    4080
caatccctgc gacgcccgtg gcacccagaa ctgcgtgcag cgcgtcaatg acttccactg    4140
cgagtgccgt gctggtcaca ccgggcgccg ctgcgagtcc gtcatcaatg gctgcaaagg    4200
caagccctgc aagaatgggg gcacctgcgc cgtggcctcc aacaccgccc gcgggttcat    4260
ctgcaagtgc cctgcgggct tcgagggcgc cacgtgtgag aatgacgctc gtacctgcgg    4320
cagcctgcgc tgcctcaacg gcggcacatg catctccggc ccgcgcagcc ccacctgcct    4380
gtgcctgggc cccttcacgg gccccgaatg ccagttcccg ccagcagcc cctgcctggg     4440
cggcaaccccc tgctacaacc aggggacctg tgagcccaca tccgagagcc ccttctaccg    4500
ttgcctgtgc cccgccaaat tcaacgggct cttgtgccac atcctggact acagcttcgg    4560
gggtggggcc gggcgcgaca tcccccgcc gctgatcgag gaggcgtgcg agctgcccga     4620
gtgccaggag gacgcgggca acaaggtctg cagcctgcag tgcaacaacc acgcgtgcgg    4680
ctgggacggc ggtgactgct ccctcaactt caatgacccc tggaagaact gcacgcagtc    4740
tctgcagtgc tggaagtact tcagtgacgg ccactgtgac agccagtgca actcagccgg    4800
ctgcctcttc gacggctttg actgccagcg tgcggaaggc cagtgcaacc ccctgtacga    4860
ccagtactgc aaggaccact tcagcgacgg gcactgcgac cagggctgca acagcgcgga    4920
gtgcgagtgg gacgggctgg actgtgcgga gcatgtaccc gagaggctgg cggccggcac    4980
gctggtggtg tgtgtgctga tgccgccgga gcagctgcgc aacagctcct tccacttcct    5040
gcgggagctc agccgcgtgc tgcacaccaa cgtggtcttc aagcgtgacg cacacggcca    5100
gcagatgatc ttcccctact acggccgcga ggaggagctg cgcaagcacc ccatcaagcg    5160
tgccgccgag ggctgggccg cacctgacgc cctgctgggc caggtgaagg cctcgctgct    5220
ccctggtggc agcgagggtg ggcggcgcg gaggagctg gaccccatgg acgtccgcgg     5280
ctccatcgtc tacctggaga ttgacaaccg gcagtgtgtg caggcctcct cgcagtgctt    5340
ccagagtgcc accgacgtgg ccgcattcct gggagcgctc gcctcgctgg gcagcctcaa    5400
catcccctac aagatcgagg ccgtgcagag tgagaccgtg gagccgcccc cgccggcgca    5460
gctgcacttc atgtacgtgg cggcggccgc ctttgtgctt ctgttcttcg tgggctgcgg    5520
ggtgctgctg tcccgcaagc gccggcggca gcatggccag ctctggttcc ctgagggctt    5580
caaagtgtct gaggccagca agaagaagcg gcgggagccc ctcggcgagg actccgtggg    5640
cctcaagccc ctgaagaacg cttcagacgg tgccctcatg gacgacaacc agaatgagtg    5700
gggggacgag gacctggaga ccaagaagtt ccggttcgag gagcccgtgg ttctgcctga    5760
cctggacgac cagacagacc accggcagtg gactcagcag cacctggatg ccgctgacct    5820
gcgcatgtct gccatggccc ccacaccgcc ccagggtgag gttgacgccg actgcatgga    5880
cgtcaatgtc cgcgggcctg atggcttcac cccgctcatg atcgcctcct gcagcggggg    5940
cggcctggag acgggcaaca gcgaggaaga ggaggacgcg ccggccgtca tctccgactt    6000
catctaccag ggcgccagcc tgcacaacca gacagaccgc acgggcgaga ccgccttgca    6060
cctggccgcc cgctactcac gctctgatgc cgccaagcgc ctgctggagg ccagcgcaga    6120
tgccaacatc caggacaaca tgggccgcac cccgctgcat gcggctgtgt ctgccgacgc    6180
acaaggtgtc ttccagatcc tgatccggaa ccgagccaca gacctggatg cccgcatgca    6240
tgatggcacg acgccactga tcctggctgc ccgcctggcc gtggagggca tgctggagga    6300
```

```
cctcatcaac tcacacgccg acgtcaacgc cgtagatgac ctgggcaagt ccgccctgca   6360
ctgggccgcc gccgtgaaca atgtggatgc cgcagttgtg ctcctgaaga acggggctaa   6420
caaagatatg cagaacaaca gggaggagac acccctgttt ctggccgccc gggagggcag   6480
ctacgagacc gccaaggtgc tgctggacca ctttgccaac cgggacatca cggatcatat   6540
ggaccgcctg ccgcgcgaca tcgcacagga gcgcatgcat cacgacatcg tgaggctgct   6600
ggacgagtac aacctggtgc gcagcccgca gctgcacgga gccccgctgg ggggcacgcc   6660
caccctgtcg cccccgctct gctcgcccaa cggctacctg ggcagcctca gcccggcgt    6720 gcagggcaag aaggtccgca agcccagcag caaaggcctg gcctgtggaa gcaaggaggc   6780
caaggacctc aaggcacgga ggaagaagtc ccaggacggc aagggctgcc tgctggacag   6840
ctccggcatg ctctcgcccg tggactccct ggagtcaccc catggctacc tgtcagacgt   6900
ggcctcgccg ccactgctgc cctccccgtt ccagcagtct ccgtccgtgc ccctcaacca   6960
cctgcctggg atgcccgaca cccacctggg catcgggcac ctgaacgtgg cggccaagcc   7020
cgagatggcg gcgctgggtg ggggcggccg gctggccttt gagactggcc cacctcgtct   7080
ctcccacctg cctgtggcct ctggcaccag caccgtcctg ggctccagca gcggaggggc   7140
cctgaatttc actgtgggcg gtccaccag tttgaatggt caatgcgagt ggctgtcccg    7200
gctgcagagc ggcatggtgc cgaaccaata caaccctctg cggggagtg tggcaccagg    7260 cccctgagc acacaggccc cctccctgca gcatggcatg gtaggccgc tgcacagtag     7320 ccttgctgcc agcgccctgt cccagatgat gagctaccag ggcctgccca gcacccggct   7380
ggccacccag cctcacctgg tgcagaccca gcaggtgcag ccacaaaact acagatgca    7440 gcagcagaac ctgcagccag caaacatcca gcagcagcaa agcctgcagc cgccaccacc   7500
accaccacag ccgcaccttg gcgtgagctc agcagccagc ggccacctgg gccggagctt   7560
cctgagtgga gagccgagcc aggcagacgt gcagccactg ggcccagca gcctggcggt    7620 gcacactatt ctgcccagg agagccccgc cctgcccacg tcgctgccat cctcgctggt    7680
cccacccgtg accgcagccc agttcctgac gccccctcg cagcacagct actcctcgcc    7740
tgtggacaac accccagcc accagctaca ggtgcctgag caccccttcc tcaccccgtc   7800
ccctgagtcc cctgaccagt ggtccagctc gtccccgcat ccaacgtct ccgactggtc    7860 cgagggcgtc tccagccctc ccaccagcat gcagtcccag atcgcccgca ttccggaggc   7920
cttcaagtaa acggcgcgcc ccacgagacc ccggcttcct ttcccaagcc ttcgggcgtc   7980
tgtgtgcgct ctgtggatgc cagggccgac cagaggagcc tttttaaaac acatgttttt   8040
atacaaaata gaacgagga ttttaatttt ttttagtatt tatttatgta cttttatttt     8100
acacagaaac actgccttt tatttatatg tactgtttta tctggcccca ggtagaaact     8160
tttatctatt ctgagaaaac aagcaagttc tgagagccag ggttttccta cgtaggatga   8220
aaagattctt ctgtgtttat aaaatataaa caaagattca tgatttataa atgccattta   8280
tttattgatt cctttttca aaatccaaaa agaaatgatg ttggagaagg gaagttgaac     8340
gagcatagtc caaaaagctc ctggggcgtc caggccgcgc cctttccccg acgcccaccc   8400
aaccccaagc cagcccggcc gctccaccag catcacctgc ctgttaggag aagctgcatc   8460
cagaggcaaa cggaggcaaa gctggctcac cttccgcacg cggattaatt tgcatctgaa   8520
ataggaaaca agtgaaagca tatgggttag atgttgccat gtgttttaga tggtttcttg   8580
caagcatgct tgtgaaaatg tgttctcgga gtgtgtatgc caagagtgca cccatggtac   8640
```

```
caatcatgaa tctttgtttc aggttcagta ttatgtagtt gttcgttggt tatacaagtt    8700
cttggtccct ccagaaccac cccggccccc tgcccgttct tgaaatgtag gcatcatgca    8760
tgtcaaacat gagatgtgtg gactgtggca cttgcctggg tcacacacgg aggcatccta    8820
cccttttctg gggaaagaca ctgcctgggc tgacccggt ggcggcccca gcacctcagc     8880
ctgcacagtg tcccccaggt tccgaagaag atgctccagc aacacagcct gggccccagc    8940
tcgcgggacc cgaccccccg tgggctcccg tgttttgtag gagacttgcc agagccgggc    9000
acattgagct gtgcaacgcc gtgggctgcg tcctttggtc ctgtcccgc agccctggca     9060 gggggcatgc ggtcgggcag gggctggagg gaggcggggg ctgcccttgg gccacccctc    9120
ctagtttggg aggagcagat ttttgcaata ccaagtatag cctatggcag aaaaaatgtc    9180
tgtaaatatg tttttaaagg tggattttgt ttaaaaaatc ttaatgaatg agtctgttgt    9240
gtgtcatgcc agtgagggac gtcagacttg gctcagctcg gggagcctta gccgcccatg    9300
cactggggac gctccgctgc cgtgccgcct gcactcctca gggcagcctc ccccggctct    9360 acggggccg cgtggtgcca tccccagggg gcatgaccaa atgcgtccca agatgttgat      9420
ttttactgtg ttttataaaa tagagtgtag tttacagaaa aagactttaa aagtgatcta    9480
catgaggaac tgtagatgat gtatttttt catctttttt gttaactgat ttgcaataaa     9540
aatgatactg atggtgatct ggcttcca                                       9568
```

<210> SEQ ID NO 2
<211> LENGTH: 2555
<212> TYPE: PRT
<213> ORGANISM: Homo sapiens

<400> SEQUENCE: 2

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

```
Thr His Thr Gly Pro Asn Cys Glu Arg Pro Tyr Val Pro Cys Ser Pro
    210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
    290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
    370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
Cys Glu Ile Asp Val Asn Glu Cys Val Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
            580                 585                 590
Pro Gly Tyr Thr Gly His His Cys Glu Thr Asn Ile Asn Glu Cys Ser
        595                 600                 605
Ser Gln Pro Cys Arg His Gly Gly Thr Cys Gln Asp Arg Asp Asn Ala
    610                 615                 620
Tyr Leu Cys Phe Cys Leu Lys Gly Thr Thr Gly Pro Asn Cys Glu Ile
```

-continued

```
            625                 630                 635                 640
         Asn Leu Asp Asp Cys Ala Ser Ser Pro Cys Asp Ser Gly Thr Cys Leu
                         645                 650                 655

Asp Lys Ile Asp Gly Tyr Glu Cys Ala Cys Glu Pro Gly Tyr Thr Gly
                         660                 665                 670

Ser Met Cys Asn Ile Asn Ile Asp Glu Cys Ala Gly Asn Pro Cys His
                         675                 680                 685

Asn Gly Gly Thr Cys Glu Asp Gly Ile Asn Gly Phe Thr Cys Arg Cys
                         690                 695                 700

Pro Glu Gly Tyr His Asp Pro Thr Cys Leu Ser Glu Val Asn Glu Cys
         705                 710                 715                 720

Asn Ser Asn Pro Cys Val His Gly Ala Cys Arg Asp Ser Leu Asn Gly
                         725                 730                 735

Tyr Lys Cys Asp Cys Asp Pro Gly Trp Ser Gly Thr Asn Cys Asp Ile
                         740                 745                 750

Asn Asn Asn Glu Cys Glu Ser Asn Pro Cys Val Asn Gly Gly Thr Cys
                         755                 760                 765

Lys Asp Met Thr Ser Gly Tyr Val Cys Thr Cys Arg Glu Gly Phe Ser
                         770                 775                 780

Gly Pro Asn Cys Gln Thr Asn Ile Asn Glu Cys Ala Ser Asn Pro Cys
         785                 790                 795                 800

Leu Asn Gln Gly Thr Cys Ile Asp Asp Val Ala Gly Tyr Lys Cys Asn
                         805                 810                 815

Cys Leu Leu Pro Tyr Thr Gly Ala Thr Cys Glu Val Val Leu Ala Pro
                         820                 825                 830

Cys Ala Pro Ser Pro Cys Arg Asn Gly Gly Glu Cys Arg Gln Ser Glu
                         835                 840                 845

Asp Tyr Glu Ser Phe Ser Cys Val Cys Pro Thr Gly Trp Gln Gly Gln
                         850                 855                 860

Thr Cys Glu Val Asp Ile Asn Glu Cys Val Leu Ser Pro Cys Arg His
         865                 870                 875                 880

Gly Ala Ser Cys Gln Asn Thr His Gly Gly Tyr Arg Cys His Cys Gln
                         885                 890                 895

Ala Gly Tyr Ser Gly Arg Asn Cys Glu Thr Asp Ile Asp Asp Cys Arg
                         900                 905                 910

Pro Asn Pro Cys His Asn Gly Gly Ser Cys Thr Asp Gly Ile Asn Thr
                         915                 920                 925

Ala Phe Cys Asp Cys Leu Pro Gly Phe Arg Gly Thr Phe Cys Glu Glu
                         930                 935                 940

Asp Ile Asn Glu Cys Ala Ser Asp Pro Cys Arg Asn Gly Ala Asn Cys
         945                 950                 955                 960

Thr Asp Cys Val Asp Ser Tyr Thr Cys Thr Cys Pro Ala Gly Phe Ser
                         965                 970                 975

Gly Ile His Cys Glu Asn Asn Thr Pro Asp Cys Thr Glu Ser Ser Cys
                         980                 985                 990

Phe Asn Gly Gly Thr Cys Val Asp  Gly Ile Asn Ser Phe Thr Cys Leu
                         995                1000                1005

Cys Pro Pro Gly Phe Thr Gly Ser Tyr Cys Gln His Asp Val Asn
                1010                1015                1020

Glu Cys Asp Ser Gln Pro Cys Leu His Gly Gly Thr Cys Gln Asp
                1025                1030                1035

Gly Cys Gly Ser Tyr Arg Cys Thr Cys Pro Gln Gly Tyr Thr Gly
                1040                1045                1050
```

```
Pro  Asn  Cys  Gln  Asn  Leu  Val  His  Trp  Cys  Asp  Ser  Ser  Pro  Cys
1055                     1060                    1065

Lys  Asn  Gly  Gly  Lys  Cys  Trp  Gln  Thr  His  Thr  Gln  Tyr  Arg  Cys
1070                     1075                    1080

Glu  Cys  Pro  Ser  Gly  Trp  Thr  Gly  Leu  Tyr  Cys  Asp  Val  Pro  Ser
1085                     1090                    1095

Val  Ser  Cys  Glu  Val  Ala  Ala  Gln  Arg  Gln  Gly  Val  Asp  Val  Ala
1100                     1105                    1110

Arg  Leu  Cys  Gln  His  Gly  Gly  Leu  Cys  Val  Asp  Ala  Gly  Asn  Thr
1115                     1120                    1125

His  His  Cys  Arg  Cys  Gln  Ala  Gly  Tyr  Thr  Gly  Ser  Tyr  Cys  Glu
1130                     1135                    1140

Asp  Leu  Val  Asp  Glu  Cys  Ser  Pro  Ser  Pro  Cys  Gln  Asn  Gly  Ala
1145                     1150                    1155

Thr  Cys  Thr  Asp  Tyr  Leu  Gly  Gly  Tyr  Ser  Cys  Lys  Cys  Val  Ala
1160                     1165                    1170

Gly  Tyr  His  Gly  Val  Asn  Cys  Ser  Glu  Glu  Ile  Asp  Glu  Cys  Leu
1175                     1180                    1185

Ser  His  Pro  Cys  Gln  Asn  Gly  Gly  Thr  Cys  Leu  Asp  Leu  Pro  Asn
1190                     1195                    1200

Thr  Tyr  Lys  Cys  Ser  Cys  Pro  Arg  Gly  Thr  Gln  Gly  Val  His  Cys
1205                     1210                    1215

Glu  Ile  Asn  Val  Asp  Asp  Cys  Asn  Pro  Pro  Val  Asp  Pro  Val  Ser
1220                     1225                    1230

Arg  Ser  Pro  Lys  Cys  Phe  Asn  Asn  Gly  Thr  Cys  Val  Asp  Gln  Val
1235                     1240                    1245

Gly  Gly  Tyr  Ser  Cys  Thr  Cys  Pro  Pro  Gly  Phe  Val  Gly  Glu  Arg
1250                     1255                    1260

Cys  Glu  Gly  Asp  Val  Asn  Glu  Cys  Leu  Ser  Asn  Pro  Cys  Asp  Ala
1265                     1270                    1275

Arg  Gly  Thr  Gln  Asn  Cys  Val  Gln  Arg  Val  Asn  Asp  Phe  His  Cys
1280                     1285                    1290

Glu  Cys  Arg  Ala  Gly  His  Thr  Gly  Arg  Arg  Cys  Glu  Ser  Val  Ile
1295                     1300                    1305

Asn  Gly  Cys  Lys  Gly  Lys  Pro  Cys  Lys  Asn  Gly  Gly  Thr  Cys  Ala
1310                     1315                    1320

Val  Ala  Ser  Asn  Thr  Ala  Arg  Gly  Phe  Ile  Cys  Lys  Cys  Pro  Ala
1325                     1330                    1335

Gly  Phe  Glu  Gly  Ala  Thr  Cys  Glu  Asn  Asp  Ala  Arg  Thr  Cys  Gly
1340                     1345                    1350

Ser  Leu  Arg  Cys  Leu  Asn  Gly  Gly  Thr  Cys  Ile  Ser  Gly  Pro  Arg
1355                     1360                    1365

Ser  Pro  Thr  Cys  Leu  Cys  Leu  Gly  Pro  Phe  Thr  Gly  Pro  Glu  Cys
1370                     1375                    1380

Gln  Phe  Pro  Ala  Ser  Ser  Pro  Cys  Leu  Gly  Gly  Asn  Pro  Cys  Tyr
1385                     1390                    1395

Asn  Gln  Gly  Thr  Cys  Glu  Pro  Thr  Ser  Glu  Ser  Pro  Phe  Tyr  Arg
1400                     1405                    1410

Cys  Leu  Cys  Pro  Ala  Lys  Phe  Asn  Gly  Leu  Leu  Cys  His  Ile  Leu
1415                     1420                    1425

Asp  Tyr  Ser  Phe  Gly  Gly  Gly  Ala  Gly  Arg  Asp  Ile  Pro  Pro  Pro
1430                     1435                    1440
```

```
Leu Ile Glu Glu Ala Cys Glu Leu Pro Glu Cys Gln Glu Asp Ala
1445                1450                1455

Gly Asn Lys Val Cys Ser Leu Gln Cys Asn Asn His Ala Cys Gly
1460                1465                1470

Trp Asp Gly Gly Asp Cys Ser Leu Asn Phe Asn Asp Pro Trp Lys
1475                1480                1485

Asn Cys Thr Gln Ser Leu Gln Cys Trp Lys Tyr Phe Ser Asp Gly
1490                1495                1500

His Cys Asp Ser Gln Cys Asn Ser Ala Gly Cys Leu Phe Asp Gly
1505                1510                1515

Phe Asp Cys Gln Arg Ala Glu Gly Gln Cys Asn Pro Leu Tyr Asp
1520                1525                1530

Gln Tyr Cys Lys Asp His Phe Ser Asp Gly His Cys Asp Gln Gly
1535                1540                1545

Cys Asn Ser Ala Glu Cys Glu Trp Asp Gly Leu Asp Cys Ala Glu
1550                1555                1560

His Val Pro Glu Arg Leu Ala Ala Gly Thr Leu Val Val Val Val
1565                1570                1575

Leu Met Pro Pro Glu Gln Leu Arg Asn Ser Ser Phe His Phe Leu
1580                1585                1590

Arg Glu Leu Ser Arg Val Leu His Thr Asn Val Val Phe Lys Arg
1595                1600                1605

Asp Ala His Gly Gln Gln Met Ile Phe Pro Tyr Tyr Gly Arg Glu
1610                1615                1620

Glu Glu Leu Arg Lys His Pro Ile Lys Arg Ala Ala Glu Gly Trp
1625                1630                1635

Ala Ala Pro Asp Ala Leu Leu Gly Gln Val Lys Ala Ser Leu Leu
1640                1645                1650

Pro Gly Gly Ser Glu Gly Gly Arg Arg Arg Arg Glu Leu Asp Pro
1655                1660                1665

Met Asp Val Arg Gly Ser Ile Val Tyr Leu Glu Ile Asp Asn Arg
1670                1675                1680

Gln Cys Val Gln Ala Ser Ser Gln Cys Phe Gln Ser Ala Thr Asp
1685                1690                1695

Val Ala Ala Phe Leu Gly Ala Leu Ala Ser Leu Gly Ser Leu Asn
1700                1705                1710

Ile Pro Tyr Lys Ile Glu Ala Val Gln Ser Glu Thr Val Glu Pro
1715                1720                1725

Pro Pro Pro Ala Gln Leu His Phe Met Tyr Val Ala Ala Ala Ala
1730                1735                1740

Phe Val Leu Leu Phe Phe Val Gly Cys Gly Val Leu Leu Ser Arg
1745                1750                1755

Lys Arg Arg Arg Gln His Gly Gln Leu Trp Phe Pro Glu Gly Phe
1760                1765                1770

Lys Val Ser Glu Ala Ser Lys Lys Arg Arg Glu Pro Leu Gly
1775                1780                1785

Glu Asp Ser Val Gly Leu Lys Pro Leu Lys Asn Ala Ser Asp Gly
1790                1795                1800

Ala Leu Met Asp Asp Asn Gln Asn Glu Trp Gly Asp Glu Asp Leu
1805                1810                1815

Glu Thr Lys Lys Phe Arg Phe Glu Glu Pro Val Val Leu Pro Asp
1820                1825                1830

Leu Asp Asp Gln Thr Asp His Arg Gln Trp Thr Gln Gln His Leu
```

-continued

```
                1835                1840                1845

Asp Ala Ala Asp Leu Arg Met Ser Ala Met Ala Pro Thr Pro Pro
    1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Asp Ala Pro Ala
    1895                1900                1905

Val Ile Ser Asp Phe Ile Tyr Gln Gly Ala Ser Leu His Asn Gln
    1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
    2000                2005                2010

Leu Ile Asn Ser His Ala Asp Val Asn Ala Val Asp Asp Leu Gly
    2015                2020                2025

Lys Ser Ala Leu His Trp Ala Ala Ala Val Asn Asn Val Asp Ala
    2030                2035                2040

Ala Val Val Leu Leu Lys Asn Gly Ala Asn Lys Asp Met Gln Asn
    2045                2050                2055

Asn Arg Glu Glu Thr Pro Leu Phe Leu Ala Ala Arg Glu Gly Ser
    2060                2065                2070

Tyr Glu Thr Ala Lys Val Leu Leu Asp His Phe Ala Asn Arg Asp
    2075                2080                2085

Ile Thr Asp His Met Asp Arg Leu Pro Arg Asp Ile Ala Gln Glu
    2090                2095                2100

Arg Met His His Asp Ile Val Arg Leu Leu Asp Glu Tyr Asn Leu
    2105                2110                2115

Val Arg Ser Pro Gln Leu His Gly Ala Pro Leu Gly Gly Thr Pro
    2120                2125                2130

Thr Leu Ser Pro Pro Leu Cys Ser Pro Asn Gly Tyr Leu Gly Ser
    2135                2140                2145

Leu Lys Pro Gly Val Gln Gly Lys Lys Val Arg Lys Pro Ser Ser
    2150                2155                2160

Lys Gly Leu Ala Cys Gly Ser Lys Glu Ala Lys Asp Leu Lys Ala
    2165                2170                2175

Arg Arg Lys Lys Ser Gln Asp Gly Lys Gly Cys Leu Leu Asp Ser
    2180                2185                2190

Ser Gly Met Leu Ser Pro Val Asp Ser Leu Glu Ser Pro His Gly
    2195                2200                2205

Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro
    2225                2230                2235
```

Asp Thr His Leu Gly Ile Gly His Leu Asn Val Ala Ala Lys Pro
            2240                2245                2250

Glu Met Ala Ala Leu Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Asn Leu Gln Pro Ala Asn Ile Gln
    2390                2395                2400

Gln Gln Gln Ser Leu Gln Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
caccgcaaca tcccctacaa gatcg                                          25

```
<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
aaaccgatct tgtaggggat gttgc                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
caccgtgaag cggccaatgg cacgg                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
aaacccgtgc cattggccgc ttcac                                              25

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
agccgctccg ctgtcctg                                                      18

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
caggacagcg gagcggctc                                                     19
```

CANNABINOIDS AND USES THEREOF

CROSS-REFERENCE TO RELATED APPLICATIONS

This application is the U.S. National Stage of International Patent Application No. PCT/IL2020/050538, filed on May 17, 2020, which claims the benefit of priority of U.S. Provisional Patent Application No. 62/848,695 titled "CANNABINOIDS AND USES THEREOF", filed May 16, 2019, the contents of each of which are incorporated herein by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 36,410 byte ASCII (text) file named "Seq_List" created on May 17, 2020.

FIELD OF INVENTION

The present invention relates to cannabinoid compounds, pharmaceutical compositions comprising same, and method of use thereof.

BACKGROUND

T-cell acute lymphoblastic leukemia (T-ALL) is famous for the amount of molecular irregularities from which it often arises. Most T-ALL-affected individuals harbor genetic mutations or deletions of the oncogenes and tumor suppressor genes NOTCH1, PTEN, NF1, PHF6, PTPN2, IKAROS, and/or FBXW7.

Although T-ALL often arises in the thymus, it spreads throughout the body and, without therapy, is rapidly fatal. Current treatment for T-ALL consists mainly of multi-agent combination chemotherapy. The prognosis of primary resistant and relapsed T-ALL remains very poor.

NOTCH1 pathway is an evolutionarily conserved signaling system that regulates cell proliferation, differentiation, cell-fate determination and self-renewal of stem cells and progenitor cells in both embryonic and adult organs. Notably, both abnormal increases and deficiencies of Notch 1 signaling result in human developmental anomalies and cancer development. Previous attempts to target the Notch1 via a related gamma-secretase inhibitor (GSI), have been unsuccessful.

There is still a great need for pharmaceutical compositions suitable for treating diseases related to NOTCH1 genes and their encoded proteins.

SUMMARY

In some embodiments, the present invention is directed to a method for treating a subject afflicted with a NOTCH1-related disease comprising a step of administering to the subject a composition comprising two or more cannabinoids, selected from: CF1, cannabidiol (CBD) and cannabidivarin (CBDV). Further provided is a pharmaceutical composition comprising CF1, CBD, and CBDV.

According to some embodiments, CF1 is a compound having a structure represented by Formula 1:

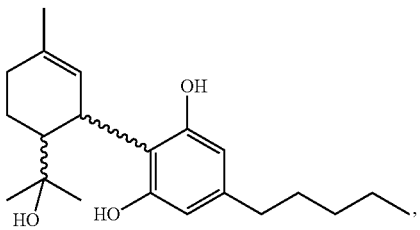 [SMILES: CCCCCc1cc(O)c(C2C=C(C)CCC2C(C)(C)O)c(O)c1]

wherein each wavy bond represents an S-configuration or an R-configuration of a chiral carbon atom.

To date, very little is known about the mechanisms regulating the anti-tumor effect of cannabinoids, and *Cannabis sativa* L. (*Cannabis*) strains for treatment are chosen arbitrarily and generally for palliative oncologic purposes. The findings disclosed herein are based, in part, on the comprehensive analysis of 89 *Cannabis* plant extracts and their phytocannabinoid and/cannabinoid content and show that matching an effective strain (in regard to the phytocannabinoid ratios) to a certain cancerous subtype can enhance the opportunity for personalized cancer treatments and medicines.

According to a first aspect, there is provided a method for treating a subject afflicted with a NOTCH1-related disease, comprising administering to the subject a therapeutically effective amount of a pharmaceutical composition comprising at least two cannabinoids selected from the group consisting of: cannabidiol (CBD), cannabidivarin (CBDV), and CF1, thereby treating a subject afflicted with a NOTCH1-related disease.

According to another aspect, there is provided a pharmaceutical composition comprising CF1, CBD, CBDV, and an acceptable carrier, wherein: (i) the weight per weight (w/w) ratio of CF1 to CBD ranges from 1:1 to 1:1,000; (ii) the w/w ratio of CF1 to CBDV ranges from 1:1 to 1:1,000; and (iii) the w/w ratio of CBDV to CBD ranges from 1:1 to 1:1,000.

In some embodiments, the pharmaceutical composition comprises CBD, CBDV, and CF1. In some embodiments, CF1 and CBD are present in the pharmaceutical composition in a weight per weight (w/w) ratio ranging from 1:1 to 1:1,000. In some embodiments, CBDV and CBD are present in the pharmaceutical composition in a weight per weight (w/w) ratio ranging from 1:1 to 1:1,000. In some embodiments, CF1 and CBDV are present in the pharmaceutical composition in a weight per weight (w/w) ratio ranging from 1:1 to 1:1,000. In some embodiments, CF1, CBD, and CBDV are present in the pharmaceutical composition in a weight per weight (w/w) ratio ranging from 1:1:1 to 1:50:1,000.

In some embodiments, the subject comprises an abnormal expression level of a NOTCH1 protein. In some embodiments, the NOTCH1-related disease is selected from the group consisting of: leukemia, lymphoma, carcinoma, sarcoma, blastoma, and germ cells tumors.

In some embodiments, the NOTCH1-related disease is selected from the group consisting of: T cell acute lymphoblastic leukemia (T-ALL), Chronic lymphocytic leukemia (CLL), Melanoma, Cholangiocarcinoma (CCC), Colorectal cancer, Lung adenocarcinoma, Glioblastoma, Renal cell carcinoma, Ovarian cancer, Prostate cancer, Breast cancer, Pancreatic ductal adenocarcinoma (PDAC), Cervical cancer, Head and neck squamous cell carcinomas (HNSCC), Hepatocellular carcinoma (HCC), Medulloblastoma, B cell acute lymphoblastic leukemia (B-ALL), Acute myeloid leukemia (AML), Small cell lung carcinoma (SCLC), Lung squamous cell carcinoma (SqCC), Cutaneous squamous cell carcinoma (SqCC), and Chronic myelomonocytic leukemia (CMML). In some embodiments, the NOTCH1-related disease is T-ALL.

In some embodiments, the pharmaceutical composition further comprises at least one additional cannabinoid selected from the group consisting of: CBGA, CBG, CBG-C4, CBGV, CBGM, SesquiCBG, THC, $\Delta^8$-THC, THCV, CBDA, CBDA-C4, CBD-C4, CBDVA, CBDO, CBDM, CBCA, CBC, CBC-C4, CBCVA, CBCV, CBCO, CBN, CBNV, OH-CBN, CBEA, CBE, CBEV, CBND, CBNDA, CBL, CBT-1, CBTV-1, CBT-3, and CBT-2. In some embodiments, the pharmaceutical composition further comprises at least one additional cannabinoid selected from the group consisting of: THC, CBDA, and CBG.

In some embodiments, the w/w ratio of CF1, CBD, and CBDV combined to the at least one additional cannabinoid ranges from 10:1 to 100:1. In some embodiments, CF1, CBD, and CBDV combined comprise at least 50% by weight of the cannabinoids of the composition.

In some embodiments, one or more of the cannabinoids is present as a highly purified extract of *Cannabis*.

In some embodiments, one or more of the cannabinoids is a synthetically produced cannabinoid.

In some embodiments, the pharmaceutical composition is for use in the treatment of a NOTCH1-related disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 4 is a table summarizing UHPLC/UV output of sixteen phytocannabinoids percentage quantitation in 19 *Cannabis* extracts.

FIGS. 13A-13F are micrographs and graphs showing that specific cannabinoids combination inhibits tumor growth in-vivo. (13A) Growth curve of tumor volume following vehicle or a composition of the 3 cannabinoids (treatment started after 2 days from cells injection). (13B) Tumor weight analysis of nine xenografts for each treatment (vehicle or a composition of the 3 cannabinoids). Data are presented as mean±SD, (n=9) and statistically analyzed by student t-test. (13C) Representative pictures of tumors following 8 weeks from initiation of treatment. (13D) Quantitation of phytocannabinoids in treated tumors (ng/mL). Quantification was performed using ESI-LC/MS. (13E-13F) are a representative western blot (13E) of NICD from tumors excised from 6 mice treated with either vehicle (C1-C3) or the 3 cannabinoid composition (T1-T3) and GAPDH as a loading control, and (13F) the corresponding quantification analysis (n=3, p<0.01**, student t-test).

FIG. 17 is a table summarizing LC/MS output of quantification of Extract 12.

FIG. 18 is an illustration of a non-limiting timeline of an in-vivo study using specific phytocannabinoids.

DETAILED DESCRIPTION

The present invention provides cannabinoid compounds, cannabinoid compositions, plant extracts comprising cannabinoids, and methods of treating or ameliorating a disease using the described cannabinoid compounds, compositions, and extracts, in a subject in need thereof.

According to some embodiments, the invention is based, in part, on the surprising findings of a specific cannabinoid composition which possess a remarkable antitumor effect on cancer cells such as in NOTCH1-related cancers.

Method of Treatment

According to some embodiments, there is provided a method for treating a subject afflicted with a NOTCH1-related disease, comprising administering to the subject a therapeutically effective amount of a composition comprising at least two cannabinoids selected from: cannabidiol (CBD), cannabidivarin (CBDV), and CF1, thereby treating a subject afflicted with a NOTCH1-related disease.

In some embodiments, the method comprises administering a composition comprising CBD, CBDV, and CF1, wherein CF1 is 1,3-Benzenediol, 2-[(1R,6R)-6-(1-hydroxy-1-methylethyl)-3-methyl-2cyclohexen-1-yl]-5-pentyl.

Cannabinoids and Compositions

In some embodiments, the composition comprises a CF1 cannabinoid. According to some embodiments, CF1 is a compound having a structure represented by Formula 1:

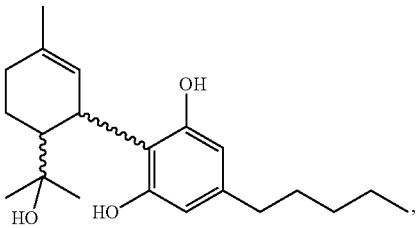 [SMILES: CCCCCc1cc(O)c(C2C=C(C)CCC2C(C)(C)O)c(O)c1]

wherein each wavy bond represents an S-configuration or an R-configuration of a chiral carbon atom. In some embodiments, CF1 is a phytocannabinoid.

Figure 11:
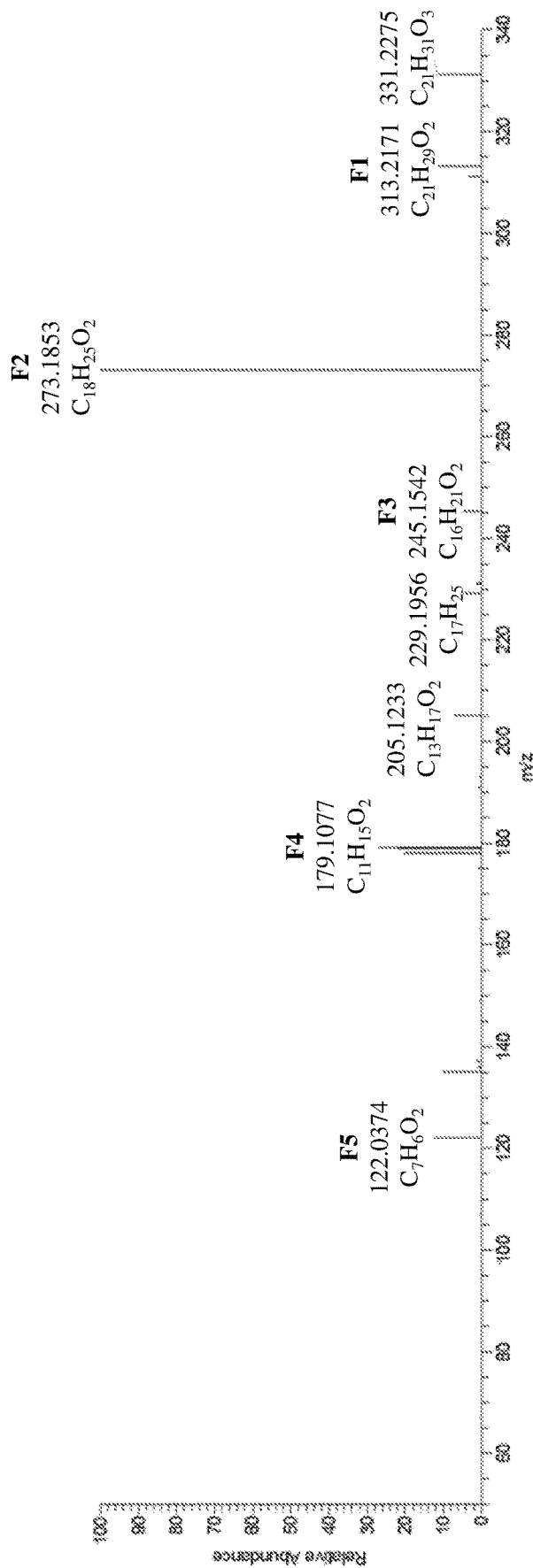
FIG. 11 a tandem mass-spectrometry (MS/MS) spectrum analysis of the identified phytocannabinoid having the formula of Formula 1.

According to some embodiments, CF1 is a compound having a deprotonated accurate mass of 331.227 Da, a retention time of 7.14 min and a MS/MS spectrum shown in FIG. 11. In some embodiments, CF1 is characterized by an accurate mass of 332.2 Da and by a chemical composition $C_{21}H_{32}O_3$. In some embodiments, CF1 is characterized by a retention time of 7.14 minutes when analyzed by UHPLC, under conditions described hereinbelow (see Examples section). In some embodiments, CF1 is a single isomer. In some embodiments, CF1 is a mixture of diastereomers (i.e. RS, RR, SS, SR).

In some embodiments, the herein disclosed cannabinoids composition is used as an anti-cancer agent.

In some embodiments, the cannabinoid is a phytocannabinoid. As used herein, a "phytocannabinoid" is a cannabinoid that originates in nature from the *Cannabis* plant. Examples of cannabinoids include, but are not limited to, CF1, cannabidiol (CBD), cannabidivarin (CBDV), (−)-Δ$^9$-trans-tetrahydrocannabinol (Δ$^9$-THC), (−)-Δ$^9$-trans-tetrahydrocannabinolic acid (Δ$^9$-THCA), (−)-Δ$^9$-trans-tetrahydrocannabivarin (Δ$^9$-THCV), (−)-Δ$^9$-trans-tetrahydrocannabivarinic acid (Δ$^9$-THCVA), cannabinol (CBN), cannabivarin (CBNV), cannabicyclol (CBL), cannabigerol (CBG), cannabigerovarin (CBGV), cannabidiolic acid (CBDA), cannabichromene (CBC), cannabichromenic acid (CBCA) and any derivative thereof.

In some embodiments, the present invention is directed to a composition derived from a plant extract. In some embodiments, a plant extract of the invention is derived from a plant comprising cannabinoids. In some embodiments, the plant extract of the invention is derived from a *Cannabis* plant. In some embodiments, the plant extract is derived from a specific specie of the *Cannabis* genus.

According to some embodiments, the invention relates to a composition comprising a plurality of cannabinoids. In some embodiments, the cannabinoid is selected from: CF1, CBD, and CBDV. In some embodiments, the composition comprises CF1. In some embodiments, the composition comprises CBD. In some embodiments, the composition comprises CBDV.

In some embodiments, the composition comprises CF1 and CBD. In some embodiments, the composition comprises CF1 and CBDV. In some embodiments, the composition comprises CBD and CBDV. In some embodiments, the composition comprises CF1, CBD, and CBDV.

In some embodiments, the composition is a pharmaceutical composition.

In some embodiments, at least 0.1%, 0.5%, 1%, 2%, 3%, 5%, 10%, 20%, 30%, 50%, 70%, 85%, 90%, 99% or 100% of the cannabinoid content of the composition is CF1, or any value and range therebetween. Each possibility represents a separate embodiment of the invention. In some embodiments, the composition comprises at most 0.5%, 1%, 5%, 10%, 25%, 40%, 50%, 60%, 70%, 80%, 90%, 95% or 99% CF1, or any value and range therebetween. Each possibility represents a separate embodiment of the invention.

In some embodiments, at least 1%, 5%, 10%, 20%, 30%, 40%, 50%, 60%, 70%, 80%, 90%, 95%, 99% or 100% of the cannabinoid content of the composition is CBD, or any value and range therebetween. Each possibility represents a separate embodiment of the invention. In some embodiments, the composition comprises at most 1%, 5%, 10%, 20%, 30%, 40%, 50%, 60%, 70%, 80%, 90%, 95% or 99% CBD, or any value and range therebetween. Each possibility represents a separate embodiment of the invention. Each possibility represents a separate embodiment of the invention.

In some embodiments, at least 1%, 5%, 10%, 20%, 30%, 40%, 50%, 60%, 70%, 80%, 90%, 95%, 99% or 100% of the cannabinoid content of the composition is CBDV, or any value and range therebetween. Each possibility represents a separate embodiment of the invention. In some embodiments, the composition comprises at most 1%, 5%, 10%, 20%, 30%, 40%, 50%, 60%, 70%, 80%, 90%, 95% or 99% CBDV, or any value and range therebetween. Each possibility represents a separate embodiment of the invention. Each possibility represents a separate embodiment of the invention.

In some embodiments, CF1, CBD, and CBDV combined, comprise at least 45%, 50%, 60%, 70%, 80%, 85%, 90%, 97%, or 99% by weight, of the total cannabinoids of composition, or any value and range therebetween. Each possibility represents a separate embodiment of the invention. In some embodiments, CF1, CBD, and CBDV combined, comprise at least 45-80%, 50-75%, 60-95%, 70-99%, 80-100%, 50-85%, 60-90%, 68-97%, or 55-99% by weight, of the total cannabinoids of composition. Each possibility represents a separate embodiment of the invention.

In some embodiments, the composition comprises a (i) CF1, CBDV, or both and (ii) CBD weight/weight (w/w) ratio of 1:1 to 1:1,000, 1:5 to 1:500, 1:7 to 1:225, 1:30 to 1:900. In some embodiments, the composition comprises a (i) CF1, CBD, or both, and (ii) CBDV w/w ratio of 1,000:1 to 1:1, 750:1 to 1:750, 500:1 to 1:500, 300:1 to 1:300. In some embodiments, the composition comprises a (i) CBD, CBDV, or both, and (ii) CF1 w/w ratio of 1,000:1 to 1:1, 750:1 to 100:1, 500:1 to 1:1, 300:1 to 1:1.

In some embodiments, the composition comprises a w/w ratio of (i) CF1 and (ii) at least one of CBD, CBDV, or any combination thereof, selected from 1:1 to 1:1,000; 1:1 to 1:500; 1:1 to 800:1; 1:1 to 1:500; 1:1 to 1:300; 1:1 to 1:200; 1:1 to 1:100; 1:1 to 1:50; 1:1 to 1:20; 1:1 to 1:15, wherein each possibility represents a separate embodiment of the invention.

In some embodiments, the composition comprises a w/w ratio of (i) CBD and (ii) at least one of CF1, CBDV, or any combination thereof, selected from 1,000:1 to 100:1; 250:1 to 400:1; 1:1 to 800:1; 1:1 to 350:1; 1:1 to 300:1; 1:1 to 50:1; 1:1 to 70:1; 1:1 to 20:1, wherein each possibility represents a separate embodiment of the invention.

In some embodiments, the composition comprises a w/w ratio of (i) CBDV and (ii) at least one of CF1, CBD, or any combination thereof, selected from 1:1 to 1:1,000; 50:1 to 1:500; 1:1 to 100:1; 1:1 to 1:50; 1:1 to 1:300; 1:1 to 1:250; 1:1 to 1:10; 1:1 to 1:90; 1:1 to 1:20; 1:1 to 1:1.5, wherein each possibility represents a separate embodiment of the invention.

In some embodiments, the w/w/w ratio of CF1 to CBDV to CBD ranges from 1:1:1 to 1:50:1,000. In some embodiments, the w/w/w ratio of CF1 to CBDV to CBD ranges from 1:10:100 to 1:50:2,000. In some embodiments, the w/w/w ratio of CF1 to CBDV to CBD comprises 1:1.4:26.

In some embodiments, the composition comprises a w/w ratio of CF1 to CBD of at least 1:1,000, 1:800, 1:600, 1:400, 1:350, 1:200, 1:100, 1:10, 1:1, or any value and range therebetween. Each possibility represents a separate embodiment of the invention.

In some embodiments, the composition comprises a w/w ratio of CF1 to CBDV of at least 1:1,000, 1:800, 1:600, 1:400, 1:350, 1:200, 1:100, 1:10, 1:1, or any value and range therebetween. Each possibility represents a separate embodiment of the invention.

In some embodiments, the composition comprises a w/w ratio of CBDV to CBD of at least 1:10, 1:20, 1:50, 1:60, 1:150, 1:200, 1:300, 1:500, or any value and range therebetween. Each possibility represents a separate embodiment of the invention. In some embodiments, a composition as described comprises or has w/w ratio of CBDV to CBD of at least 100:1, 50:1, 25:1, 10:1, 5:1, 2:1, or any value and range therebetween. Each possibility represents a separate embodiment of the invention.

In one embodiment, the composition comprises CF1 in an amount selected from 0.1 to 1,000 mg, 0.1 to 100 mg, 0.1 to 10 mg, 100 to 1,000 mg, 10 to 100 mg, 0.1 to 1 mg, 0.01 to 0.1 mg. Each possibility represents a separate embodiment of the invention.

In one embodiment, the composition comprises CBD in an amount selected from 1 to 5,000 mg, 1 to 1,000 mg, 1 to 500 mg, 1 to 100 mg, 1 to 10 mg CBD, 100 to 1,000 mg CBD, 10 to 100 mg, 0.1 to 1 mg, 0.01 to 0.1 mg. Each possibility represents a separate embodiment of the invention.

In one embodiment, the composition comprises CBDV in an amount selected from 1 to 1,000 mg, 1 to 100 mg, 1 to 10 mg, 100 to 1,000 mg, 10 to 100 mg, 0.1 to 1 mg, 0.01 to 1 mg. Each possibility represents a separate embodiment of the invention.

In some embodiments, the cannabinoid is not a psychoactive cannabinoid. In some embodiments, the composition does not comprise a psychoactive cannabinoid.

According to some embodiments, the composition of the invention comprises CBD, CF1, CBDV and at least one additional cannabinoid selected from: CBGA, CBG, CBG-C4, CBGV, CBGM, SesquiCBG, THC (including $\Delta^8$ THC, and/or $\Delta^9$ THC), THCA, THCV (including $\Delta^9$ THCV), THCVA (including $\Delta^9$ THCVA) CBDA, CBDA-C4, CBD-C4, CBDVA, CBDO, CBDM, CBCA, CBC, CBC-C4, CBCVA, CBCMA, CBCV, CBCO, CBN, CBNV, OH-CBN, OH-CBNA, CBEA, CBE, CBEV, CBEVA, CBDVA, CBNDA, CBND, CBL, CBT-1, CBTV-1, CBT-3, CBT-2. Each possibility represents a separate embodiment of the invention.

In some embodiments, the composition comprises CBD, CBDV, CF1 and at least one additional cannabinoid listed in FIG. 17.

According to some embodiments, the composition comprises a plurality of cannabinoids selected from: CBGA, CBG, CBG-C4, CBGV, CBGM, SesquiCBG, THC (including $\Delta^8$ THC, and/or $\Delta^9$ THC), THCA, THCV (such as $\Delta^9$ THCV), THCVA (including $\Delta^9$ THCVA) CBDA, CBDA-C4, CBD-C4, CBDVA, CBDO, CBDM, CBCA, CBC, CBC-C4, CBCVA, CBCMA, CBCV, CBCO, CBN, CBNV, OH-CBN, OH-CBNA, CBEA, CBE, CBEV, CBEVA, CBDVA, CBNDA, CBND, CBL, CBT-1, CBTV-1, CBT-3, CBT-2. Each possibility represents a separate embodiment of the invention.

In some embodiments, THC is or comprises $\Delta^8$-THC. In some embodiments, THC is or comprises $\Delta^9$-THC. In some embodiments, THC is or comprises $\Delta^8$-THC and $\Delta^9$-THC.

In some embodiments, THCV is or comprises $\Delta^9$-THCV.

As used herein, the term "plurality of cannabinoids" refers to two or more cannabinoids, e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, and at least 30, or any value and range therebetween. Each possibility represents a separate embodiment of the invention. In some embodiments, the plurality of cannabinoids of the composition are those having a relative amount of at least 2%, at least 1.5%, at least 1%, at least 0.4%, at least 0.3%, at least 0.2%, at least 0.1%, as described in FIG. 17.

According to some embodiments, the composition of the invention comprises CF1, CBD, CBDV, and at least one additional cannabinoid selected from: CBC, THC, CBDA, CBG, CBE, CBCV, CBD-C4, THCV, CBN and CBT-1. According to some embodiments, the composition of the invention comprises CF1, CBD, CBDV, CBC, THC, CBDA, CBG, CBE, CBCV, CBD-C4, THCV, CBN and CBT-1.

According to some embodiments, the composition of the invention is substantially devoid of at least one cannabinoid selected from: CBGVA, CBGA-C4, CBGA-C1, CBGO, CBGMA, SesquiCBGA, $\Delta^9$-THCA, $\Delta^9$-THCA-C4, $\Delta^9$-THC-C4, $\Delta^9$-THCVA, $\Delta^9$-THCOA, $\Delta^9$-THCO, $\Delta^9$-THCMA, $\Delta^9$-THCM, CBDOA, CBDMA, CBCA-C4, CBCOA, CBNA, CBN-C1, CBNA-C4, CBNA-C1, CBN-C4, CBNVA, OH-CBNA, CBNM, CBNDVA, CBTA-1, CBTA-3, and CBTV-3.

As used herein a composition (e.g. plant extract) that is "substantially devoid" of a cannabinoid refers to a cannabinoid that has a concentration that is less than 1%, 0.5%, 0.05%, 0.005, or 0.0005% of the total cannabinoids' concentration in the composition.

In some embodiments, the composition of the invention comprises at least 0.01%, 0.1%, 0.5%, 1%, 5%, 10%, 20%, 30%, 40%, 50%, 60%, 70%, 80%, 90%, 95%, 99% cannabinoids, or any value and range therebetween. Each possibility represents a separate embodiment of the invention. In some embodiments, the plant extract of the invention comprises at most 0.01%, 0.1%, 0.5%, 1%, 5%, 10%, 20%, 30%, 40%, 50%, 60%, 70%, 80%, 90%, 95%, 99% or 100% cannabinoids, or any value and range therebetween. Each possibility represents a separate embodiment of the invention. In some embodiments, the composition comprises at least 0.001%, 0.01%, 0.1%, 1%, 5%, 10%, 20%, 30%, 40%, 50%, 60%, 70%, 80%, 90%, 95%, 99% CF1, or any value and range therebetween. Each possibility represents a separate embodiment of the invention. In some embodiments, the composition comprises at most 0.1%, 0.5%, 1%, 5%, 10%, 20%, 30%, 40%, 50%, 60%, 70%, 80%, 90%, 95% or 99% CF1, or any value and range therebetween. Each possibility represents a separate embodiment of the invention. In some embodiments, the composition comprises at least 0.001%, 0.01%, 0.1%, 1%, 5%, 10%, 20%, 30%, 40%, 50%, 60%, 70%, 80%, 90%, 95%, 99% CBD, or any value and range therebetween. Each possibility represents a separate embodiment of the invention. In some embodiments, the composition comprises at most 0.1%, 0.5%, 1%, 5%, 10%, 20%, 30%, 40%, 50%, 60%, 70%, 80%, 90%, 95% or 99% CBD, or any value and range therebetween. Each possibility represents a separate embodiment of the invention. In some embodiments, the composition comprises at least 0.001%, 0.01%, 0.1%, 1%, 5%, 10%, 20%, 30%, 40%, 50%, 60%, 70%, 80%, 90%, 95%, 99% CBDV, or any value and range therebetween. Each possibility represents a separate embodiment of the invention. In some embodiments, the composition comprises at most 0.1%, 0.5%, 1%, 5%, 10%, 20%, 30%, 40%, 50%, 60%, 70%, 80%, 90%, 95% or 99% CBDV, or any value and range therebetween. Each possibility represents a separate embodiment of the invention.

According to some embodiments, there is provided a composition consisting essentially of CF1, CBD, and CBDV. In some embodiments, the composition comprises a w/w/w ratio of CF1 to CBDV to CBD ranging from 1:1:1 to 1:50:1,000.

According to some embodiments, there is provided a composition consisting essentially of CF1, CBD, CBDV, THC, CBDA and CBG.

The term "consisting essentially of" denotes that a given compound or substance constitutes the vast majority of the active ingredient's portion or fraction of the composition.

In some embodiments, consisting essentially of means that the combination of CF1, CBD, and CBDV constitute at least 95%, at least 98%, at least 99%, or at least 99.9% by weight, of the active ingredient(s) of the composition, or any value and range therebetween. Each possibility represents a separate embodiment of the invention.

In some embodiments, consisting essentially of means that the combination of CF1, CBD, and CBDV constitute at least 95%, at least 98%, at least 99%, or at least 99.9% by weight, of the total cannabinoids content of the composition.

In some embodiments, consisting essentially of means that the combination of CF1, CBD, and CBDV constitute at least 98%, at least 99%, or at least 99.9% by weight of the active ingredient(s) of the composition, or any value and range there between. Each possibility represents a separate embodiment of the invention.

In some embodiments, consisting essentially of means that the combination of CF1, CBD, and CBDV constitute at least 98%, at least 99%, or at least 99.9% by weight, of the total cannabinoids content of the composition.

In some embodiments, consisting essentially of means that the combination of CF1, CBD, CBDV, THC, CBDA and CBG constitute at least 95%, at least 98%, at least 99%, or at least 99.9% by weight, of the active ingredient(s) of the composition, or any value and range therebetween. Each possibility represents a separate embodiment of the invention.

In some embodiments, consisting essentially of means that the combination of CF1, CBD, CBDV, THC, CBDA and CBG constitute at least 95%, at least 98%, at least 99%, or at least 99.9% by weight, of the total cannabinoids content of the composition.

In some embodiments, consisting essentially of means that the combination of CF1, CBD, CBDV, THC, CBDA and CBG constitute at least 98%, at least 99%, or at least 99.9% by weight of the active ingredient(s) of the composition, or any value and range there between. Each possibility represents a separate embodiment of the invention.

In some embodiments, consisting essentially of means that the combination of CF1, CBD, CBDV, THC, CBDA and CBG constitute at least 98%, at least 99%, or at least 99.9% by weight, of the total cannabinoids content of the composition.

In some embodiments, the composition comprises or consists of a plant extract.

As used herein, the term "extract" comprises the whole extract, a fraction thereof, a portion thereof, an isolated compound therefrom, or any combination thereof.

In some embodiments, the extract is derived from a plant material.

In some embodiments, the plant material is first dried and then extracted. In some embodiments, the plant material is air-dried. In some embodiments, the plant material is further heat treated (e.g., hot-drying) and then extracted.

As used herein, treatment before extraction comprises, for example, freezing, drying, lyophilizing, or any combination thereof.

In some embodiments, the plant material is further processed prior to the extraction procedure in order to facilitate the extraction procedure. In some embodiments, processing methods prior to extraction, include but are not limited to crushing, slicing, or shredding, such as by using a grinder or other devices to fragment the plant parts into small pieces or powder.

In some embodiments, the extraction is a solvent-based extraction. In some embodiments, the solvent is a polar solvent. As used herein, a polar solvent may be selected from the group including, but not limited to, ethanol and Isopropyl. In some embodiments, the solvent is a non-polar solvent. In some embodiments, the extraction is a solventless-based extraction.

According to some embodiments, there is provided a pharmaceutical composition comprising the herein disclosed cannabinoids and a pharmaceutically acceptable carrier.

In some embodiments, the *Cannabis* derived substance used in the composition and methods as described herein includes CF1. In one embodiment, the composition described herein comprises purified or substantially purified (e.g., greater than 80% w/w, 85% w/w, 90%, w/w 95% w/w or 97% w/w) CF1. In some embodiments of the methods described herein, purified or substantially purified (e.g. greater than 80% w/w, 85% w/w, 90%, w/w 95% w/w or 97% w/w) CF1 is administered to a subject suffering from a disease or a condition as described herein.

In one embodiment, the *Cannabis* derived substances used in the composition and methods as described herein include CBD, or a functional variant thereof. In one embodiment, the composition described herein comprises purified or substantially purified (e.g., greater than 80% w/w, 85% w/w, 90%, w/w 95% w/w or 97% w/w) CBD. In some embodiments of the methods described herein, purified or substantially purified (e.g., greater than 80% w/w, 85% w/w, 90%, w/w 95% w/w or 97% w/w) CBD, or a functional variant thereof, is administered to a subject suffering from a disease or a condition as described herein.

In one embodiment, the *Cannabis* derived substances used in the composition and methods as described herein include CBDV, or a functional variant thereof. In one embodiment, the composition described herein comprises purified or substantially purified (e.g., greater than 80% w/w, 85% w/w, 90%, w/w 95% w/w or 97% w/w) CBDV. In some embodiments of the methods described herein, purified or substantially purified (e.g., greater than 80% w/w, 85% w/w, 90%, w/w 95% w/w or 97% w/w) CBDV, or a functional variant thereof, is administered to a subject suffering from a disease or a condition as described herein.

As used herein, the term "synthetic cannabinoids" refers to compounds that have a cannabinoid or cannabinoid-like structure and are manufactured using chemical means rather than by the plant.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier (e.g. carbomer, hydroxypropyl cellulose, sodium lauryl sulfate) as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

A pharmaceutical composition may take any physical form necessary for proper administration. The composition comprising an encapsulated one or more cannabinoid compounds can be administered in any suitable form, including but not limited to a liquid form, a gel form, a semi-liquid (e.g., a liquid, such as a viscous liquid, containing some solid) form, a semi-solid (a solid containing some liquid) form, or a solid form. Compositions can be provided in, for example, a tablet form, a capsule form, a liquid form, a food form a chewable form, a non-chewable form, a transbuccal form, a sublingual form, a slow-release form, a non-slow-release form, a sustained release form, or a non-sustained-release form.

A pharmaceutically-acceptable carrier suitable for the preparation of unit dosage form of a composition as described herein for peroral administration is well-known in the art.

In some embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), stabilizers (e.g. hydroxypropyl cellulose, hydroxypropylmethyl cellulose), viscosity increasing agents(e.g. carbomer, colloidal silicon dioxide, ethyl cellulose, guar gum lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), polymer coatings (e.g., poloxamers or poloxamines), and/or coating and film forming agents (e.g. ethyl cellulose, acrylates, polymethacrylates).

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

NOTCH1-Related Disease

According to some embodiments, there is provided a method for treating a NOTCH1-related disease.

In some embodiments, a NOTCH1 gene or protein is a human NOTCH1 gene or protein.

In some embodiments, a NOTCH1 gene comprises or consists of the nucleic acid sequence set forth in (SEQ ID NO: 1).

In some embodiments, a NOTCH1 protein or polypeptide comprises or consists of the amino acid sequence set forth in (SEQ ID NO: 2).

In some embodiments, the method further comprises a step of determining the expression level of a NOTCH1 protein or a gene encoding same, of the subject.

In some embodiments, the method further comprises a step of determining the presence of a mutation in a NOTCH1-associated gene of the subject.

In some embodiments, the determining step is performed in the subject or in a sample derived or obtained from the subject. In some embodiments, the sample comprises any bodily fluid, cell, tissue, biopsy, organ, or a combination thereof, derived or obtained from the subject. In some embodiments, the determining step is performed in vivo, ex vivo, or in vitro. In some embodiments, any one of ex vivo or in vitro comprises or is in a test tube or in a plate.

As used herein, the terms "administering", "administration", and like terms refer to any method which, in sound medical practice, delivers a composition containing an active agent to a subject in such a manner as to provide a therapeutic effect. One aspect of the present subject matter provides for dermal or transdermal administration of a therapeutically effective amount of a composition of the present subject matter to a patient in need thereof. Other suitable routes of administration can include oral, dermal, transdermal, parenteral, subcutaneous, intravenous, intramuscular, or intraperitoneal. In some embodiments, the administering is systemic administering. In some embodiments, the administering is to the site of inflammation.

Administering the composition to a specific site in the subject may be performed with any method known in the art. This may include with an applicator, in the form of a gel or cream, as well as on a scaffold, wrap or bandage.

As used herein, the terms "treatment" or "treating" of a disease, disorder or condition encompasses alleviation of at least one symptom thereof, a reduction in the severity thereof, or inhibition of the progression thereof. Treatment need not mean that the disease, disorder or condition is totally cured. To be an effective treatment, a useful composition herein needs only to reduce the severity of a disease, disorder, or condition, reduce the severity of symptoms associated therewith, or provide improvement to a patient or subject's quality of life. In some embodiments, alleviated symptoms of the disease, disorder or condition include reduced cell viability, induced cell apoptosis, inhibited cell proliferation, reduced or increased protein expression. In some embodiments, reduced or increased protein expression relates to a NOTCH1 protein, e.g., NOTCH1 and/or a protein encoded by a NOTCH1 gene, e.g., NOTCH1-encoding gene.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described compositions or composition prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, "treating" comprises ameliorating and/or preventing.

As used herein, the term NOTCH1-related disease, refers to any disease, condition, disorder, pathology, or any combination thereof, wherein a NOTCH1 gene or a protein encoded therefrom is involved, induces, initiates, propagates, determines, or any combination or equivalent thereof, in the pathogenesis, pathophysiology, or both.

In some embodiments, a NOTCH1-related disease refers to the onset of cancer in the harmed cell.

As used herein, "cancer" encompasses diseases associated with cell proliferation. Non-limiting types of cancer include, but are not limited to, carcinoma, sarcoma, lymphoma, leukemia, blastoma and germ cells tumors. In one embodiment, carcinoma refers to tumors derived from epithelial cells including, but not limited to breast cancer, prostate cancer melanoma, lung cancer, pancreas cancer, bile duct cancer, colorectal cancer, lung cancer, non-small cell lung carcinoma (NSCLC), skin cancer (melanoma) and colon cancer. In one embodiment, sarcoma refers of tumors derived from mesenchymal cells including but not limited to sarcoma botryoides, chondrosarcoma, Ewing's sarcoma, malignant hemangioendothelioma, malignant schwannoma, osteosarcoma and soft tissue sarcomas. In one embodiment, lymphoma refers to tumors derived from hematopoietic cells that leave the bone marrow and tend to mature in the lymph nodes including but not limited to Hodgkin lymphoma, non-Hodgkin lymphoma, multiple myeloma and immunoproliferative diseases. In one embodiment, leukemia refers to tumors derived from hematopoietic cells that leave the bone marrow and tend to mature in the blood including but not limited to T-cell acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. In one embodiment, blastoma refers to tumors derived from immature precursor cells or embryonic tissue including but not limited to hepatoblastoma, medulloblastoma, nephroblastoma, neuroblastoma, pancreatoblastoma, pleuropulmonary blastoma, retinoblastoma and glioblastoma-multiforme.

In some embodiments, the NOTCH1-associated disease is selected from: T cell acute lymphoblastic leukemia (T-ALL), Chronic lymphocytic leukemia (CLL), Melanoma, Cholangiocarcinoma (CCC), Colorectal cancer, Lung adenocarcinoma, Glioblastoma, Renal cell carcinoma, Ovarian cancer, Prostate cancer, Breast cancer, Pancreatic ductal adenocarcinoma (PDAC), Cervical cancer, Head and neck squamous cell carcinomas (HNSCC), Hepatocellular carcinoma (HCC), Medulloblastoma, B cell acute lymphoblastic leukemia (B-ALL), Acute myeloid leukemia (AML), Small cell lung carcinoma (SCLC), Lung squamous cell carcinoma (SqCC), Cutaneous squamous cell carcinoma (SqCC), and Chronic myelomonocytic leukemia (CMML).

One skilled in the art will appreciate that NOTCH1 receptor functions as ligand-activated transcription factor to directly transduce extracellular signals into changes in gene expression in the nucleus. Each receptor has an N-terminal extracellular (NEC) fragment responsible for interaction with ligands for example from the Delta and Serrate family (e.g. Delta-like 1, 3, and 4; and Jagged 1 and 2). Three Lin12/Notch repeats (LNR) in the NEC fragment fold over a heterodimerization domain (HD), stabilizing and shielding the HD domain in a molecular lock that prevents NOTCH activation in the absence of a ligand. Each receptor also comprises a C-terminal transmembrane-intracellular fragment (NTM) having a single-pass transmembrane domain and a cytoplasmic region which functions as a ligand-activated transcription factor. The intracellular portion of the Notch receptor (termed N1ICD), is translocated into the nucleus to mediate target gene activation. The N1ICD consists of ankyrin repeats, a RAM (RBP-Jk associated molecule) domain, a transactivation domain (TAD), a nuclear localization signal (NLS), and a PEST [proline (P), glutamic acid (E), serine (S), and threonine (T) rich] domain, responsible for terminating NOTCH1 signaling by targeted proteasome degradation of the activated receptor in the nucleus. Each receptor is generated by proteolytic cleavage of a pro-NOTCH1 precursor polypeptide by a furin-like protease in the trans-Golgi network. Triggering of the Notch receptor by ligand-binding promotes two proteolytic cleavage events at the Notch receptor. The first cleavage is catalyzed by the ADAM-family of metalloproteases, whereas the second cleavage is mediated by y-secretase. The second cleavage releases the N1ICD, which is then translocated to the nucleus and acts as a transcriptional coactivator. The N1ICD cannot bind directly to DNA but heterodimerizes with the DNA binding recombination signal sequence-binding protein Jkappa (RBP-J), (also called CSL, CBF1, [Su(H)] and LAG-1) and activates transcription of genes containing RBP-J binding sites such as HES1 and c-Myc. In the absence of a ligand and without nuclear N1ICD, RBP-J represses Notch target genes. Evidence for the involvement of Notch signaling in cancer has been reported for mutation in Notch1 and Notch1 related genes.

According to some embodiments, the subject comprises at least one cell comprising an abnormal expression level of the NOTCH1 protein compared to control cells (e.g. cells having a normal NOTCH1 expression level). In some embodiments, the abnormal expression level relates to increased NOTCH1 protein expression level. In some embodiments the abnormal level of a NOTCH1 protein relates to decreased expression level of a NOTCH1 protein. In some embodiments, the NOTCH1-related disease relates to a mutation in the Notch1 gene. In some embodiments, the NOTCH1-related disease relates to a mutation in a Notch1-associated gene.

Methods for determining NOTCH1 expression are common and would be apparent to one of ordinary skill in the art. Non-limiting examples for methods of determining expression include, but are not limited to, RT-PCR, real time RT-PCR, next generation sequencing, western blot, dot blot, enzyme linked immunosorbent assay (ELISA), and other, some of which are exemplified hereinbelow (in the Example section).

According to some embodiments, a subject afflicted with a NOTCH1-related disease comprises at least one mutation in a NOTCH1 gene. In some embodiments, a mutation is a missense mutation. In some embodiments, a mutation is a nonsense mutation. In some a mutation is a frameshift mutation. In some embodiments, a mutation results in a shorter protein encoded from the mRNA harboring the mutation. In some embodiments, a mutation renders a non-functional protein encoded from an mRNA harboring the mutation.

According to some embodiments, the NOTCH1 gene is or is encoded by SEQ ID NO: 1. According to some embodiments, the NOTCH1 gene encodes a protein or a polypeptide comprising or consisting of SEQ ID NO: 2. According to some embodiments, the mutation is at a NOTCH1 extracellular (NEC) fragment. According to some embodiments, the mutation is at a NOTCH1 transmembrane-intracellular fragment. According to some embodiments, the mutation is at a domain selected from Lin12/ Notch repeat (LNR), heterodimerization domain (HD), intracellular portion of the Notch receptor (N1ICD), ankyrin repeat, RAM domain, TAD domain, NLS, and a PEST.

As used herein, the term "NOTCH1-associated gene", in some embodiments, refers to genes which are activated by NOTCH1. Non-limiting example of genes which are activated by NOTCH1 include, LFNG, SNW1, NFKB1, HIF1A, RBPJ, HEYL, TCFL5, ADAM19, BCL11B, HEY1, HES1, PIN1, NFKB2, ERBB2, FABP7, PPARG, PAX7, C-MYC, HOXA5, BCL2, IL7R, TCF12, CD44, IL2RA. In some embodiments, the term "NOTCH1-associated gene", refers to genes which are inactivated by NOTCH1. Non-limiting example of a gene which is inactivated by NOTCH1 includes TCF3. In some embodiments, the term "NOTCH1-associated gene" refers to genes which activate NOTCH1. Non-limiting examples of genes which activated NOTCH1 include MAML1, MAML2, PSEN1, KAT2B, SNW1, TNF, DLL4, MFNG, GXYLT1, GXYLT2, JAG1, DLL1, DLL3, CTNNB1, DTX1, CNTN6, LFNG, PIN1, RFNG, POGLUT1, LCK, KPNA3, KPNA4, TCF3, DAB1, GSK3B, SMAD3, POFUT1, EIF3F, CCND1, SDC3, SIAH1, KPNA6, DNER, XXYLT1, CSK, FURIN, JAG2, MDM2 and ADAM17. In some embodiments, the term "NOTCH1-associated gene" refers to genes which inactivate NOTCH1. Non-limiting examples of genes which inactivated NOTCH1 include CCNC, FBXW7, SIRT1, GSK3A, CDK8, DLK2, DYRK1A, RUNX2, FOXO3, NUMB, HIF1AN, KAT5, RUNX3, MAPK8IP1, ITCH, NLK, DLK1, HEY2 and YY1.

In some embodiments, the composition of the invention reduces the viability of a cell. In some embodiments, the cell comprises a mutation in a NOTCH1 encoding gene. In some embodiments, the cell is a cell of a subject afflicted with a NOTCH1-related disease. In some embodiments, the cell viability is reduced by at least 5%, 10%, 15%, 20%, 30%, 40%, 50%, 60%, 70%, 80%, 90% or 100% compared to an untreated cell, or any value and range therebetween. Each possibility represents a separate embodiment of the invention. In some embodiments, cell viability reduction is at most 90%, 80%, 70%, 60%, 50%, 40%, 30%, 20% or 10% compared to untreated cells. Each possibility represents a separate embodiment of the invention.

In some embodiments, the composition induces apoptosis of the cell comprising a mutation in a NOTCH1 encoding gene. In some embodiments, the composition of the invention or an extract as disclosed herein induce apoptosis in at least 5%, 10%, 15%, 20%, 30%, 35%, 40%, 45%, 50%, 55%, 60%, 65%, 70%, 75%, 80%, 85%, 90%, 95%, 99% or 100% of the cells, e.g., cells comprising a mutation in a NOTCH1 encoding gene, compared to untreated cells, or any value and range therebetween. Each possibility represents a separate embodiment of the invention.

In some embodiments, the method comprises reducing or increasing the expression level of NOTCH1 and/or NOTCH1-associated gene, or the protein products thereof, in a cell comprising a mutation in a NOTCH1 encoding gene, e.g., a mutation indicative of NOTCH1-related disease in a subject comprising the mutation. In some embodiments, protein expression level is reduced or increased by at least 5%, 10%, 15%, 20%, 30%, 40%, 50%, 60%, 70%, 80%, 90%, 95% or 100% compared to a control, or any value and range therebetween. Each possibility represents a separate embodiment of the invention. In some embodiments, protein expression level of NOTCH1 and/or NOTCH1-associated gene is at most 99%, 90%, 80%, 70%, 60%, 50%, 40%, 30%, 20% or 10% compared to a control. Each possibility represents a separate embodiment of the invention.

In some embodiments, a control is an untreated cell. In some embodiments, a control is the expression of a gene or a protein product thereof, or both, in an untreated cell.

The term "expression" as used herein refers to the biosynthesis of a gene product, including the transcription and/or translation of said gene product. Thus, expression of a nucleic acid molecule may refer to transcription of the nucleic acid fragment (e.g., transcription resulting in mRNA or other functional RNA) and/or translation of RNA into a precursor or mature protein (polypeptide).

In some embodiments, the method comprises inhibiting cell proliferation of a cell comprising a mutation in a NOTCH1 encoding gene.

In some embodiments, the proliferation rate of a cell contacted with the composition of the invention is reduced or inhibited by at least 5%, 10%, 15%, 20%, 30%, 40%, 50%, 60%, 70%, 80%, 90% or 100% compared to a control cell, or any value and range therebetween. Each possibility represents a separate embodiment of the invention.

In some embodiments, compositions for use in the methods of this invention comprise solutions or emulsions, which in some embodiments are aqueous solutions or emulsions comprising a safe and effective amount of the cannabinoids of the present invention and optionally, other compounds as described herein, including excipients intended for topical intranasal administration.

In another embodiment, the composition is administered by intravenous, intra-arterial, or intramuscular injection of a liquid preparation. In some embodiments, liquid formulations include solutions, suspensions, dispersions, emulsions, oils and the like. In one embodiment, the composition is administered intravenously, and is thus formulated in a form suitable for intravenous administration. In another embodiment, the composition is administered intra-arterially, and is thus formulated in a form suitable for intra-arterial administration. In another embodiment, the composition is administered intramuscularly, and is thus formulated in a form suitable for intramuscular administration.

Further, in another embodiment, the composition is administered topically to body surfaces, and is thus formulated in a form suitable for topical administration. Suitable topical formulations include gels, ointments, creams, lotions, drops and the like. For topical administration, the active ingredients disclosed herein, e.g., one or more cannabinoids, are combined with an additional appropriate therapeutic agent or agents, prepared and applied as solutions, suspensions, or emulsions in a physiologically acceptable diluent with or without a pharmaceutical carrier.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, the composition is a suspension, a solution or an emulsion in oily or aqueous vehicle, and contains a suspending, a stabilizing and/or a dispersing agent.

In some embodiments, a composition for parenteral administration includes aqueous solution of the active preparation in water-soluble form. Additionally, suspensions of the active ingredients, in some embodiments, are prepared as appropriate oily or water-based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, the composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, further polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (*Science* 249:1527-1533 (1990).

Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, the amount of a composition to be administered will be dependent on the subject being treated, the severity of the affliction, the manner of administration, the judgment of the prescribing physician, etc.

The dosage administered will be dependent upon the age, health, and weight of the recipient, kind of concurrent treatment, if any, frequency of treatment, and the nature of the effect desired.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range.

Where the stated range includes one or both of the limits, ranges excluding either or both of those included limits are also included in the invention.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Phytocannabinoids Extraction

Air-dried medical *Cannabis* female flowers were ground to a fine powder using an electrical grinder. Several samples were heat-decarboxylated in an oven at 130° C. for 1 h. Approximately 5 g from each chemovar were accurately weighed and extracted with 50 mL HPLC-grade ethanol. Samples were sonicated in an ultrasonic bath for 30 min and then agitated in an orbital shaker at 25° C. for 15 min. Samples were then filtered under pressure through Whatman filter paper number 4 and the ethanol was evaporated under reduced pressure at 38° C. using a rotary evaporator.

Phytocannabinoids Analysis

Liquid chromatography mass spectrometric (LC/MS) grade acetonitrile, methanol, and water for the mobile phase were purchased from Mercury Scientific and Industrial Products Ltd. (Rosh Haayin, Israel). LC/MS grade acetic acid was obtained from Sigma-Aldrich (Rehovot, Israel). The phytocannabinoid analytical standards (>98%) cannabigerol (CBG), $\Delta^9$-THC, CBD, cannabichromene (CBC), cannabinol (CBN), cannabigerolic acid (CBGA), (−)-$\Delta^9$-trans-tetrahydrocannabinolic acid ($\Delta^9$-THCA), cannabidiolic acid (CBDA), cannabinolic acid (CBNA), cannabichromenic acid (CBCA), (−)-$\Delta^8$-trans-tetrahydrocannabinol ($\Delta^8$-THC), (−)-$\Delta^9$-trans-tetrahydrocannabivarin ($\Delta^9$-THCV), cannabidivarin (CBDV), cannabidivarinic acid (CBDVA), and cannabicyclol (CBL) were purchased from Sigma-Aldrich (Rehovot, Israel); cannabichromevarin (CBCV) and cannabicitran were purchased from Cayman Chemical (Ann Arbor, MI, US).

Phytocannabinoids analysis for the compounds with analytical standards was performed by reversed phase ultra-high-performance liquid chromatography with an ultraviolet detector (UHPLC/UV, Thermo Scientific, Bremen, Germany). The chromatographic separation was achieved using a HALO C18 Fused-Core column (2.7 μm, 150×2.1 mm i.d.), with a HALO guard column (2.1×5 mm, 2.7 μm), and a ternary A/B/C multistep gradient (solvent A: 0.1% acetic acid in water, solvent B: 0.1% acetic acid in acetonitrile, and solvent C: methanol). The multistep gradient program was established as follows: initial conditions were 50% B raised to 67% B until 3 min, held at 67% B for 5 min, and then raised to 90% B until 12 min, held at 90% B until 15 min, decreased to 50% B over the next min, and held at 50% B until 20 min for re-equilibration of the system prior to the next injection. Solvent C was initially 5% and then lowered to 3% until 3 min, held at 3% until 8 min, raised to 5% until 12 min and then kept constant at 5% throughout the run. A flow rate of 0.25 mL/min was used, the column temperature was 30° C. and the injection volume was 1 μL. Data acquisition was performed in full UV-Vis scan mode. Standard mixes in DMSO were prepared ranging from 1 to 1,000 μg/mL for $\Delta^9$-THCA, $\Delta^9$-THC, CBDA and CBD, and 0.25 to 250 μg/mL for all the other components. Cannabis extracts were injected to the UHPLC/UV in a concentration of 1 mg/ml.

Comprehensive phytocannabinoid analysis was performed using a similar UHPLC system coupled to a Q Exactive™ Focus Hybrid Quadrupole-Orbitrap MS (Thermo Scientific, Bremen, Germany) and a similar chromatographic method as previously described. MS acquisition was carried out with a heated electro spray ionization (HESI-II) ion source operated in negative mode. Source parameters were as follows: sheath gas flow rate, auxiliary gas flow rate and sweep gas flow rate: 50, 20 and 0 arbitrary units respectively; capillary temperature: 350° C.; heater temperature: 50° C.; spray voltage: 3.00 kV. The scan range was 150-550 m/z for all acquisition events. MS was operated in full MS1 mode at 70,000 resolution, and the AGC target was set to 106 with a maximum IT of 100 ms. Identification and absolute quantification of phytocannabinoids was performed by external calibrations as described by Berman et al. (2018).

Absolute quantification of phytocannabinoids with analytical standards was performed by external calibrations. Standard mixes were prepared ranging from 1 to 1000 ng/mL for $\Delta^9$-THCA, $\Delta^9$-THC, CBDA and CBD, and 0.25 to 625 ng/mL for all the other components. The dynamic range for each component was determined as maximum deviation from expected concentrations of 20%, and minimum signal-to-noise ratios of 10. All other phytocannabinoids without analytical standards were semi-quantified according to calibration curves from the same phytocannabinoid family or average curves for unknown compounds (Berman et al., 2018). Due to a large variation in concentrations of phytocannabinoids in Cannabis strains, all samples were injected and analyzed by LC/MS in three concentrations (10, 1 and 0.1 μg/mL Cannabis extract to ethanol).

Cell Cultures

Four well-characterized human T-Cell acute lymphoblastic Leukemia cell lines were purchased from ATCC and used in this research: Loucy (CRL-2629™), CCRF-CEM(CCL-119™) and Molt-4 (CRL-1582™). Jurkat acute T-cell leukemia cells were a kind gift from Prof. Yoram Reiter at the Technion, Israel Institute of Technology. Jurkat, Loucy, CCRF-CEM and Molt-4 cells were grown in 1640 medium (Sigma-Aldrich, R8758) supplemented with 10% FBS (Biological Industries, 04-007-1A) and 100 units/ml of penicillin G and 100 μg/mL of streptomycin (Biological Industries, 03-031-1B). All cells were maintained in a humidified atmosphere of 5% $CO_2$ at 37° C.

Cell Viability Assay

Cells were cultured in 96-well plates. At 100,000 cells/well the media was replaced with RPMI containing 0.5% FBS and different Cannabis extracts. Extracts were added in triplicate at a concentration of 1-5 μg/mL. DMSO was used as the control and applied in the same amount as in the diluted extracts. An alamarBlue® reagent was used to quantitate viability (according to the manufacturer's Instructions). Viability was measured following 24 h of incubation using fluorescence spectrophotometry at excitation and emission wavelengths of 560 and 590 nm, respectively. Viability was calculated as percent reduction between treated and control cells.

Cell Apoptosis Assay

Cells were cultured and incubated for 24 h in 12-well plates, at 1,000,000 cells/well with media containing 0.5% FBS, and Cannabis extracts or DMSO (control) at a concentration of 1-5 Apoptotic cells were detected by an Annexin V/PI assay using flow cytometry, or via detection of cleaved caspase-3 using a western blot assay as described below.

Annexin V/PI Assay

Apoptosis was assessed by Annexin V-FITC (BioVision, 1006-200) and propidium iodide (PI) staining in annexin binding buffer (BioVision, 1006-100) according to the manufacturer's instructions. Apoptosis assessed by flow cytometry used a BD™ LSR II digital four-laser flow cytometer (BD Biosciences) and was analyzed by BD FACSDiva™ software version 6.1.2. (BD Biosciences). Results were calculated as percentage of positive Annexin V-FITC cells out of total cells counted (30,000 events).

CRISPR/Cas9-Mediated Genome-Editing in Cell Lines

A guide RNA (gRNA) sequence was cloned into lentiCRISPR-v2 plasmid (Addgene) according to a published protocol (Sanjana et al., 2014) Cell lines were infected with guide using lentivirus particles and Polybrene transfection reagent (Merck). 24 hr post infection, puromycin (typically at 1 mg/mL) was added to enrich positively infected cells. The puromycin selection typically lasted for 2 days, until mock-infected, control cells were completely eliminated by puromycin.

Single CRISPR: For this experiment the inventors used gRNA sequences that targeted the first coding exon downstream to the first ATG start site. The sequences used were: Notch1 gRNA1: 5' CACCGCAACATCCCCTACAA-GATCG 3' (SEQ ID NO: 3), 5' AAACCGATCTTGTAGGG-GATGTTGC 3' (SEQ ID NO: 4); Notch1 gRNA2: 5' CACCGTGAAGCGGCCAATGGCACGG 3' (SEQ ID NO: 5), 5' AAACCCGTGCCATTGGCCGCTTCAC 3' (SEQ ID NO: 6). For control the inventors used gRNA without a target sequence in the human genome. The sequences were: Cont gRNA—5' AGCCGCTCCGCTGTCCTG 3' (SEQ ID NO: 7), 5' CAGGACAGCGGAGCGGCTC 3' (SEQ ID NO: 8).

Cell Lysis and Western Blot Analyses

Following treatment, cells were solubilized in radioimmunoprecipitation assay buffer (RIPA) (Sigma-Aldrich, R0278) and the protein concentration in lysates were determined using a Bradford reagent (Sigma-Aldrich, B6916). Equal amounts of protein were resolved by Novex™ 4-20% Tris-Glycine Mini Gels (Thermo Fisher Scientific, XP04200BOX) and electrophoretically transferred to a nitrocellulose membrane (Bio-Rad, 1704159S). Membranes were blocked with TBS 0.1% Tween 20 buffer containing 5% bovine serum albumin (Sigma, A7906) for 1 h. The blots were then incubated overnight at 4° C. with Full Notch1 (Millipure ABS90), from Cell Signaling Technology Notch1 V1744 (4147S), c-Myc (13987), Hes1 (11988), anti-cleaved caspase-3 antibody (9664), Phospho-C-Jun (3270), C-Jun (9165), and β-tubulin (clone D3U1W, 86298) and Chac1 (ab76386) from abcam. This was followed by incubation with horseradish peroxidase-labeled matching secondary antibodies. Immunoreactive bands were detected by Luminata™ HRP substrate (Millipore, WBLUR0500) and visualized using a MicroChemi imager (DNR Bioimaging Systems).

RNA Extraction

Total RNA was isolated from cells (1,000,000 cells/sample) using Trizol® (Thermo Fisher Scientific, 15596026) and RNeasy kit (Qiagen, 74104) according to the manufacturer instructions. Sample quality was assessed by both spectrophotometer (Nanodrop Technologies®) and agarose gels (1%).

Real-Time Quantitative PCR cDNA was synthesized from 1 µg of RNA. Purified RNA was reverse transcribed with the gScript™ cDNA synthesis kit (Quanta Biosciences, 95047) according to the manufacturer's instructions. The mRNA expression levels of human Notch1 (Hs01062014_ml) and Chac1 (Hs00225520_ml) were quantified using TaqMan® Gene Expression assays (Applied Biosystems, 4448892) and a quantitative-PCR 7300 system (Applied Biosystems). Relative expression values were normalized using an endogenous housekeeping gene GAPDH (Hs02758991_g1) as the control and calculated using standard A-Ct methods.

RNA Seq

Molt-4 cells (1,000,000 cells/treatment) treated with DMSO (control) or *Cannabis* extract for 3 h were lysed in Trizol® (Thermo Fisher Scientific) and RNeasy kit (Qiagen) according to the manufacturer's instructions. The analysis was performed with an Affymetrix Clariom-S microarray for human genome RNA expression, by the genomic services in the Hebrew University of Jerusalem.

Notch1 Activity Luciferase RBP-Jk Reporter Assay

This assay was performed using a Cignal Lenti RBP-Jk Reporter (luc) kit (Qiagen Cat: CLS-014L-8). Molt-4 and CCRF-CEM cells were transduced with lentivirus particles with 0.8 µg/mL of PB overnight. One day following the virus infection, the fresh medium was replaced with 1 µg/mL puromycin for selection. Following establishment of stable line expressing reporter gene cassette, 1,000,000 cells/well were incubated in media containing 0.5% FBS and *Cannabis* extract or DMSO (control) at a concentration of 5 µg/mL for 3 h. Luciferase was detected with Promega ONE-Glo™ EX Luciferase Assay System (#E8110) used according to the manufacturer's instructions.

N1ICD Overexpression plasmid 3×FlagNICD1 was inserted to Molt-4 cells using an Amaxa™ 4D-Nucleofector™ system according to the manufacturer's instructions.

Phytocannabinoids Single Molecule Fractionation

Preliminary fractionations of *Cannabis* Extract 12 were performed using semi-preparative high-performance liquid chromatography with an ultraviolet detector (semi-preparative HPLC/UV, Thermo Scientific, Bremen, Germany). The chromatographic separation was achieved using a Luna® C18 column (10 250 mm×21.1 mm i.d.) and a two solvent A/B multistep gradient (solvent A: 0.1% acetic acid in water and solvent B: 0.1% acetic acid in acetonitrile). All solvents were HPLC grade. The multistep gradient program was established as follows: initial conditions were 50% B for 4 min, raised to 76% B until 6.5 min, held at 76% B for 16.5 min, and then raised to 90% B until 26 min, held at 90% B until 31 min, decreased to 50% B over the next 4 min, and held at 50% B until 40 min for re-equilibration of the system prior to the next injection. A flow rate of 20 mL/min and an injection volume of 500-750 µL were used. Data acquisition was performed at 220 nm. The crude *Cannabis* extract was prepared in a concentration of 100 mg/ml in ethanol. The collected fractions were lyophilized to dryness.

In order to improve the yield and purity of the fractions, a preliminary separation step was employed prior to semi-preparative HPLC fractionation. The crude *Cannabis* extract was dissolved to a concentration of 0.5 g/mL in ethanol, filtered using a PTFE 0.45 µm filter, and then purified using a PLC 2050 Purification System, equipped with a centrifugal partition chromatography (CPC)-250 column and a photodiode array (PDA) detector (Gilson Inc.). Separations were achieved using a biphasic solvent system consisting of upper (hexane:acetonitrile in the ratio of 98:2 v/v) and mobile (acetonitrile:water in the ratio 50:50 v/v) phases in descending (DSC) mode. The column was operated with a flow rate of 12.5 mL/min and a rotation speed of 2,200 rpm. The gradient program was established as follows: initial conditions were acetonitrile:water:hexane in the ratio 50:50:0 v/v for 25 min, and then gradually raised to acetonitrile:water:hexane in the ratio 64:34:1 v/v until 45 min. The collected fractions were lyophilized to dryness and further subjected to semi-preparative HPLC fractionation as previously described.

Structure Elucidation of CF1 via Nuclear Magnetic Resonance (NMR)

The structure of the isolated CF1 was further elucidated via $^1$H and $^{13}$C NMR using a Bruker Avance-III-700 spectrometer (700.5 and 176.1 for 1H and 13C nuclear MHz, respectively). CBD as a reference and the isolated CF1 were dissolved in $CDCl_3$ and analyzed at 5° C. with TMS as the internal reference.

T-ALL Xenograft Studies

NOD.CB17-Prkdcscid/NCrHsd mice, 5-7 weeks old, were purchased from envigo and maintained in our facilities. NSG mice, 5-7 weeks old, were purchased from the Technion animal facility. All mice were housed in controlled environments in plastic flexible film gnotobiotic isolators with HEPA filters under a strict 14 h light/10 h dark cycle, and with access to sterilized water and food ad libitum. All treatments were in accordance with the Technion Animal Care and Use Committee guidelines (IL_047-03-2017).

For the in vivo tumorigenesis assay, Molt-4 cells mixed with matrigel (1:1) were injected subcutaneously into the flanks of 7-weeks old female NOD.CB17-Prkdcscid/NCrHsd mice. The tumors' size (length and width) were measured every 3 days with a caliper, and the tumor volume was determined according to the formula: volume=length·(width)$^2$.0.5. To investigate the inhibitory effects of *Cannabis* extracts on tumorigenesis, mice were intraperitoneally injected with 150 mg/kg *Cannabis* extract to mouse weight every two days, starting two or fourteen days after cells injections. The mice were euthanized at the indicated days or whenever the allowable endpoint size (1 cm$^3$) was reached. None of the xenograft tumors reached the maximal tumor volume permitted by the Technion Animal Care and Use Committee guidelines. At the end of the experiment, the xenograft tumors were dissected and weighed.

For the in vivo leukemogenesis assay, 7-weeks old female NSG mice were intravenously injected with CCRF-CEM cells. To investigate the inhibitory effects of *Cannabis* extracts on leukemogenesis, mice were intraperitoneally injected with 150 mg/kg *Cannabis* extract to mouse weight every two days, starting two days after cells injections. The mice were euthanized after the indicated days. The bone marrow (BM) was harvested from each mouse and infiltrated CCRF to BM were identified by staining for human CD45 antibody.

Phytocannabinoids Analysis from Tumor Tissue

Fresh excised tumors were accurately weighed and dissected to smaller sections. HBSS (Sigma-Aldrich #H8264) was added in a ratio of 1 mL per 100 mg sample. The samples were further homogenized into single-cell suspensions using a gentleMACS™ Dissociator using a pre-set program for tumor tissue and stored in −80° C. until further extraction.

The extraction solution (methanol:acetonitrile:acetic acid in the ratio 50:50:0.1 v/v) spiked with 20 ng/mL of a CBD-d3 internal standard (Sigma-Aldrich, Rehovot, Israel) was added to the single cell suspensions in the ratio 3:1 v/v, respectively. Samples were thoroughly vortexed and then centrifuged for 20 min at 4° C. for protein and cell precipitation. The supernatants were then mixed in a ratio of 1:3 v/v sample to 0.1% v/v acetic acid in water and loaded onto Agela Cleanert C8 solid phase extraction (SPE) cartridges (500 mg of sorbent, 50 µm particle size). Phytocannabinoids were eluted from the columns using 2 mL of 0.1% v/v acetic acid in methanol, evaporated to dryness by speedvac, and reconstituted in 100 µL ethanol.

CBD, CBDV and CF1 were analyzed using the same LC/MS system, with similar chromatographic and MS parameters as those previously described. Identification of the three phytocannabinoids was performed by retention time, accurate mass, and spectral matching against the developed LC/MS/MS library of phytocannabinoids (Berman et al., 2018). Absolute quantification of CBD and CBDV was performed by the stable isotope dilution method. CF1 was semi-quantified according to the calibration curve of CBD.

Immunofluorescence

Tumors were fixed in 10% formalin and embedded in paraffin. Sections (3 µm) were obtained for immunofluorescence. After deparaffinization and rehydration, antigen retrieval was performed by boiling in citrate buffer (pH 6) for 10 min. Sections were incubated with 3% BSA/0.1% Triton/PBS for 1 h at room temperature, and incubated with primary antibodies overnight at 4° C. [Notch1 V1744 (4147S)]. After washing with 0.1% Triton/PBS, the appropriate fluorochrome-conjugated secondary antibodies (Alexa Fluor 488-labeled goat anti-rabbit Ig, Jackson ImmunoResearch-111-545-003) were added for 1 h. Sections were washed, and nuclei were counterstained with DAPI. After washing with PBS, sections were mounted with Fluoromount-G (Life Technologies, 00-4958-02) on a coverslip, and images were acquired using a confocal microscope (Leica, SP5) with a ×20 lens. All the presented images are representative of >10 random fields.

Statistical Analysis

All the statistical analyses were conducted using GraphPad Prism software version 7.04. Data are reported as the mean±SEM of at least three independent experiments. Multiple groups were compared using one-way or two-way ANOVA followed by Bonferroni post-hoc multiple comparisons test. A threshold p value of ≤0.05 was considered statistically significant (*p<0.05, p<0.005 and *p<0.0005).

Example 1

The Heterogenous Composition of *Cannabis* Extracts

Figure 1:
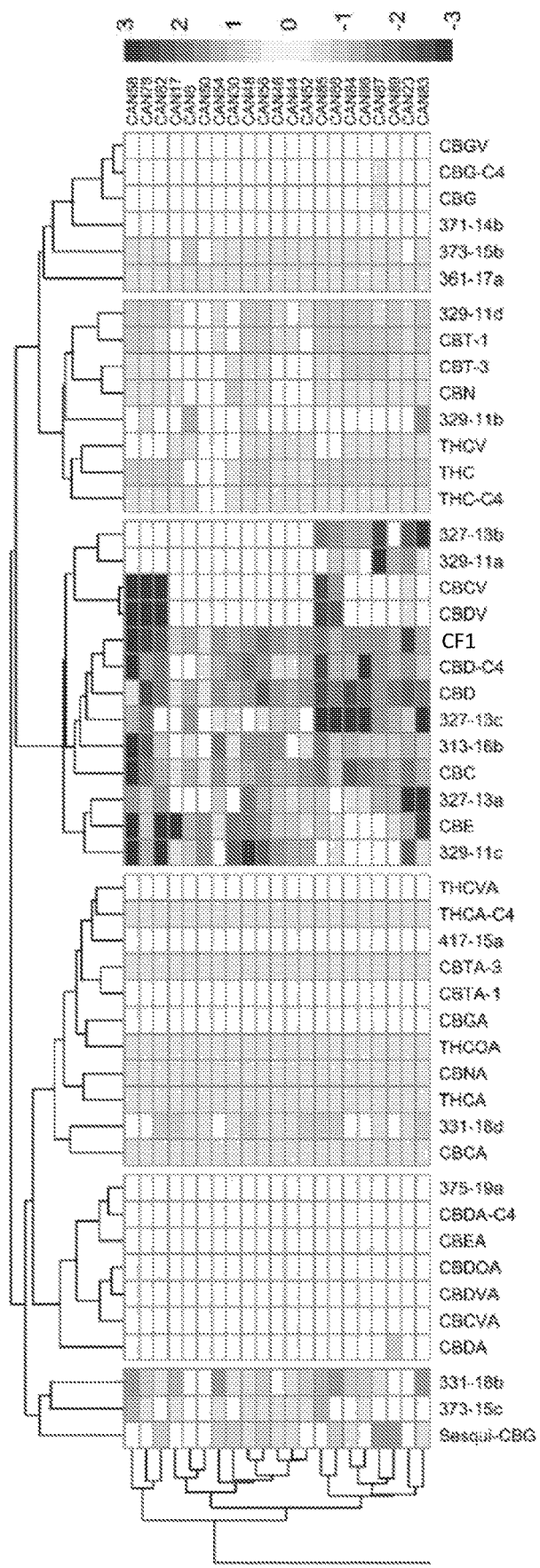
FIG. 1 is a z-score heat map of the 89 *Cannabis* extracts analyzed in this study via electrospray ionization liquid chromatography mass spectrometry (ESI-LC/MS) organized according to hierarchical clustering of both *Cannabis* samples and phytocannabinoid contents. Data is presented as average ±SEM of at least three different experiments, each conducted in triplicates. The criteria for phytocannabinoid inclusion include detection of at least three extracts and a minimum concentration of 0.1% w/w in one of the studied extracts. Columns are labelled by phytocannabinoid name. Rows are labelled with extract names. Five visible clusters (clusters1-5) can be observed which can be traced back to the major phytocannabinoid types in each group. Color scale indicates the darker the red, the larger the amount of phytocannabinoid per extract.
Figure 1:
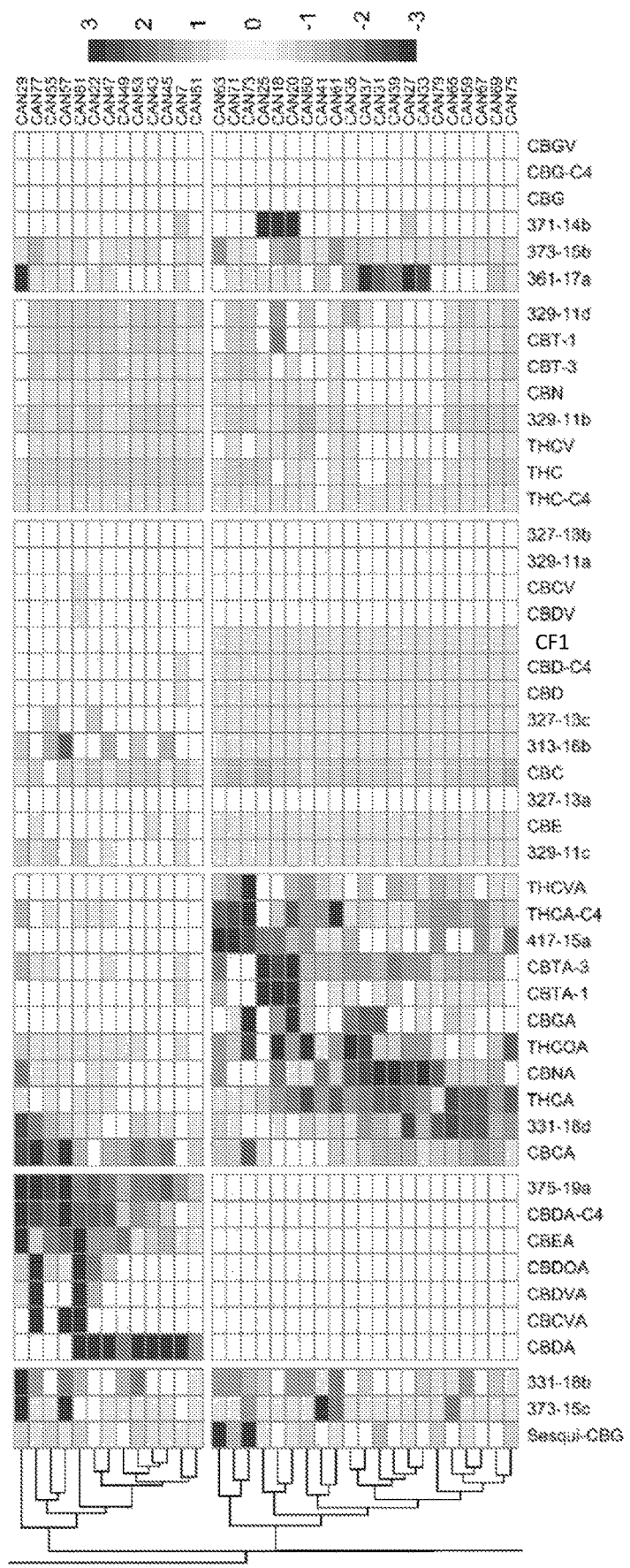
Figure 1:
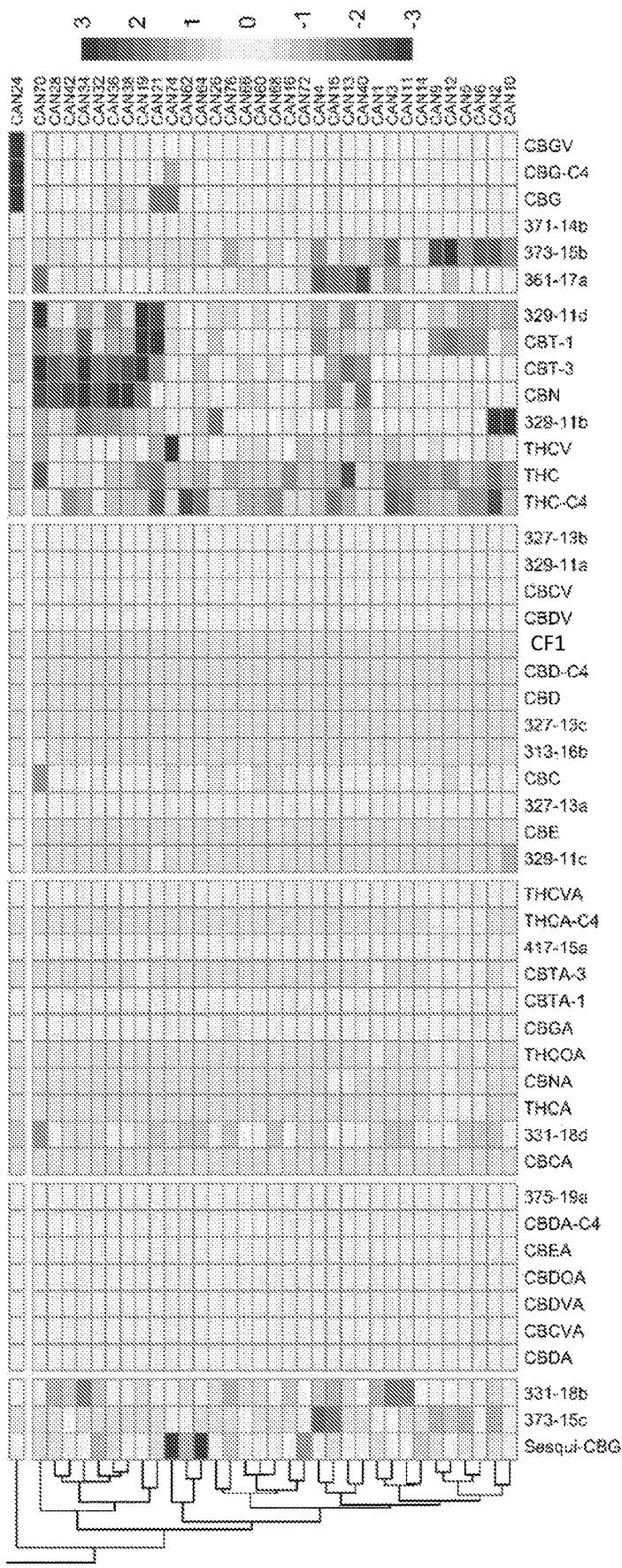

Phytocannabinoid analyses of 89 *Cannabis* extracts (CAN1-89) were performed by applying electrospray ionization liquid chromatography mass spectrometry (ESI/LC/MS). 88 phytocannabinoids were observed in these extracts, of which 45 are presented in FIG. 1. Hierarchical clustering of the corresponding z-score matrix of association showed several major clusters which can be characterized by patterns of phytocannabinoid compositions. According to this hierarchical clustering, minor phytocannabinoid constituents could also contribute significantly to the ability to differentiate among *Cannabis* extracts. 15 representative *Cannabis* extracts having high-$\Delta^9$-THC concentration, high-CBD concentration, or of differing $\Delta^9$-THC:CBD ratios were chosen (Extracts 1-15) from the major clusters.

Example 2

Identifying Notch1 Expression in Cancer Cells

Figure 2A:
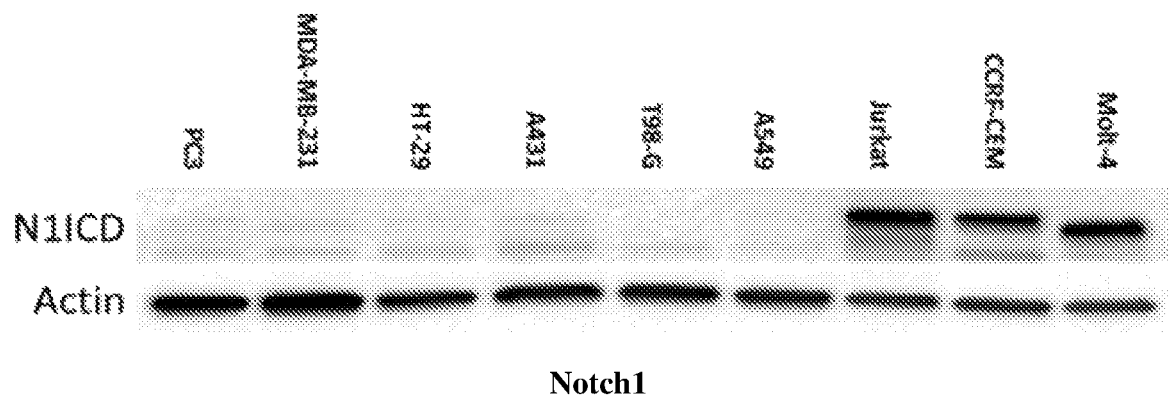
FIGS. 2A-2B are a micrograph (2A) of a western blot analysis and a vertical bar graph (2B) showing the expression of NOTCH1 gene and Notch1 protein in various cancer cell lines. (2A) The protein expression of N1ICD protein in a panel of cancer cell lines PC3, MDA-MB-231, HT-29, A431, T98-G, A549, Jurkat, CCRF-CEM, and MOLT-4 was evaluated by western blot (n=2). Protein samples (50 µg) were separated by 10% SDS-PAGE. β-Actin was used as a loading control and labelled as DMSO. (2B) mRNA expression of the NOTCH1 gene was estimated by real-time PCR (n=2). GAPDH was used as a normalization control for quantifying the target gene expression. Columns indicate mean values.
Figure 2B:
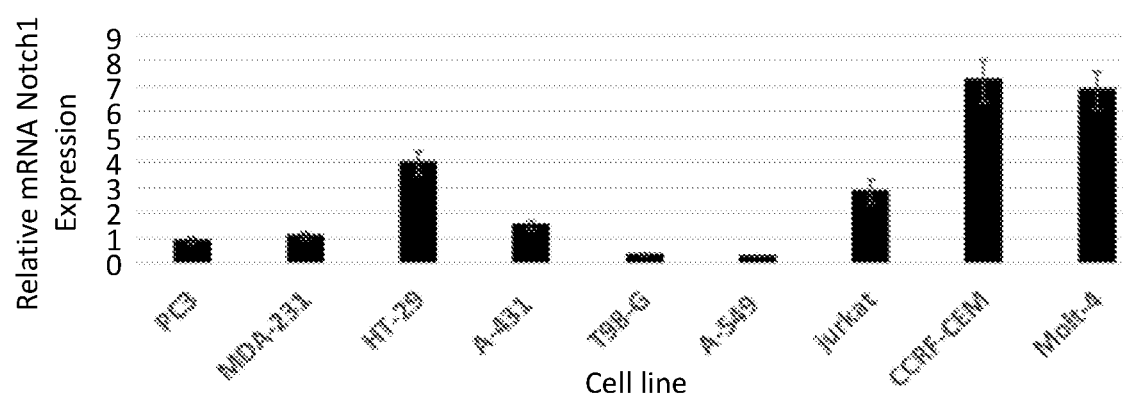

To quantify Notch 1 protein and mRNA expression in various cancer cell lines, two types of analyses were performed: western blot to investigate the protein expression of Notch1 (N1ICD) and qPCR to analyze the mRNA expression of NOTCH1 (FIG. 2). Nine human cancer cell lines which are well-characterized and established by the American Type Culture Collection (ATCC) were chosen: A549 for lung carcinoma; A-431 for skin cancer; PC3 for prostate carcinoma; HT29 for colorectal adenocarcinoma; MDA-231 for breast carcinoma; T98G for glioblastoma; and Jurkat, CCRF-CEM and MOLT-4 for acute T-cell leukemia. As illustrated in FIG. 2B the, mRNA expression of the Notch 1 protein varied among cell lines. Both the western blot (FIG. 2A) and qPCR (FIG. 2B) results corresponded in FIG. 2 to show that Notch 1 protein and mRNA expression were highest in the Jurkat, MOLT-4 and CCRF-CEM cell-lines. Jurkat cells possess a wild type (WT) NOTCH1 gene but contain a mutation in the E3 ligase-FBXW7, a gene which regulates the stability of the intracellular NOTCH1. MOLT-4 and the CCRF-CEM cells contain a mutation in the HD domain of NOTCH1 which causes constitutive activity of the intracellular NOTCH1. In addition, the same methods were applied to the T-ALL leukemic cell line Loucy, which also represents WT NOTCH1 activity.

Example 3

Differential Effects of *Cannabis* Extracts on Cell Viability and Apoptosis

Figure 3A:
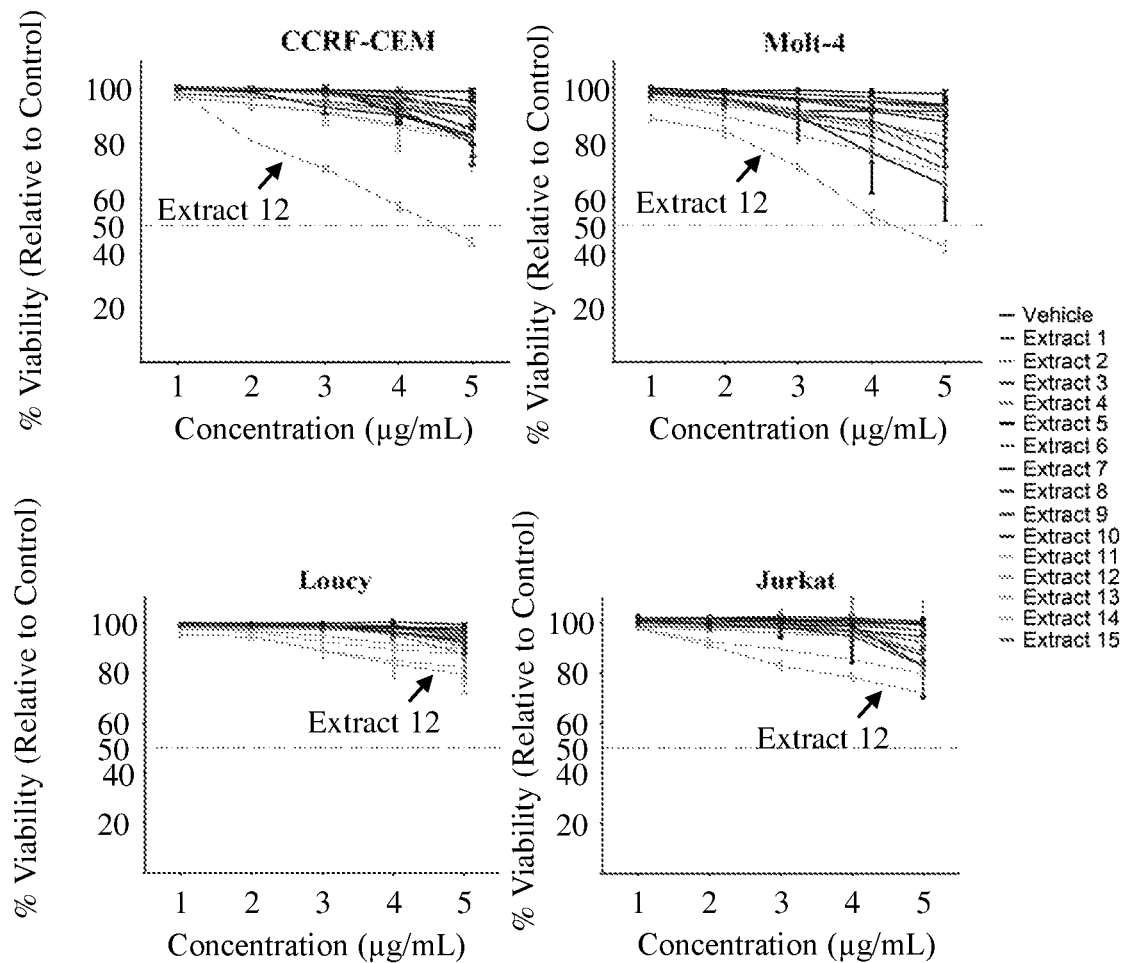
FIGS. 3A-3B are graphs showing dose-dependent effects of *Cannabis* extracts on cell viability. (3A) *Cannabis* Extract 12 reduces viability of NOTCH-1 mutated T-ALL cell lines (indicated by an arrow). AlamarBlue® viability assay performed on Loucy, Jurkat, CCRF-CEM and MOLT-4 cell lines after 24 h application of 15 *Cannabis* strain extracts (Extracts 1-15, 1 to 5 µg/mL) (n=3, p<0.001). (3B) AlamarBlue® viability assays preformed with 5 CBD-rich strains (Extract 12 and Extracts 16-19) on Loucy, Jurkat, CCRF-CEM and MOLT-4 cell lines at concentrations of 1 to 5 µg/mL in triplicate for 24 h. Cell death rates were determined by emission signals, normalized to those of carrier control-treated cells, and expressed as mean±SD (errors bars) of 3 replicates. Statistical significance (*p<0.05, p<0.01, *p<0.001, ****p<0.0001) was determined by Two-way ANOVA using Bonferroni's correction for multiple comparison testing. *Cannabis* Extract 12 was shown to be highly effective in reducing viability of NOTCH-1 mutated T-ALL cell lines (indicated by an arrow in 3A-3B).

In order to examine the mechanism of *Cannabis*-associated cell death, the capacity of the 15 *Cannabis* extracts to induce apoptosis in the four chosen cancer cell lines (Loucy, Jurkat, MOLT-4 and CCRF-CEM cell-lines) was tested. An AlamarBlue® viability assay revealed that among the 15 extracts that were examined, only Extract 12 (CAN85 in FIG. 1), a high CBD and low $\Delta^9$-THC extract, reduced the viability of all 4 cell lines (FIG. 3A, phytocannabinoid concentrations according to UHPLC/UV appear in FIG. 4).

Figure 3B:
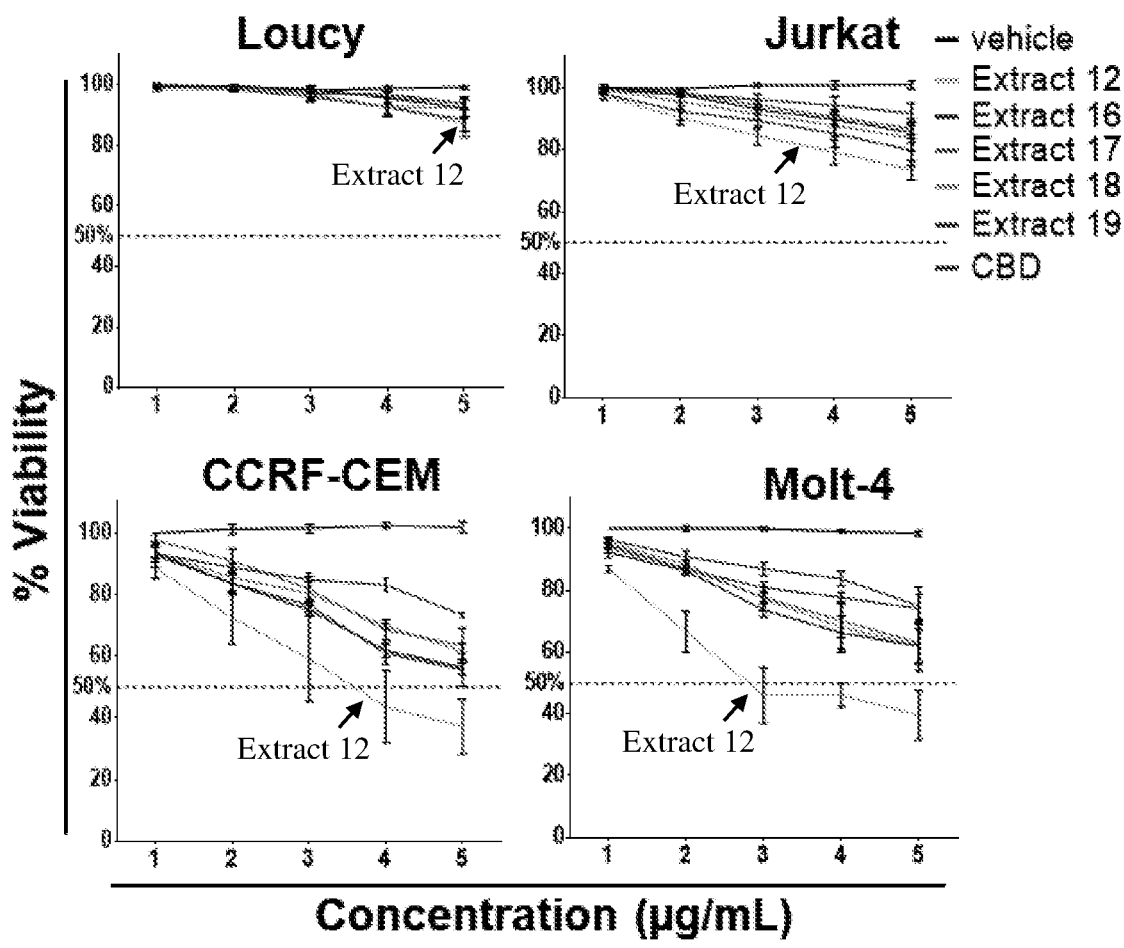

Next, Extract 12 was compared to other high CBD strains (FIG. 4). As seen in FIG. 3B, Extract 12 was the most potent in decreasing viability of both MOLT-4 and CCRF-CEM cell lines (p>0.001). Therefore, these results indicate that it is probably not just the CBD which acts as the main component to produce Extract 12 effects on reducing viability in MOLT-4 and CCRF-CEM cell lines.

Example 4

Figure 5A:
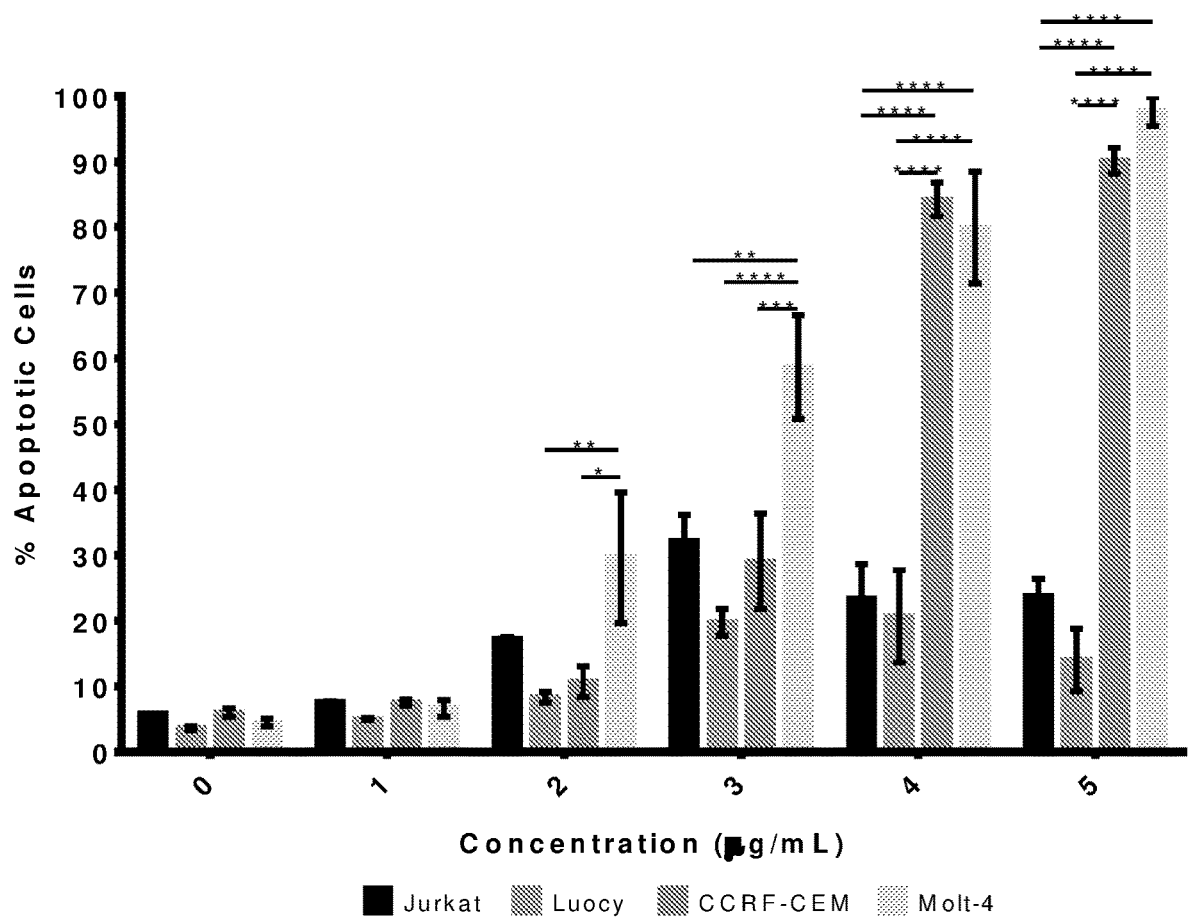
FIG. 5A-5C are graphs and a western blot analysis showing that *Cannabis* Extract 12 decreases cellular viability and induces apoptosis in acute lymphoblastic leukemia (T-ALL) cell lines. (5A) A vertical bar graph showing that *Cannabis* Extract 12 induces apoptosis of NOTCH/-mutated cells. Annexin-V assay performed on Loucy, Jurkat, CCRF-CEM and MOLT-4 cell lines after 24 h application of Extract 12 (1 to 5 µg/mL) (n=3, *p<0.05, p<0.01, *p<0.001, ****p<0.0001) was determined by Two-way ANOVA using Bonferroni's correction for multiple comparison testing. (5B) Representative flow cytometry dot blot of Molt-4 and Jurkat after treatment with vehicle or Extract 12 (5 µg/mL) for 24 h. (5C) Representative blot of cleaved caspase 3 (C. Caspase 3) after treatment with vehicle/Extract 12 (5 µg/mL) for 3 h in T-ALL cell lines.
Figure 5B:
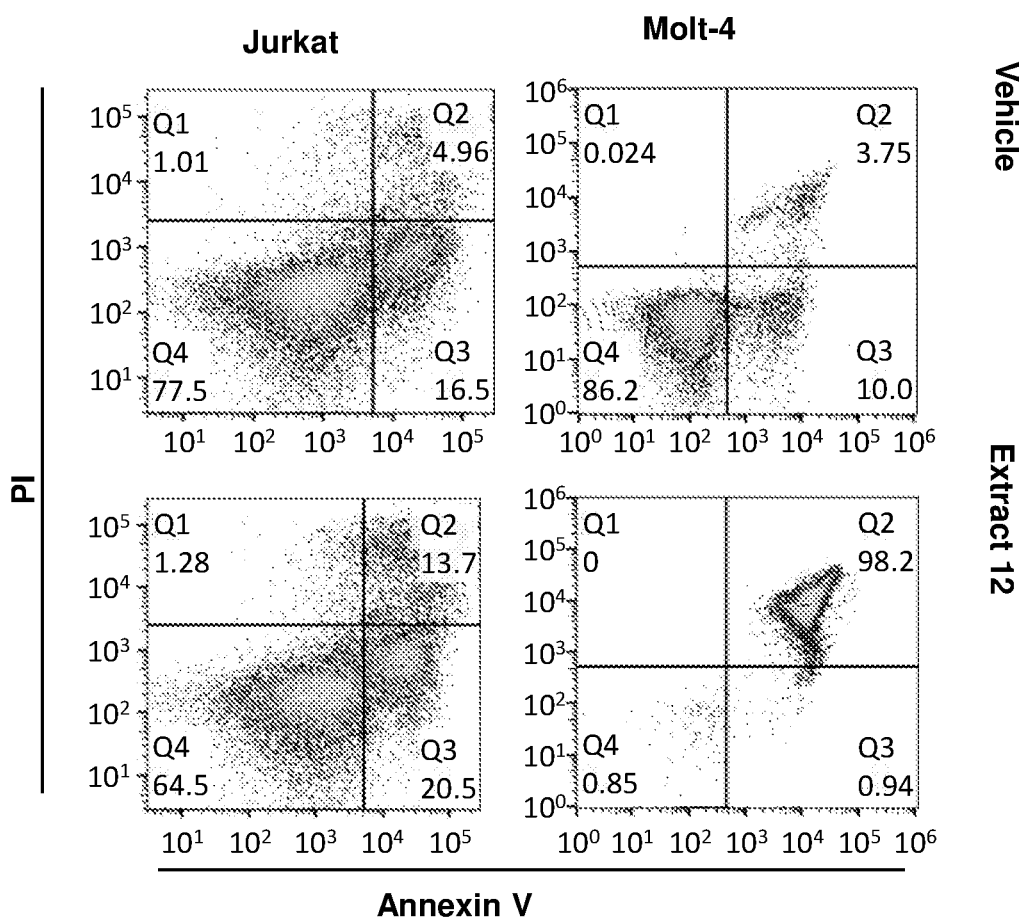
Figure 5C:
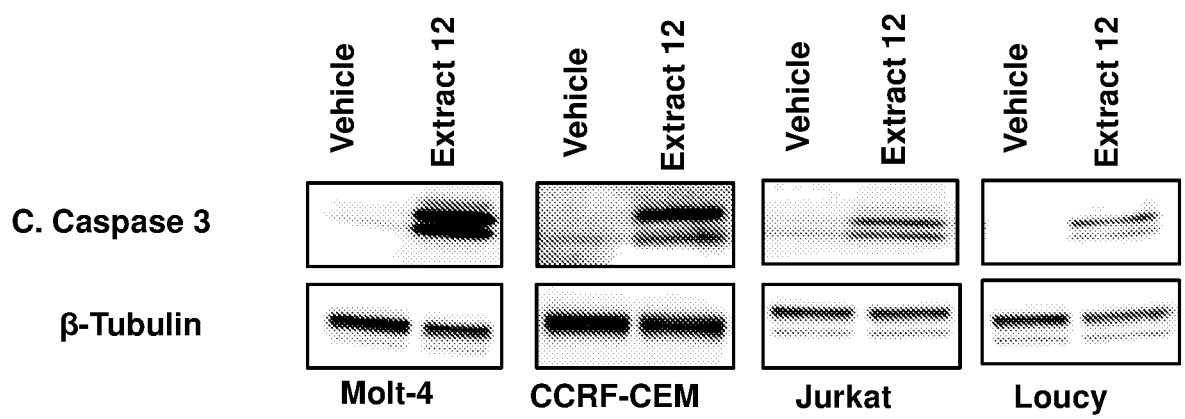

Antitumoral Effects of *Cannabis* Extract 12 in T-cell Acute Lymphoblastic Leukemia Cell Lines In order to understand if the reduction in T-ALL cell viability results from apoptosis, the inventors treated T-ALL cells with different concentrations of Extract 12 for 24 h and measured apoptosis with an Annexin V/PI staining assay (FIG. 5A). The results show that treatment with *Cannabis* extracts leads to significantly more apoptosis of CCRF-CEM and Molt-4 compared to Jurkat or Loucy cells in a dose dependent manner (FIG. 5B). The inventors further assessed caspase3 cleavage by western blot analysis and the induction of cleaved caspase3 following incubation with *Cannabis* Extract 12 confirmed apoptosis (FIG. 5C).

Example 5

*Cannabis* Extract 12 Effects Notch1 Signaling in T-ALL Cell Lines

Figure 6B:
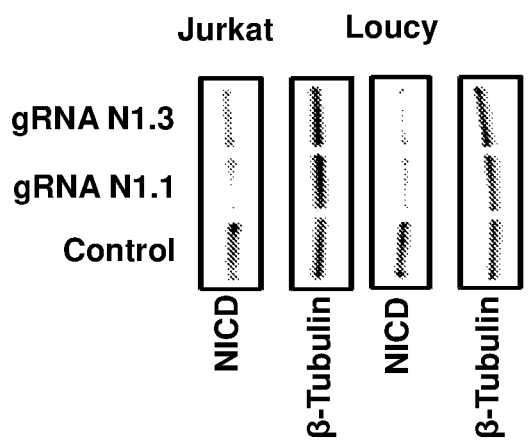
FIGS. 6A-6C are vertical bar graphs and a micrograph of a western blot analysis. (6A) Notch1 mRNA expression in T-ALL cell lines. (6B) Notch1 CRISPR knockout (KO) in Jurkat and Loucy cell lines. Representative blot of NICD after KO. (6C) Representative flow cytometry dot blot after Notch1 KO (MOLT-4, CCRF-CEM, Jurkat and Loucy cell lines).
Figure 6A:
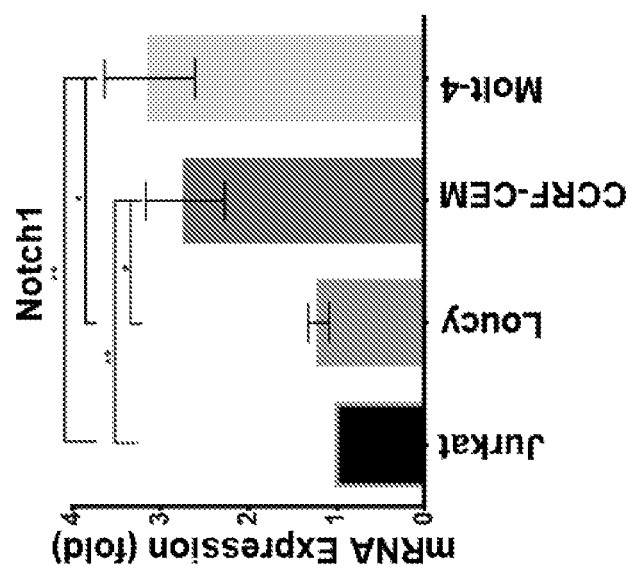
Figure 6C:
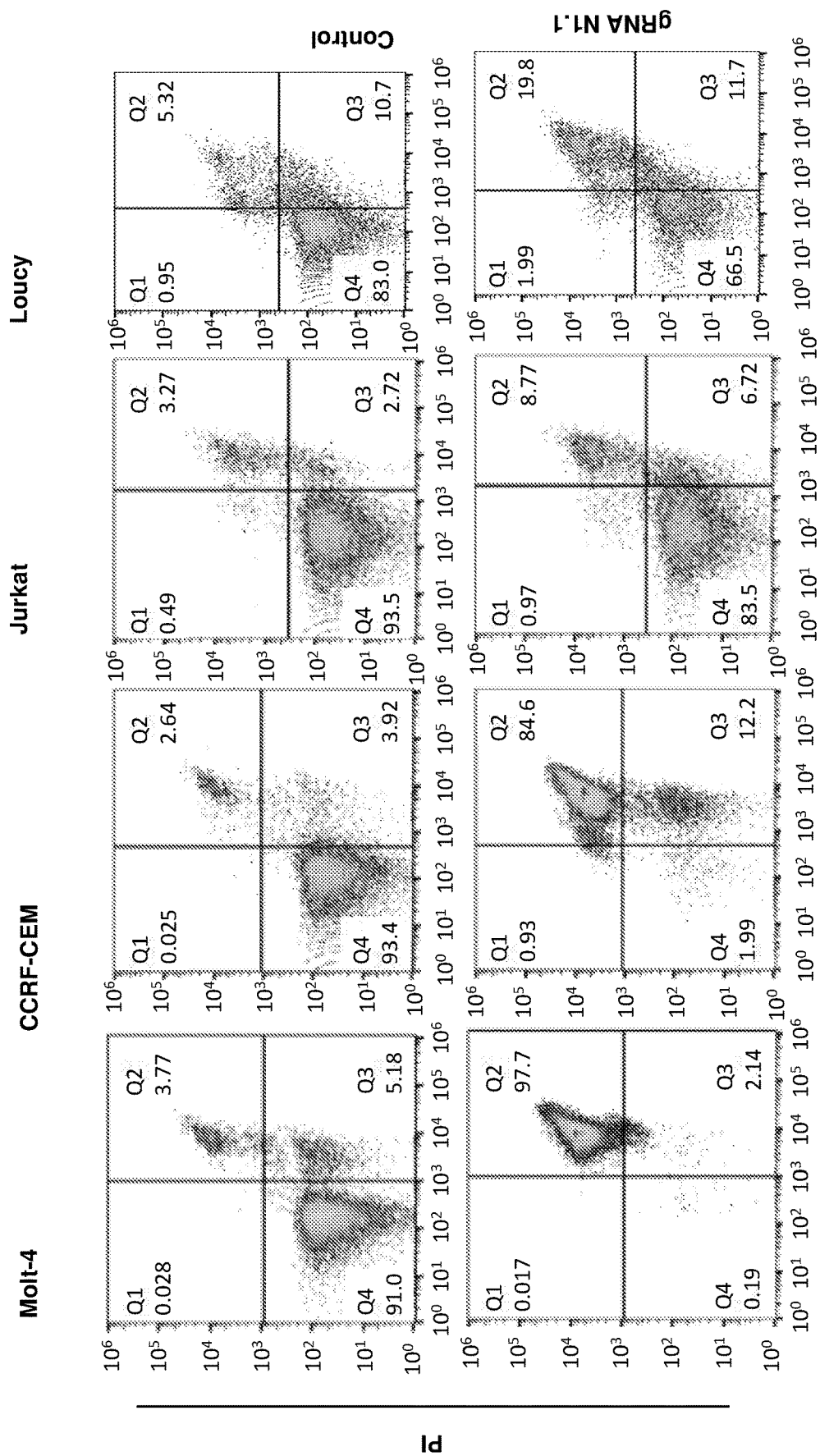

CCRF-CEM and Molt-4 to which *Cannabis* Extract 12 showed significantly greater cytotoxicity than Loucy or Jurkat cell lines, have previously been reported as harboring Notch1 mutations. Hypothesizing that the anti-tumor effect of Extract 12 depends on Notch1 signaling, the inventors first measured the mRNA expression of Notch1 in each cell line and revealed that Notch1 expression was significantly higher in CCRF-CEM and Molt-4 (FIG. 6A). Then, the inventors verified that Notch1 is crucial for survival of CCRF-CEM and Molt-4 cells, but not Loucy or Jurkat cells, by knocking out the Notch1 gene in all of these cell lines (FIGS. 6B-6C). The inventors used CRISPR technology to knockout (KO) Notch1 and found that KO Notch1 resulted in cell death in CCRF-CEM and Molt-4 cells, but not in Loucy or Jurkat cells (FIG. 6C), thus demonstrating the dependency of CCRF-CEM and Molt-4 cells on the Notch1 pathway.

Figure 7A:
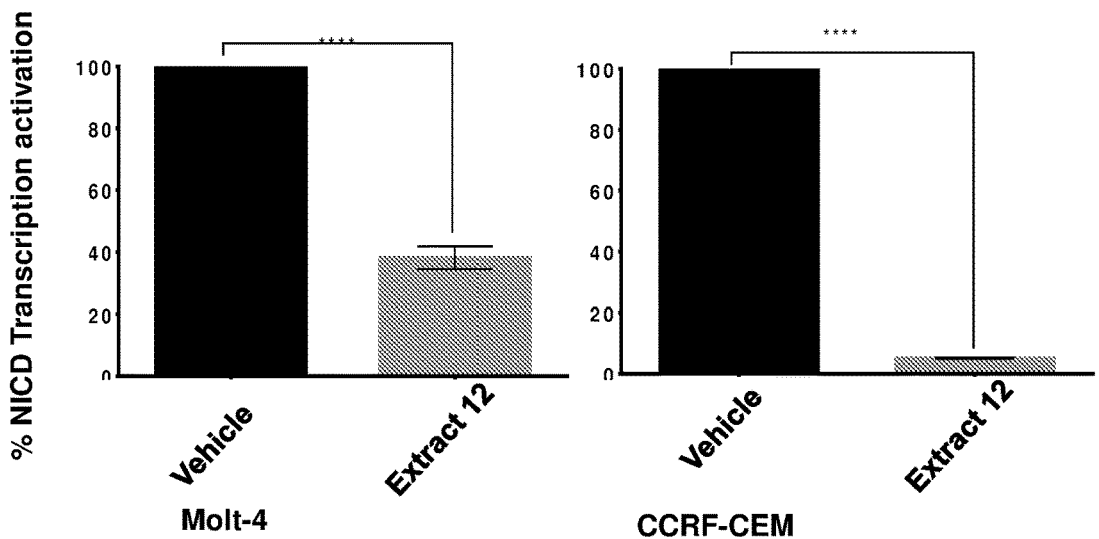
FIGS. 7A-7F are graphs and micrographs of western blot analyses showing that *Cannabis* Extract 12 influences mutant Notch1 signaling. (7A) NICD transcription activation after treatment of vehicle or Extract 12 at concentration of 5 µg/mL for 3 h in Molt-4 or CCRF-CEM, data are presented as mean±S.D. (n=3) and statistically analyzed by two-way ANOVA. (7B) Representative blot of key proteins in Notch1 signaling after treatment with vehicle or Extract 12 at a concentration of 5 µg/mL for 3 h. (7C) Protein expression analysis after treatment with vehicle or Extract 12 at a concentration of 3 µg/mL for 3 h (n=3, unpaired t-test, *p<0.05, p<0.005, *p<0.0005). (7D) Representative blot of NICD endogenic and over expression, GAPDH as a loading control. (7E) Molt-4 NICD transcription activation after NICD overexpression (n=3) relative to endogenic NICD transcription activation (unpaired t-test, *p<0.05). (7F) AlamarBlue® assay shows viability percentage after treatment with vehicle or Extract 12 (5 µg/mL) in Molt-4 cells or NICD overexpression Molt-4 for 24 h (n=4, one-way ANOVA, **** p<0.001).

The inventors next verified whether Extract 12 affected Notch1 activity directly. First, the inventors examined NICD changes and the activity of Notch1 signal transduction after applying Extract 12 on the MOLT-4 and CCRF-CEM cell lines. A reporter assay showed that Extract 12 results in a 62% reduction in NICD target gene activation in the nucleus in Molt-4 and a 95% reduction in CCRF-CEM cell lines (FIG. 7A).

Figure 7B:
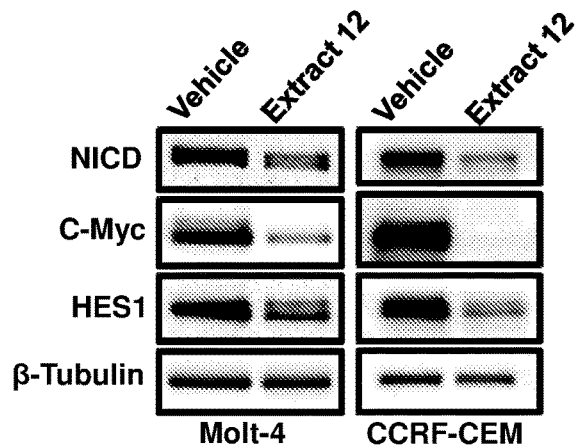
Figure 7C:
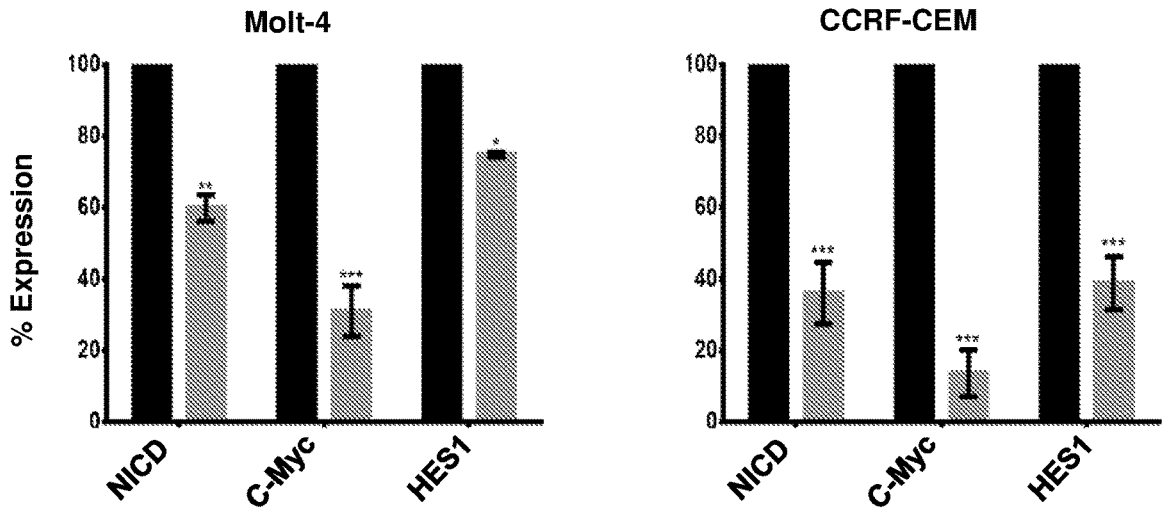

Additionally, the inventors verified that the levels of NICD protein, and its downstream targets c-MYC and HES1, were significantly reduced after 3 hours of treatment with Extract 12, (by 46%, 70% and 28% respectively, FIGS. 7B-7C), using immunoblotting.

Figure 7D:
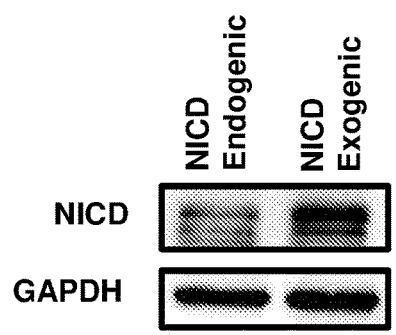
Figure 7E:
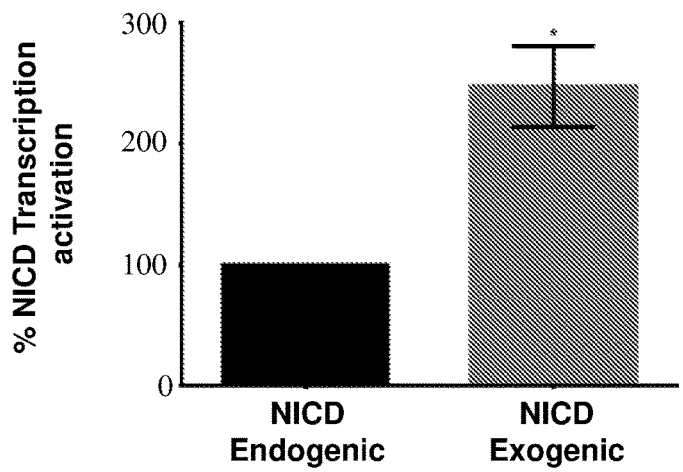
Figure 7F:
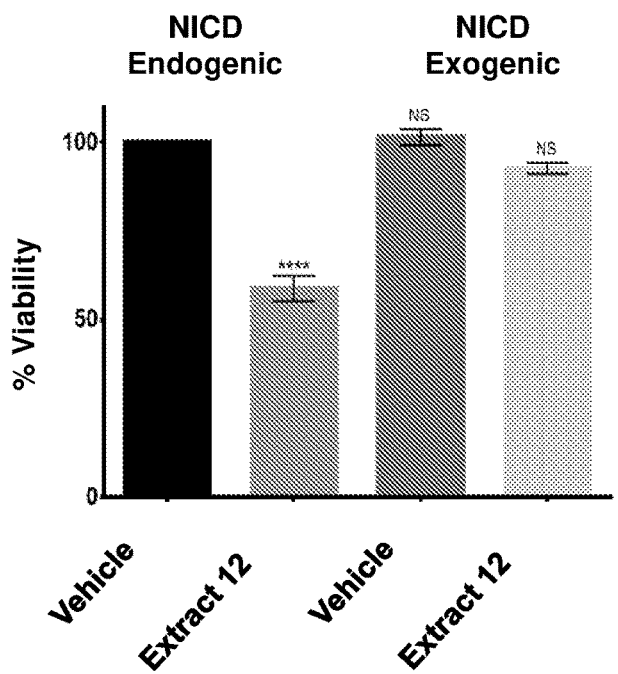

In order to further clarify the importance of Notch1 for Molt-4 survival, NICD was overexpressed by transducing cells with 3X-Flag-mNICD (NICD-Exogenic; FIG. 7D). In Molt-4 cells, NICD overexpression elevated significantly NICD transcription activity (FIG. 7E) and a cell viability assay demonstrated that Molt-4 cells are protected from Extract 12 induced cell death when a non-inhibitable NICD was overexpressed (FIG. 7F). This 'rescue' result clearly shows that *Cannabis* Extract 12 specifically acts by affecting Notch1 signaling.

Example 6

The Mechanism by which *Cannabis* Extract 12 Downregulates Mutant Notch1

Figure 8A:
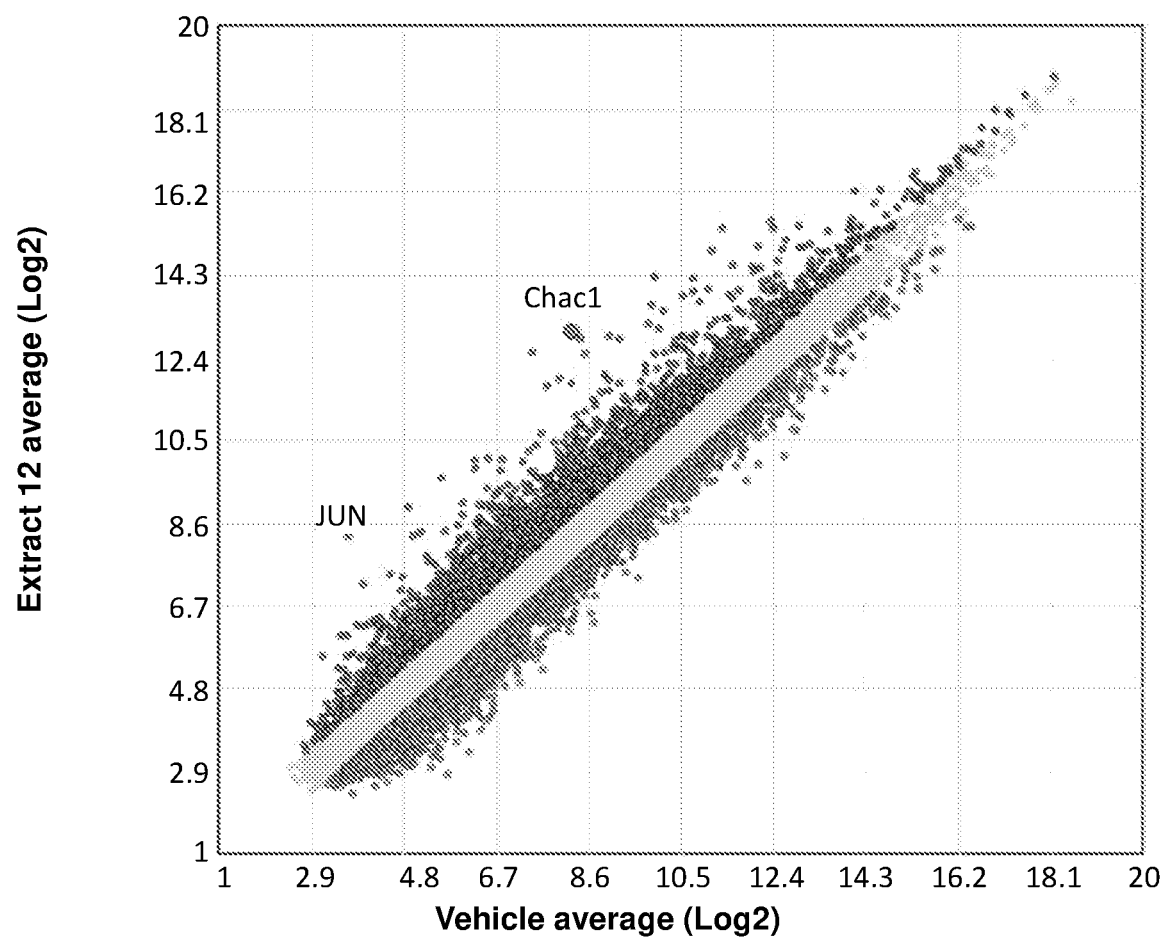
FIGS. 8A-8F are graphs and micrographs of western blot analyses showing the mechanism through which mutant Notch1 is downregulated by *Cannabis* Extract 12. (8A) RNA Seq (affimetrix) Scatter plot. (8B) Real-time PCR of Chac1 gene. (8C) Analysis of Chac1 expression at different time points (n=3, unpaired t-test, *p<0.05, **p<0.005) with representative blot of Chac1 and β-Tubulin. (8D) Representative blot of Full Notch1, NICD and β-Tubulin after treatment of Extract 12 for 3 h. (8E) Analysis of Full Notch1 expression after treatment of Extract 12 for 3 h (n=3, unpaired t-test, *p<0.05, **p<0.005). (8F) Analysis of phospho C-Jun expression at different time points (n=3, unpaired t-test, *p<0.05, **p<0.005) with representative blot of phospho C-Jun and C-Jun.
Figure 8B:
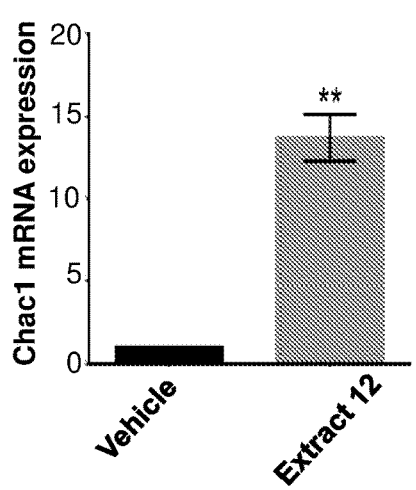
Figure 8C:
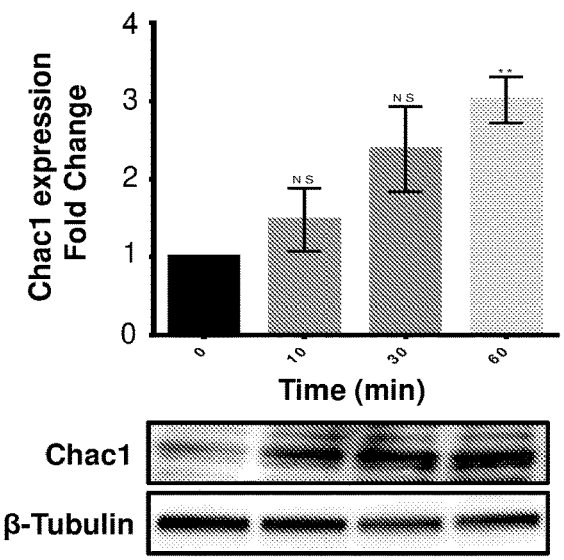
Figure 8D:
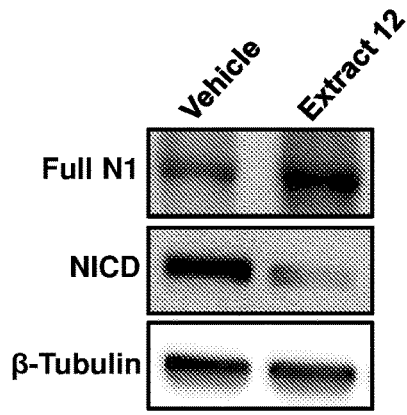
Figure 8E:
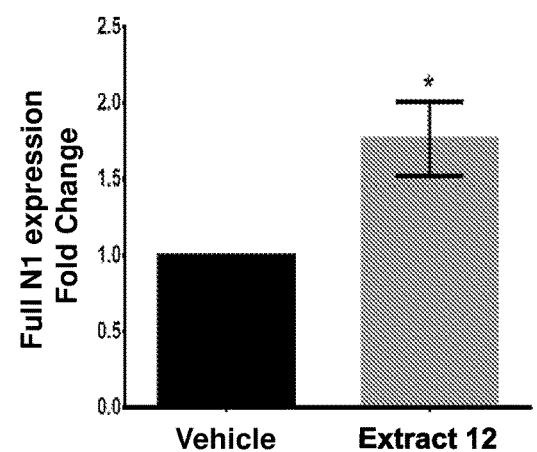
Figure 8F:
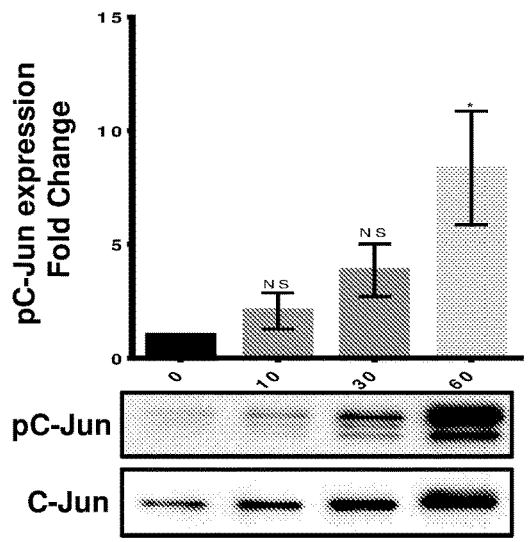

As a first step towards uncovering the mechanism through which Notch1 is down-regulated by Extract 12, the inventors used RNA-sequencing (RNA-Seq) analysis to measure and compare the gene expression profile of Molt-4 cells after treatment with vehicle or *Cannabis* Extract 12 (FIG. 8A). CHAC1, a negative regulator of the NOTCH signaling pathway, was identified as the second most up regulated gene. The inventors confirmed the RNA-seq results by quantitative reverse transcription PCR (qRT-PCR) showing that CHAC1 mRNA is up-regulated 14 folds after treatment with Extract 12 (FIG. 8B). Protein levels of CHAC1 were also significantly up-regulated in a time dependent manner (FIG. 8C). CHAC1 acts by inhibiting Furin Notch1 cleavage, preventing formation of the mature form of Notch1. In order to confirm that Extract 12 acts by preventing Notch1 maturation, the inventors showed that treatment with Extract 12, leads to increased amounts of full length Notch1 suggesting that the full-length immature form, accumulates after treatment with Extract 12 (FIGS. 8D-8E). Since previous studies suggested that the c-Jun pathway enhances expression levels of the CHAC1, the inventors examined phosphorylation of c-Jun after treatment with Extract 12 and observed significant time dependent up-regulation of phospho c-Jun (FIG. 8F). Overall, the results suggest that Extract 12 reduces NICD levels by preventing Notch1 maturation through elevation of c-Jun and CHAC1.

Figure 14:
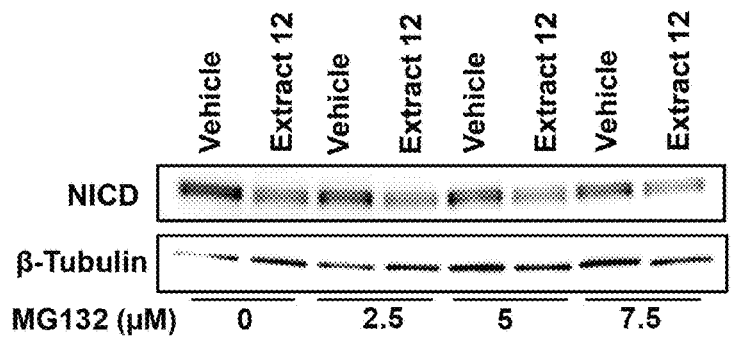
FIG. 14 is a micrograph of a western blot analysis of NICD in Molt-4 cells pretreated with MG132 (proteasome inhibitor; 0, 2.5 µM, 5 µM, 7.5 µM) for 1 h and then treated with vehicle or Extract 12 (5 µg/mL) for 3 h. β-tubulin served as a loading control.
Figure 15:
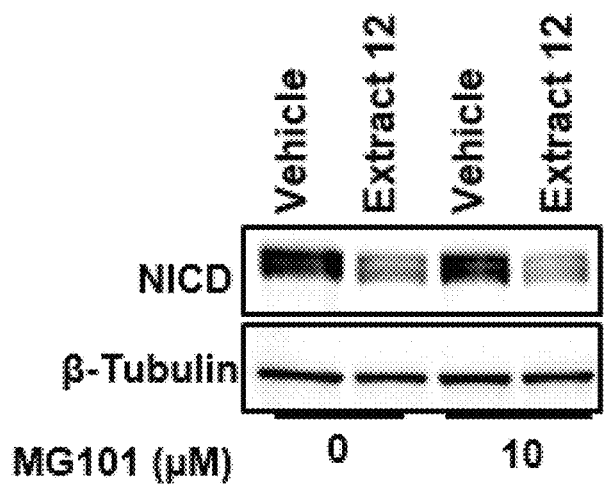
FIG. 15 is a micrograph of western blot analysis of NICD in Molt-4 cells pretreated with MG101 (proteasome inhibitor; 0, 10 µM) for 1 h and then treated with vehicle or Extract 12 (5 µg/mL) for 3 h. β-tubulin served as a loading control.

The inventors further examined whether NICD level is reduced by degradation, using proteasome inhibitors (MG132 and MG101). Proteasome inhibition did not restore the protein level of NICD in MOLT-4 cells (FIGS. 14 and 15).

Example 7

*Cannabis* Extract 12 Inhibits Tumor Growth in-vivo

Figure 9A:
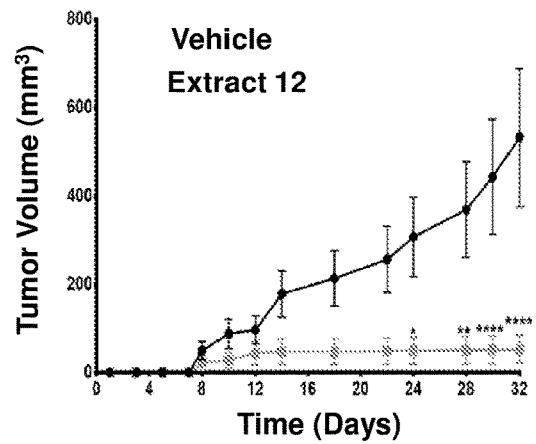
FIGS. 9A-9H are graphs and micrographs showing that *Cannabis* Extract 12 inhibits tumor growth in-vivo. (9A) Growth curve of tumor volume following *Cannabis* treatment (treatment started after 2 days from cells injection). (9B) Tumor weight analysis of fifteen xenografts for each treatment (vehicle or Extract 12). Data are presented as mean±S.D. (n=30) and statistically analyzed by student t-test. (9C) Representative pictures of tumors (treatment started after 2 days from cells injection). (9D) Representative fluorescent micrographs showing NICD staining. (9E) Representative pictures of tumors (treatment started after 14 days from cells injection). (9F) Growth curve of tumor volume following *Cannabis* treatment. (9G) Tumor weight analysis of nine xenografts for each treatment (vehicle or Extract 12), data are presented as mean±S.D (n=9) and statistically analyzed by student t-test. (9H) Human CCRF-CEM (hCD45) percentage in the bone marrow (data are presented as mean±S.D; (n=19) and statistically analyzed by student t-test).
Figure 9B:
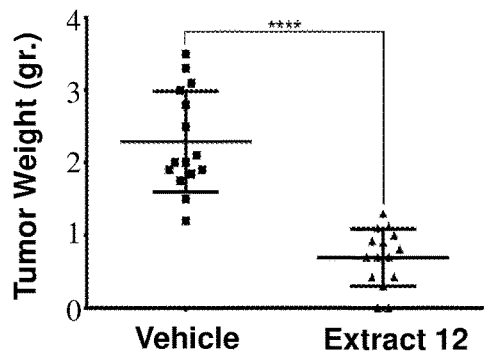
Figure 9C:
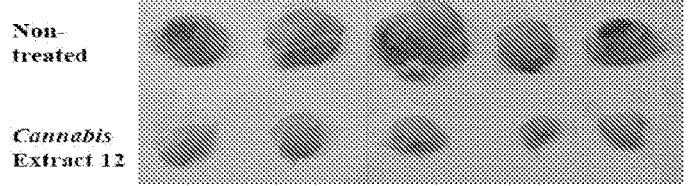
Figure 9D:
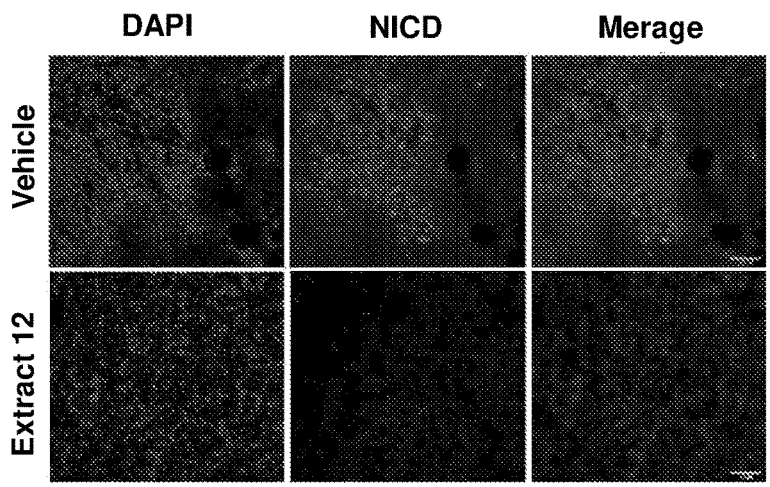
Figure 9E:
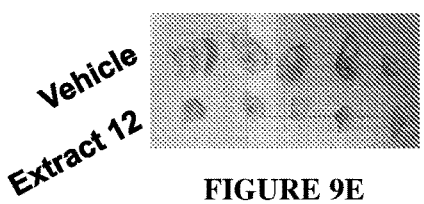
Figure 9F:
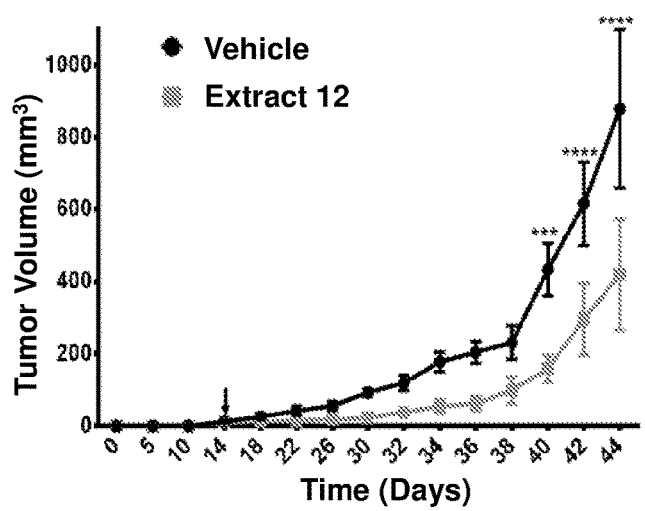
Figure 16:
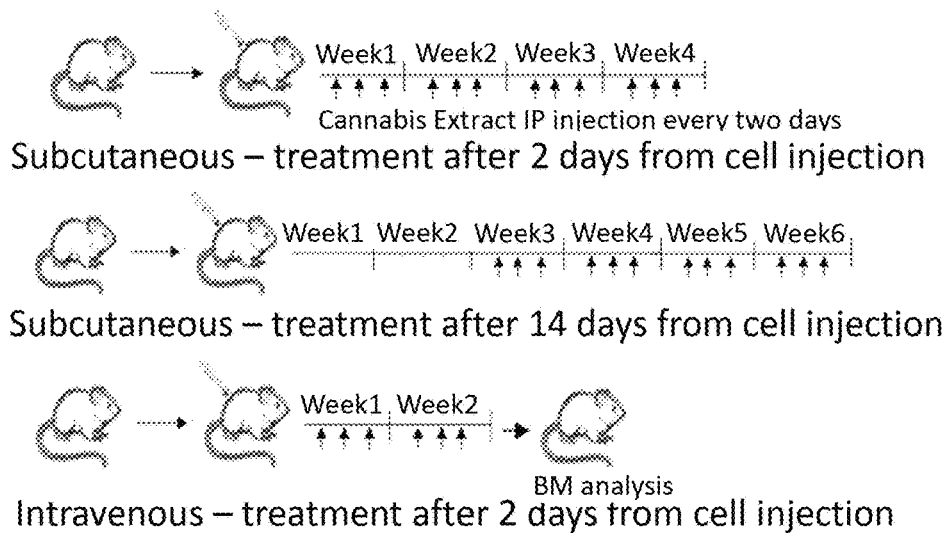
FIG. 16 is an illustration of a non-limiting timeline of an in-vivo study.

The inventors further evaluated the anti-tumor properties of Extract 12 in an in-vivo model. In order to do so, the inventors used several mice models. First, the inventors allografted immunodeficient NOD-SCID mice with Notch1 mutated T-ALL cells (Molt-4) and treated them with vehicle only or Extract 12, two days after injection (FIG. 16). The results show clearly that treatment with Extract 12 significantly inhibited the tumor growth (P<0.0001, compared to the control group (FIGS. 9A-9C). Immunofluorescent staining showed that the expression levels of NICD were much lower in tumors from the treated group compared to the control group (FIG. 9D). Next, the inventors treated the immunodeficient NOD-SCID mice with Extract 12, fourteen days after injection with Notch1 mutated T-ALL cells (Molt-4) (FIG. 16). Mice in both the treatment and control groups developed subcutaneous tumors but tumor growth as measured by tumor volume increase over time, was significantly reduced in the Extract 12 treated group (P<0.0001) compared to the control group (FIGS. 9E-9F). Furthermore, after forty-four days tumors weight were significantly lower in the treated group compared to the control group (P<0.001, FIG. 9G).

Figures 9G, 9H:
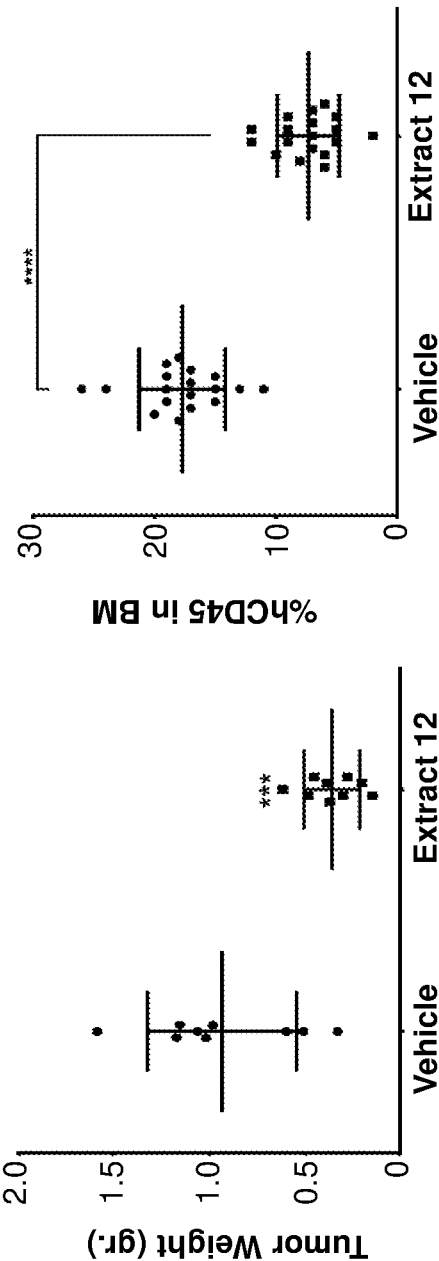

In addition, the inventors engrafted NOD-SCID gamma (NSG) mice with Notch1 mutated T-ALL cells (CCRF-CEM) and then treated them with Extract 12 every two days for four weeks, starting at 2 days after injection (FIG. 16). Counting positive human CD45 cells from the bone marrow showed a significant (P<0.0001) decrease in human CD45 percentage in the bone marrow after treatment with Extract 12 (FIG. 9H). The results clearly show that Extract 12 has anti-tumor properties both in-vivo and in-vitro.

Example 8

Identifying the Specific Antitumor Phytocannabinoids in *Cannabis* Extract 12

Figure 10A:
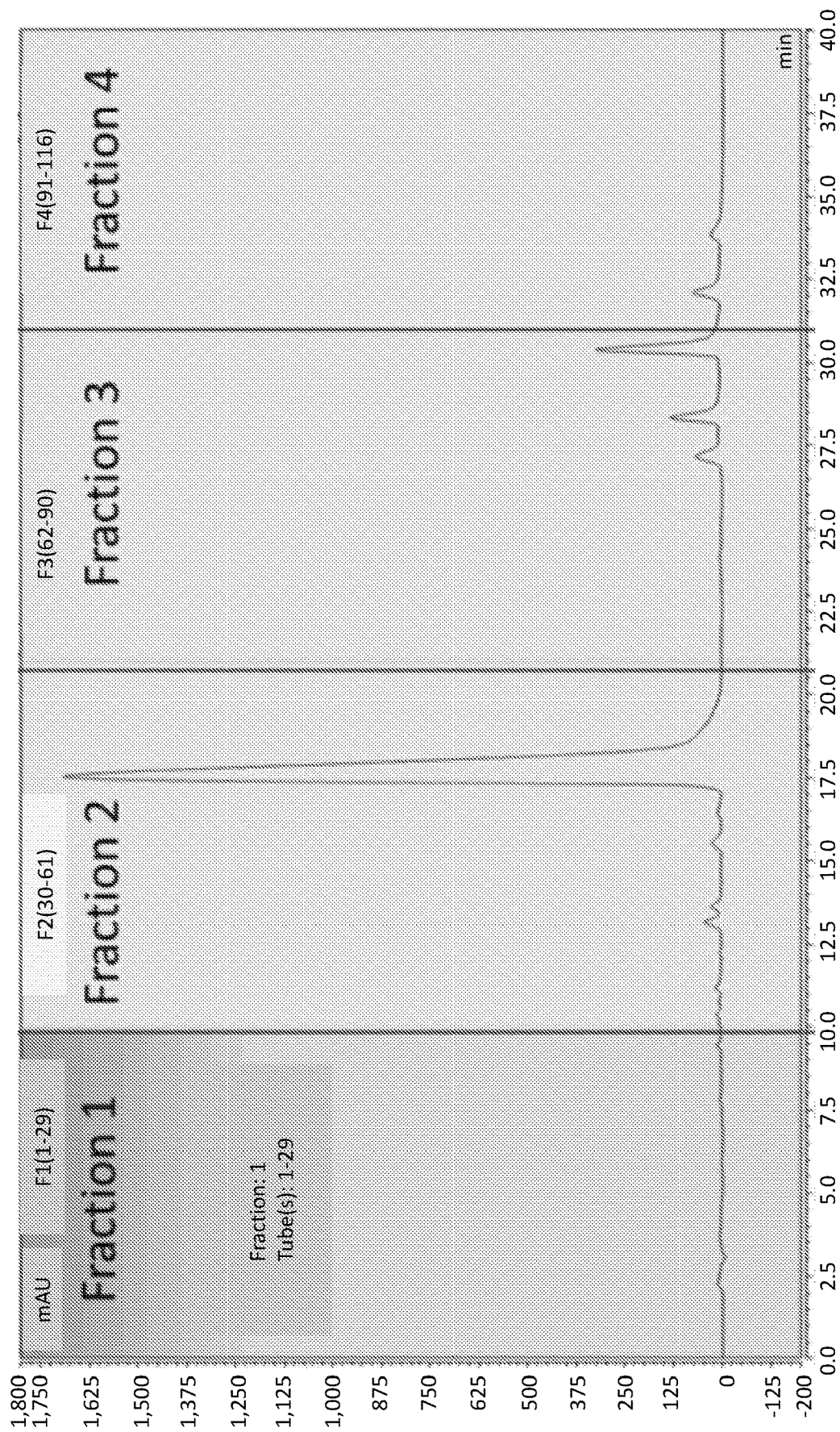
FIGS. 10A-10K are graphs and a micrograph elucidating the compounds which induce cell apoptosis on MOLT-4 cells. (10A) Extract 12 fractionation via semi-preparative high-performance liquid chromatography (semi-prep HPLC) into four fractions of 10-minute retention-time intervals. (10B) is a vertical bar graph presenting the results of a viability assay of Molt-4 cells 24 h after treatment with whole Extract 12 and four fractions. (10Ci) An Annexin-V assay showing that apoptosis induction of 3 µg/mL of fraction 2 is similar to the whole extract after 24 h of application. (10Cii) A vertical bar graph showing that the % apoptotic cells in the presence of fraction 2 is similar to that of the whole extract. (10D) Representative blot of NICD, Cleaved Caspase-3 and β-Tubulin. (10E) Fraction 2 is fractionated into specific peaks (C1, C2, C5). (10F) A viability assay showing that three cannabinoids are as effective as the whole extract in producing MOLT-4 cell death. (10G) A viability assay of Molt-4 cells 24 h after treatment with varying concentrations of CBD, CBDV, CF1, and combinations thereof. (10H) A viability assay of CCRF-CEM cells 24 h after treatment with varying concentrations of CBD, CBDV, CF1, and combinations thereof. (10I) Analysis of apoptosis (based on an Annexin V assay) shows that three cannabinoids are as effective as the whole extract in producing MOLT-4 cell death (n=3, unpaired t-test). (10J) Western blot analysis of protein expression shows that some phytocannabinoids (3 µg/mL) are responsible for downregulation of Notch lICD and upregulation of cleaved caspase-3 after 24 h of application. (10K) Analysis of NICD expression of different cannabinoid combinations (n=3, unpaired t-test).
Figure 10B:
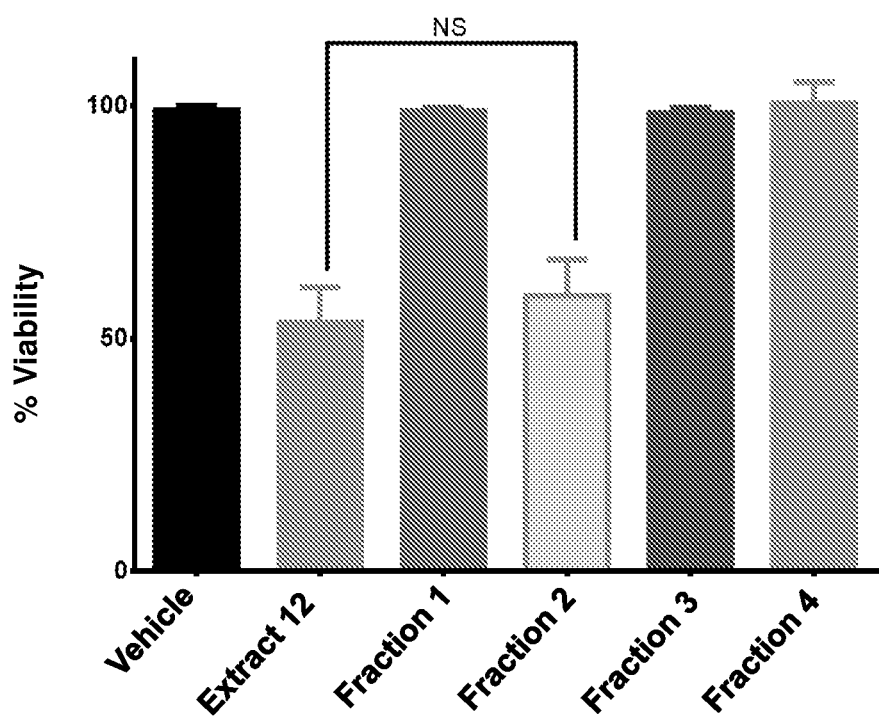
Figure 10C:
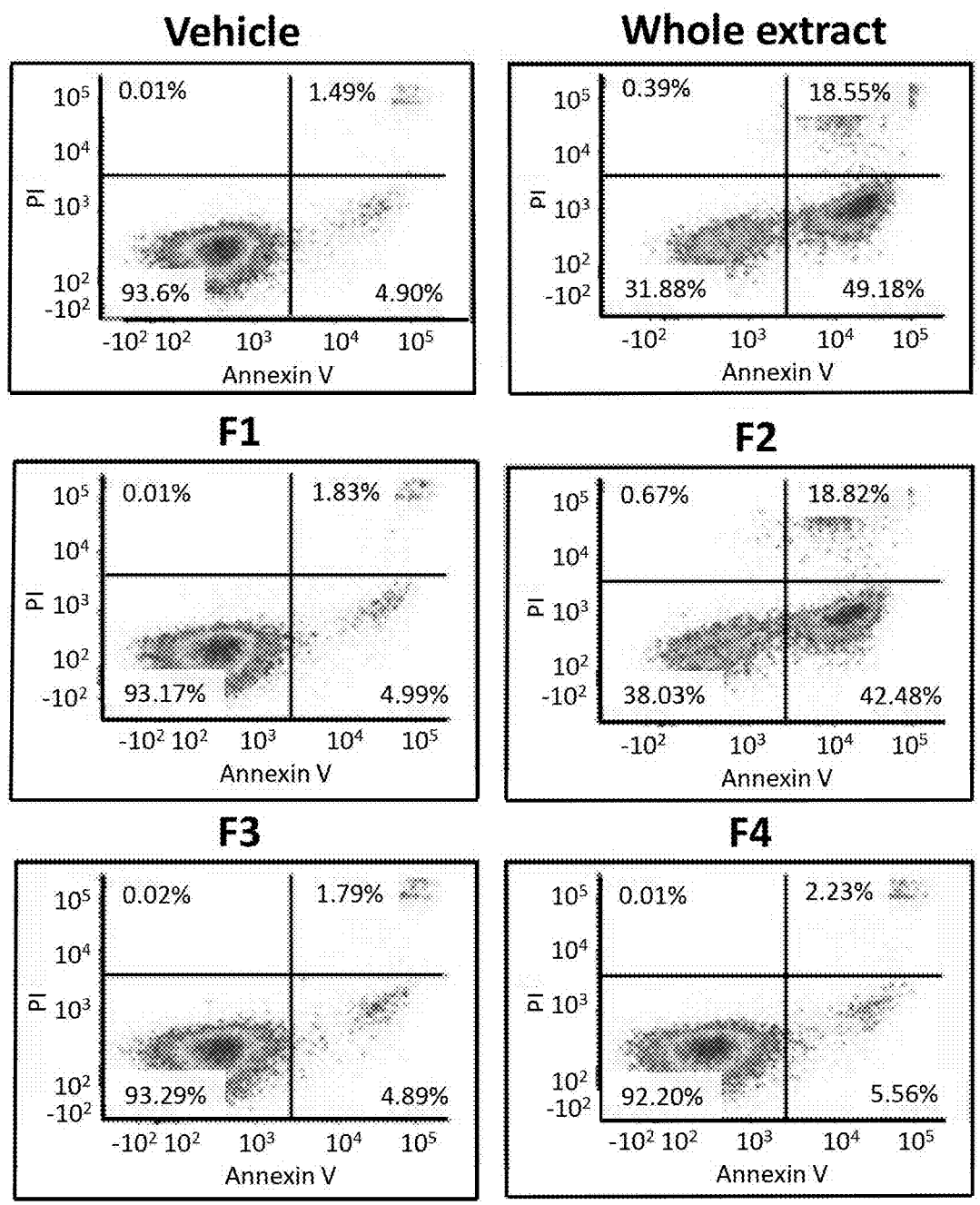
Figure 10D:
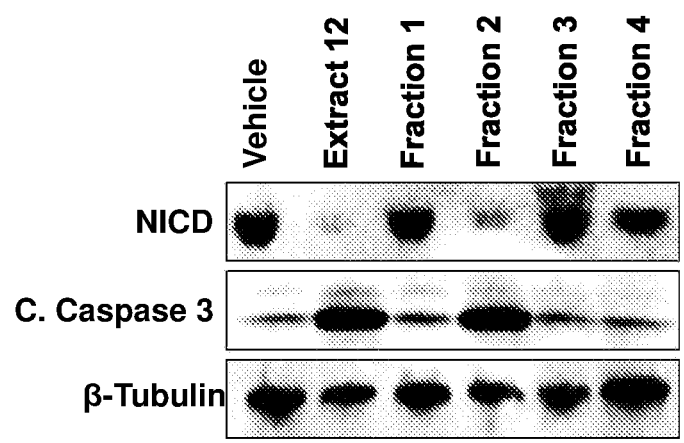
Figure 10E:
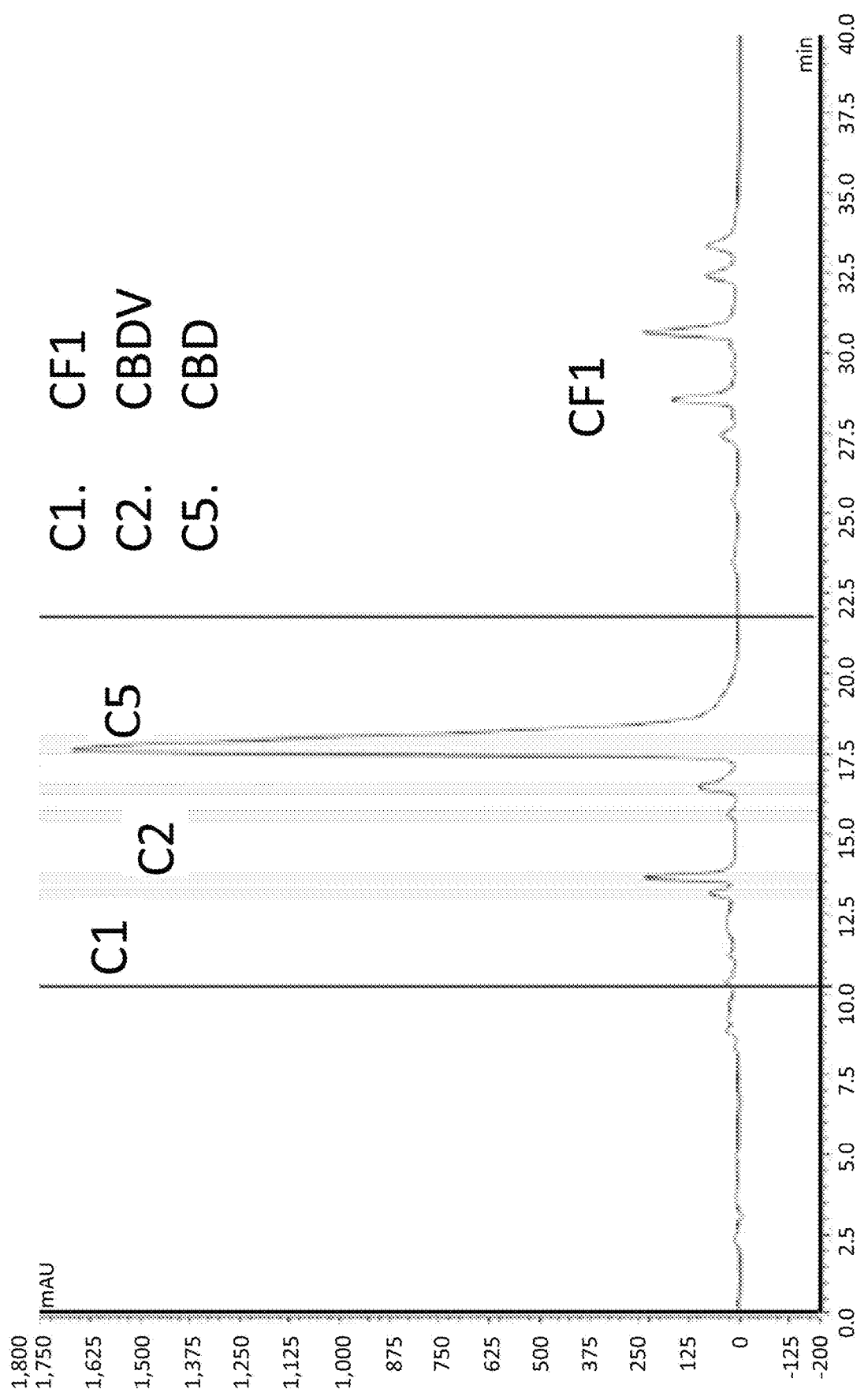
Figure 10F:
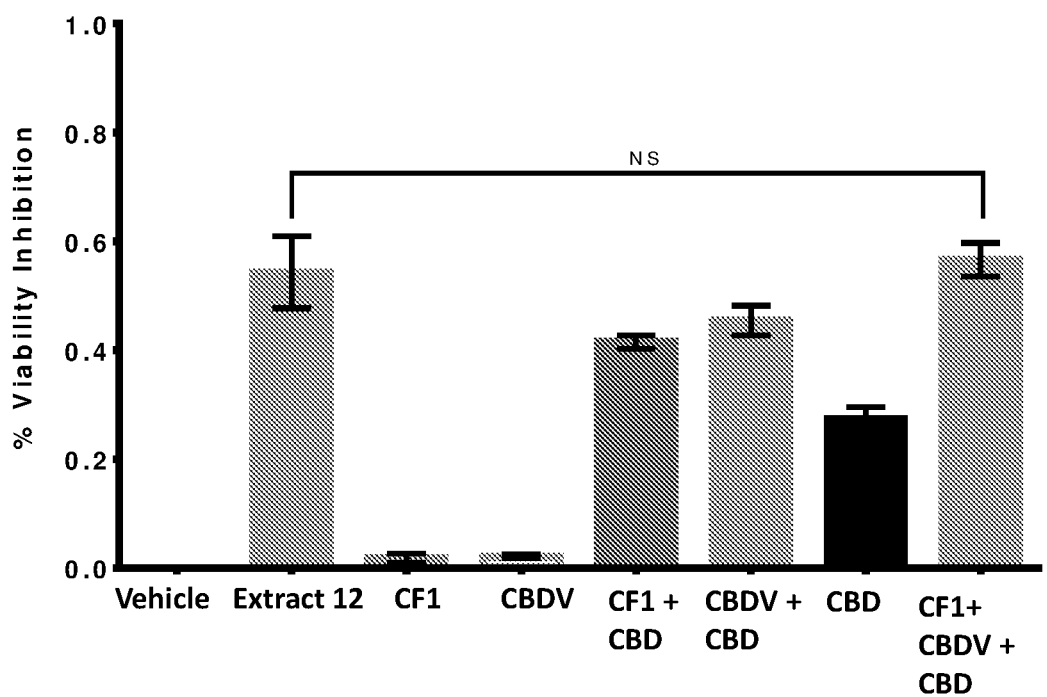
Figure 10G:
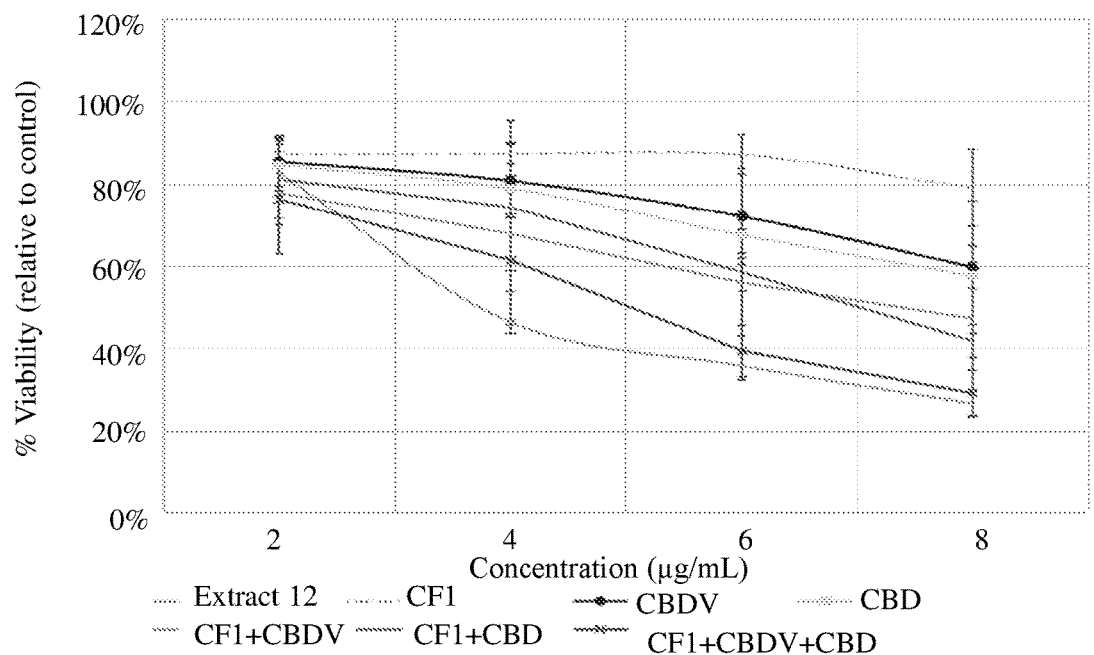
Figure 10H:
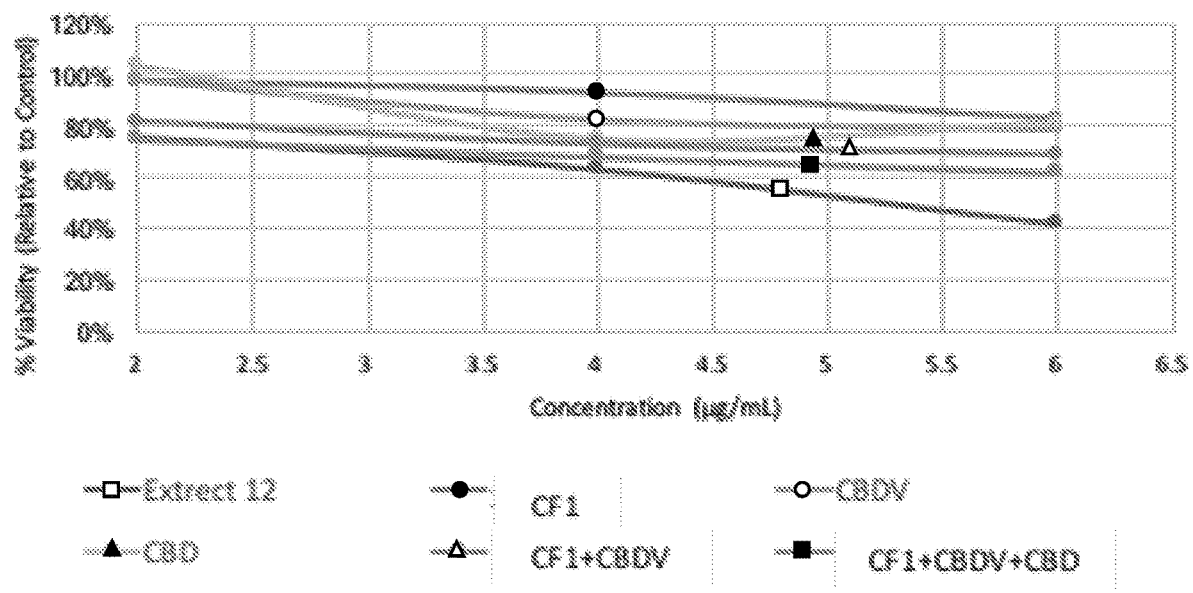
Figure 10I:
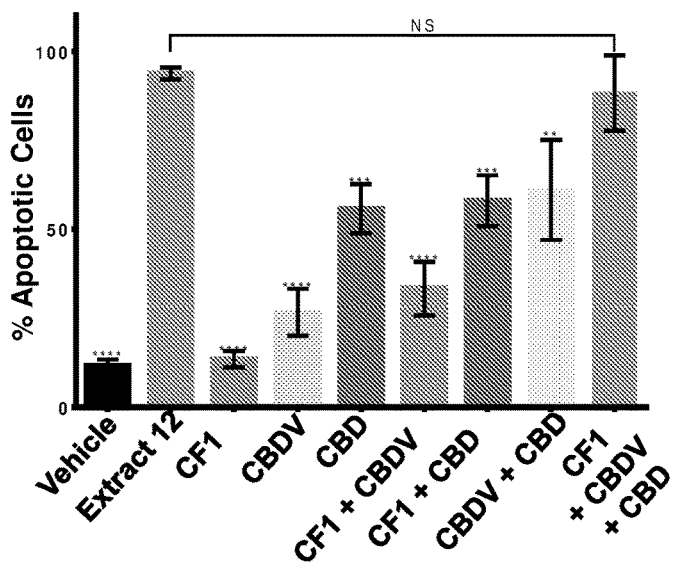

Extract 12 was fractionated into 4 fractions using a semi-prep HPLC by dividing the chromatographic runtime (40 min) into 10 min ranges (FIG. 10A). Phytocannabinoids in each fraction were analyzed by UHPLC/UV and the effects of each fraction on viability and apoptosis were examined (FIGS. 10B-10D). The experiment revealed that fraction 2 was responsible for the major viability and apoptosis effects of the NOTCH1-mutated cell lines MOLT-4 (FIGS. 10B-10D). Fraction 2 was further fractionated to specific fractions (C1-C5 in FIG. 10E) via CPC and semi-prep HPLC and analyzed via LC/MS/MS. Three of the isolated compounds were found to be critical to the antitumor effect of Extract 12 and to the effect of Notch1 signaling (C1, C2, and C5). These were identified as CBD, CBDV, and a compound referred to herein as CF1 which was found to be critical to complement the antitumor effect of fraction 2 (FIGS. 10F-10K).

Figure 10J:
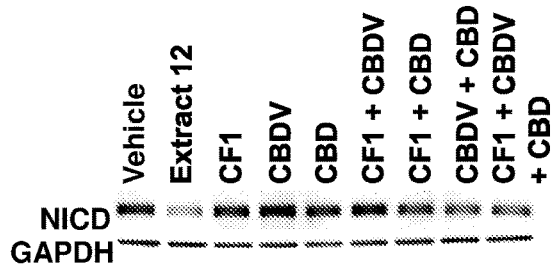
Figure 10K:
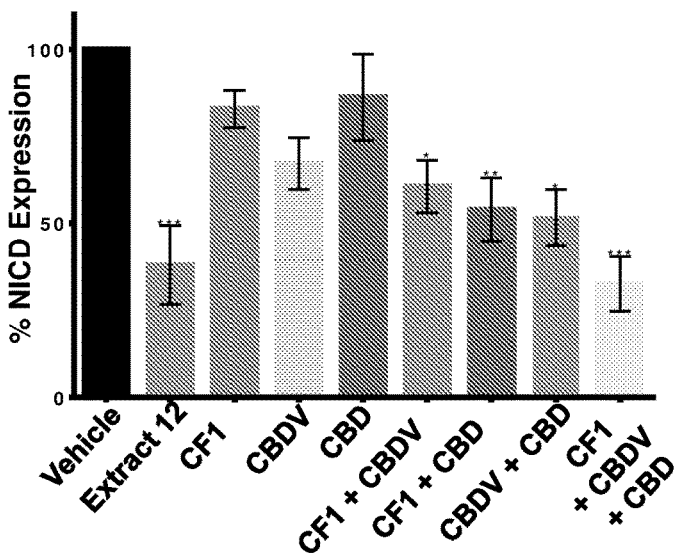

A viability assay was performed in MOLT-4 and CCRF-CEM cells comprising CBD, CBDV and CF1, separately and in different combinations. All three cannabinoids and combinations thereof produced cell apoptosis (FIGS. 10F-10I) and decreasing NICD levels (FIGS. 10J-10K).

Figure 12:
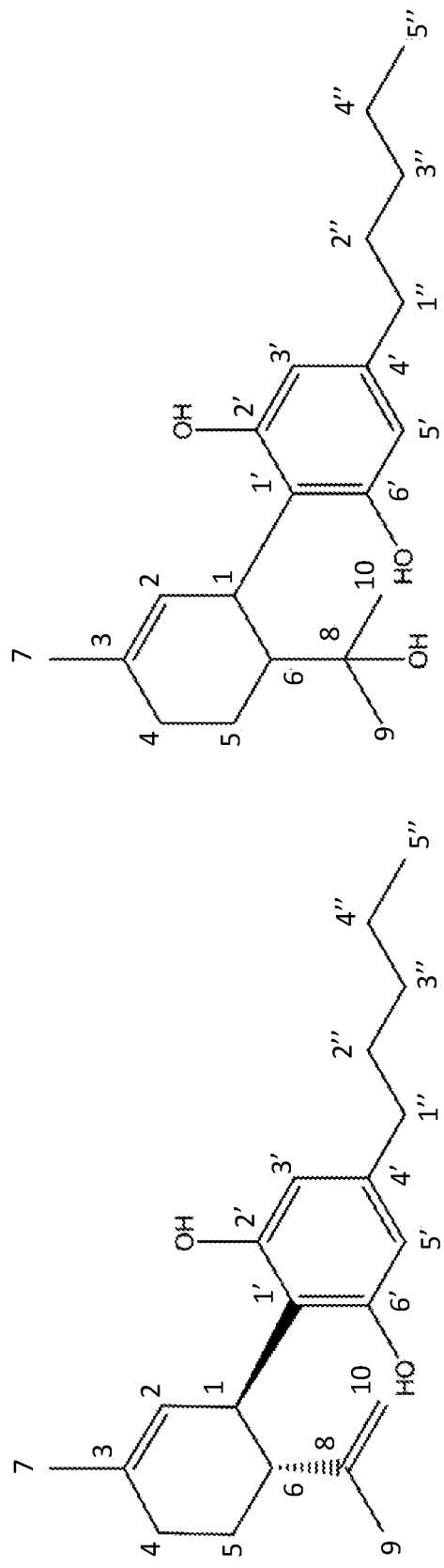
FIG. 12 is the chemical structure of CBD (left) and CF1 (right).

The inventors have previously identified CF1 in decarboxylated "high-CBD" *Cannabis* strains (Berman et al., 2018). It was identified as a phytocannabinoid compound having a structure of Formula 1 and/or having a deprotonated accurate mass of 331.2279 Da, a retention time (RT) of 7.14 min and a MS/MS spectrum (FIG. 11), which exhibits deprotonated fragments typically presented for other identified phytocannabinoids including, 313.2173, 245.1547 and 179.1067 Da. The structure of CF1 was further elucidated via $^1$H and $^{13}$C NMR. CBD as a reference and the isolated CF1 were dissolved in $CDCl_3$ and analyzed at 5° C. with TMS as the internal reference. Chemical shifts of the peaks are provided in Table 1 hereinbelow. The structure and peak assignments of the CBD and CF1 according to the NMR analysis appear in FIG. 12.

TABLE 1

$^1$H and $^{13}$C NMR data of CBD and CF1 in $CDCl_3$

| Carbon number | CBD | | CF1 | |
| --- | --- | --- | --- | --- |
| | $\delta_H$ [ppm] | $\delta_C$ [ppm] | $\delta_H$ [ppm] | $\delta_C$ [ppm] |
| 1 | 3.85 | 37.08 | 3.83 | 32.63 |
| 2 | 5.57 | 123.96 | 5.71 | 123.45 |
| 3 | — | 140.21 | — | 140.20 |
| 4 | 2.10, 2.23 | 30.31 | 2.06, 2.13 | 27.08 |
| 5 | 1.77, 1.82 | 28.28 | 1.73, 1.97 | 22.66 |
| 6 | 2.39 | 46.10 | 1.90 | 48.24 |
| 7 | 1.79 | 23.75 | 1.81 | 23.82 |
| 8 | — | 149.38 | — | 75.19 |
| 9 | 1.66 | 20.44 | 1.25 | 25.97 |
| 10 | 4.55, 4.67 | 110.86 | 1.26 | 29.70 |
| 1' | — | 113.63 | — | 114.66 |
| 2' | — | 155.95 | — | 155.97 |
| 2'-OH | 6.05 | — | 6.61 | — |
| 3' | 6.29 | 109.68 | 6.26 | 109.44 |
| 4' | — | 143.02 | — | 143.52 |
| 5' | 6.16 | 107.88 | 6.33 | 109.44 |
| 6-OH | 4.77 | — | 7.64 | — |
| 6' | — | 153.78 | — | 154.23 |
| 1" | 2.43 | 35.44 | 2.45 | 35.49 |
| 2" | 1.55 | 30.69 | 1.57 | 30.74 |
| 3" | 1.27 | 31.46 | 1.29 | 31.52 |
| 4" | 1.30 | 22.55 | 1.31 | 22.56 |
| 5" | 0.87 | 14.09 | 0.88 | 14.08 |

The NMR data of CBD was in close agreement with the literature (Marchetti et al., 2019). The spectra of CBD and CF1 were very similar with the exception of the disappearance of the external double bond ($C_8$-$C_{10}$) and appearance of a tertiary alcohol instead. CF1 has two chiral centers and therefore may be one or more (in case of a racemate) of four stereoisomers: 1R,6S, 1S,6R, 1S,6S or 1R,6R (according to FIG. 12).

Among the tested extracts, Extract 12 had the most significant concentrations of all three identified phytocannabinoids (FIG. 1). Extract 12 phytocannabinoid concentrations appear in FIG. 17.

Example 9

A Combination of Three Phytocannabinoids Inhibits Tumor Growth in-vivo

In order to examine if the combination of these three specific cannabinoids can inhibit tumor growth in-vivo the inventors injected immunodeficient NOD-SCID mice subcutaneously with Notch1 mutated T-ALL cells (Molt-4) and treated them with vehicle only or the combination of the three purified and identified cannabinoids, starting two days after injection (FIG. 18). Similar to the whole Extract 12, treatment with the combined three specific cannabinoids, significantly reduced tumor size (FIG. 13A, P<0.0001) and tumor weight (FIGS. 13B and 13C, P<0.0025) compared to the control vehicle. The inventors quantified the phytocannabinoids in the tumors that were treated with the three isolated phytocannabinoids composition. FIG. 13D shows that all the three phytocannabinoids entered the tumor at the same ratio they were injected. Moreover, when examining NICD expression in the tumors, there was a significant decrease in NICD expression in the tumors treated with the phytocannabinoids composition (FIGS. 13E-13F).

Example 10

Identifying the Activated Cannabinoid Receptors

To reveal which receptors are involved in the phytocannabinoids' effects on the cell the endocannabinoid receptors that are expressed by MOLT-4 and CCRF cells are examined. Using a variety of commercial inhibitors for cannabinoid receptors, MOLT-4 cells are treated with the inhibitors and the activity of every purified component is analyzed by proliferation and apoptosis assays. Next, using a cannabinoid receptor cell-base assay, the activity of every purified component on a suspected receptor is directly measured. To confirm the interaction of the phytocannabinoids with the receptor in a more direct way, QCM-Z500 (KSV Instruments) is used. The interaction kinetics of the molecules in vitro are analyzed by using a quartz crystal microbalance (QCM). The QCM measurements are performed using the commercially available AT-cut polished and His-tag purified receptors.

Example 11

The Anti-Tumor Activity of Cannabinoids on Primary Human T-ALL Cells

Peripheral blood samples from 80 T-ALL patients (bearing/not bearing NOTCH1-associated mutations) are analyzed using single cells genomics for NOTCH1-related mutations. For each blood sample the following genes are sequenced: NOTCH1, TACE, ADAM10, FBXW7, RBPJ, Presenilin-1, Nicastrin, APH-1, PEN-2, MAML1 and Furin (Borggrefe & Oswald, 2009). The toxicity of the selected phytocannabinoids from the experiments done on cell lines and in vivo, are assessed on human primary T-ALL cells. Peripheral blood T cells from healthy donors are isolated, treated with different doses of the phytocannabinoids and tested for viability post treatment. Sub-toxic doses of the three purified phytocannabinoids are defined. The above sub-toxic doses are used for testing the effect of the three phytocannabinoids on primary T-ALL cells isolated from patient blood samples. Assuming not all patients have NOTCH1-related mutations, this data is combined with the genomic analysis done for NOTCH1-mutations in these patients to test the correlation between NOTCH1-mutations and potential death (Helsinki #0309-17-RMB).

The primary T-ALL samples are also metabolomically analyzed by LC/MS/MS as previously described and mRNA is extracted in order to detect the expression of the endocannabinoid receptors in these mutated cells. In addition, primary T-ALL cells containing NOTCH1 mutations are injected SC into NSG mice and the capacity of the cells to establish leukemia in vivo following phytocannabinoid treatment is analyzed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A pharmaceutical composition comprising as an active ingredient a compound referred to as CF1 having the following chemical structure:

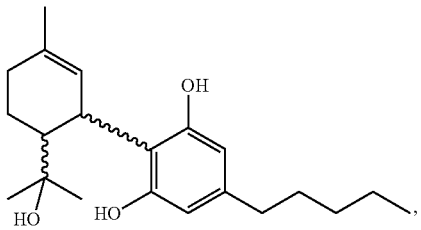

and a pharmaceutically acceptable carrier, wherein at least 5% of the cannabinoid content of the composition is CF1.

2. The pharmaceutical composition of claim 1, wherein 100% of the cannabinoid content of the composition is CF1.

3. The pharmaceutical composition of claim 1 further comprising at least one additional cannabinoid selected from the group consisting of cannabidiol (CBD) and cannabidivarin (CBDV).

4. The pharmaceutical of claim 3 comprising CF1, CBD, and CBDV, wherein:
  i. the weight per weight (w/w) ratio of CF1 to CBD ranges from 1:1 to 1:1,000;
  ii. the w/w ratio of CF1 to CBDV ranges from 1:1 to 1:1,000; and
  iii. the w/w ratio of CBDV to CBD ranges from 1:1 to 1:1,000.

5. The pharmaceutical composition of claim 4, further comprising at least one additional cannabinoid selected from the group consisting of CBGA, CBG, CBG-C4, CBGV, CBGM, SesquiCBG, THC, 48-THC, THCV, CBDA, CBDA-C4, CBD-C4, CBDVA, CBDO, CBDM, CBCA, CBC, CBC-C4, CBCVA, CBCV, CBCO, CBN, CBNV, OH-CBN, CBEA, CBE, CBEV, CBND, CBNDA, CBL, CBT-1, CBTV-1, CBT-3, and CBT-2.

6. The pharmaceutical composition of claim 5, wherein the w/w ratio of CF1, CBD, and CBDV combined to said at least one additional cannabinoid ranges from 10:1 to 100:1.

7. The pharmaceutical composition of claim 4, further comprising at least one additional cannabinoid selected from the group consisting of THC, CBDA, and CBG.

8. The pharmaceutical composition of claim 7, wherein the w/w ratio of CF1, CBD, and CBDV combined to said at least one additional cannabinoid ranges from 10:1 to 100:1.

9. The pharmaceutical composition of claim 4, wherein CF1, CBD, and CBDV combined comprise at least 50% by weight of the cannabinoids in said composition.

10. The pharmaceutical composition of claim 4, wherein one or more of the cannabinoids is present as a highly purified extract of Cannabis.

11. The pharmaceutical composition of claim 4, wherein one or more of the cannabinoids is a synthetically produced cannabinoid.

12. A method for treating a subject afflicted with a NOTCH1-related disease, the method comprising administering to said subject a therapeutically effective amount of a pharmaceutical composition according to claim 3.

13. The method of claim 12, wherein said pharmaceutical composition comprises CF1 and CBD.

14. The method of claim 13, wherein CF1 and CBD are present in said pharmaceutical composition in a weight per weight (w/w) ratio ranging from 1:1 to 1:1,000; or wherein CF1 and CBD are present in said pharmaceutical composition in a weight per weight (w/w) ratio ranging from 800:1 to 1:1.

15. The method of claim 12, wherein said pharmaceutical composition comprises CF1 and CBDV.

16. The method of claim 15, wherein CF1 and CBDV are present in said pharmaceutical composition in a weight per weight (w/w) ratio ranging from 1:1 to 1:1,000, or wherein CF1 and CBDV are present in said pharmaceutical composition in a weight per weight (w/w) ratio ranging from 1,000:1 to 1:1.

17. The method of claim 12, wherein said pharmaceutical composition comprises CF1, CBD, and CBDV.

18. The method of claim 17, wherein CBDV and CBD are present in said pharmaceutical composition in a weight per weight (w/w) ratio ranging from 1:1 to 1:1,000; or wherein CBDV and CBD are present in said pharmaceutical composition in a weight per weight (w/w) ratio of at least 100:1.

19. The method of claim 17, wherein CF1, CBD, and CBDV are present in said pharmaceutical composition in a weight per weight (w/w) ratio ranging from 1:1:100 to 1:50:1,000.

20. The method of claim 12, wherein said subject comprises an abnormal expression level of a NOTCH1 protein.

21. The method of claim 12, wherein said NOTCH1-related disease is selected from the group consisting of leukemia, lymphoma, carcinoma, sarcoma, blastoma, and germ cells tumors.

22. The method of claim 12, wherein said NOTCH1-related disease is selected from the group consisting of T cell acute lymphoblastic leukemia (T-ALL), Chronic lymphocytic leukemia (CLL), Melanoma, Cholangiocarcinoma (CCC), Colorectal cancer, Lung adenocarcinoma, Glioblastoma, Renal cell carcinoma, Ovarian cancer, Prostate cancer, Breast cancer, Pancreatic ductal adenocarcinoma (PDAC), Cervical cancer, Head and neck squamous cell carcinomas (HNSCC), Hepatocellular carcinoma (HCC), Medulloblastoma, B cell acute lymphoblastic leukemia (B-ALL), Acute myeloid leukemia (AML), Small cell lung carcinoma (SCLC), Lung squamous cell carcinoma (SqCC), Cutaneous squamous cell carcinoma (SqCC), and Chronic myelomonocytic leukemia (CMML).

23. The method of claim 22, wherein said NOTCH1-related disease is T-ALL.

* * * * *